(12) United States Patent
Koehler et al.

(10) Patent No.: US 10,285,591 B2
(45) Date of Patent: May 14, 2019

(54) USER INTERFACES FOR CONTINUOUS GLUCOSE MONITORING

(71) Applicant: DexCom, Inc., San Diego, CA (US)

(72) Inventors: Katherine Yerre Koehler, San Diego, CA (US); Esteban Cabrera, Jr., San Diego, CA (US); Eric Cohen, San Diego, CA (US); Mark Dervaes, Carlsbad, CA (US); Rian Draeger, San Diego, CA (US); Sheryl Sadsarin Gaano, San Diego, CA (US); Thomas Hall, San Diego, CA (US); Paul Kramer, Austin, TX (US); Shawn Larvenz, Ramona, CA (US); Michael Robert Mensinger, San Diego, CA (US); Paul Noble-Campbell, Austin, TX (US); Andrew Atilla Pal, San Diego, CA (US); Eli Reihman, San Diego, CA (US); Brian Christopher Smith, San Marcos, CA (US); Angela Marie Traven, San Marcos, CA (US)

(73) Assignee: DexCom, Inc., San Diego, CA (US)

( * ) Notice: Subject to any disclaimer, the term of this patent is extended or adjusted under 35 U.S.C. 154(b) by 388 days.

(21) Appl. No.: 14/919,611

(22) Filed: Oct. 21, 2015

(65) Prior Publication Data
US 2016/0113596 A1 Apr. 28, 2016

Related U.S. Application Data

(63) Continuation of application No. 14/919,528, filed on Oct. 21, 2015.

(Continued)

(51) Int. Cl.
*A61B 5/00* (2006.01)
*G16H 40/63* (2018.01)
(Continued)

(52) U.S. Cl.
CPC ............ *A61B 5/0004* (2013.01); *A61B 5/002* (2013.01); *A61B 5/14503* (2013.01);
(Continued)

(58) Field of Classification Search
CPC ... A61B 5/14532; H04L 67/12; H04L 43/065; H04L 43/0817; G06F 19/3406
See application file for complete search history.

(56) References Cited

U.S. PATENT DOCUMENTS 7,000,100 B2 2/2006 Lacombe et al.
7,024,321 B1 4/2006 Deninger et al.
(Continued)

OTHER PUBLICATIONS

Google Play, ICE: In Case of Emergency, 2012, Web, Retrieved from: https://play.google.com/store/apps/details?id=com.appventive.ice.*

*Primary Examiner* — Christian Jang
(74) *Attorney, Agent, or Firm* — Knobbe Martens Olson & Bear, LLP

(57) ABSTRACT

The subject matter disclosed herein provides methods for presenting glucose level data. Glucose data for a patient may be received. A current glucose level and a rate of change of the current glucose level may be determined based on the received glucose data. A first interface may be displayed on a screen of a device. The first interface may include a unitary icon. The unitary icon may display the current glucose level and a visualization of the rate of change. Related apparatus, systems, techniques, and articles are also described.

25 Claims, 36 Drawing Sheets

US 10,285,591 B2
Page 2

Related U.S. Application Data

(60) Provisional application No. 62/067,303, filed on Oct. 22, 2014.

(51) Int. Cl.
  *G06F 19/00* (2018.01)
  *A61B 5/145* (2006.01)
  *H04L 12/26* (2006.01)
  *H04L 29/08* (2006.01)

(52) U.S. Cl.
  CPC ........ *A61B 5/14532* (2013.01); *A61B 5/7271* (2013.01); *A61B 5/7275* (2013.01); *A61B 5/7282* (2013.01); *A61B 5/742* (2013.01); *A61B 5/743* (2013.01); *A61B 5/7405* (2013.01); *A61B 5/746* (2013.01); *A61B 5/7435* (2013.01); *A61B 5/7455* (2013.01); *G06F 19/00* (2013.01); *G06F 19/3468* (2013.01); *G16H 40/63* (2018.01); *H04L 43/065* (2013.01); *H04L 43/0817* (2013.01); *H04L 67/12* (2013.01); *A61B 2560/0475* (2013.01)

(56) References Cited

U.S. PATENT DOCUMENTS

| | | | |
|---|---|---|---|
| 7,052,472 B1 * | 5/2006 | Miller | A61B 5/01 600/549 |
| D626,143 S | 10/2010 | Karten et al. | |
| 8,002,701 B2 | 8/2011 | Sasha et al. | |
| 8,332,825 B2 | 12/2012 | Mital et al. | |
| 8,684,929 B2 * | 4/2014 | Heaton | G16H 40/63 600/365 |
| 9,041,730 B2 | 5/2015 | Johnson et al. | |
| 9,662,438 B2 | 5/2017 | Kamen et al. | |
| 9,717,447 B2 | 8/2017 | Larsen et al. | |
| 2005/0038332 A1 * | 2/2005 | Saidara | A61B 5/0002 600/347 |
| 2008/0108884 A1 * | 5/2008 | Kiani | A61B 5/0002 600/301 |
| 2009/0221890 A1 | 9/2009 | Daniel et al. | |
| 2011/0009727 A1 * | 1/2011 | Mensinger | A61B 5/7445 600/365 |
| 2011/0193704 A1 | 8/2011 | Harper et al. | |
| 2011/0201911 A1 | 8/2011 | Saffer et al. | |
| 2013/0106684 A1 * | 5/2013 | Weast | G06F 19/3481 345/156 |
| 2013/0172688 A1 | 7/2013 | Allen et al. | |
| 2014/0012118 A1 | 1/2014 | Mensinger et al. | |
| 2014/0012510 A1 | 1/2014 | Mensinger et al. | |
| 2014/0144167 A1 | 5/2014 | Yamauchi et al. | |
| 2014/0184422 A1 | 7/2014 | Mensinger et al. | |
| 2014/0374275 A1 | 12/2014 | Morales et al. | |
| 2015/0045641 A1 | 2/2015 | Rule | |
| 2015/0119655 A1 | 4/2015 | Mayou et al. | |
| 2015/0119667 A1 | 4/2015 | Reihman et al. | |
| 2015/0123810 A1 | 5/2015 | Hernandez-Rosas et al. | |

* cited by examiner

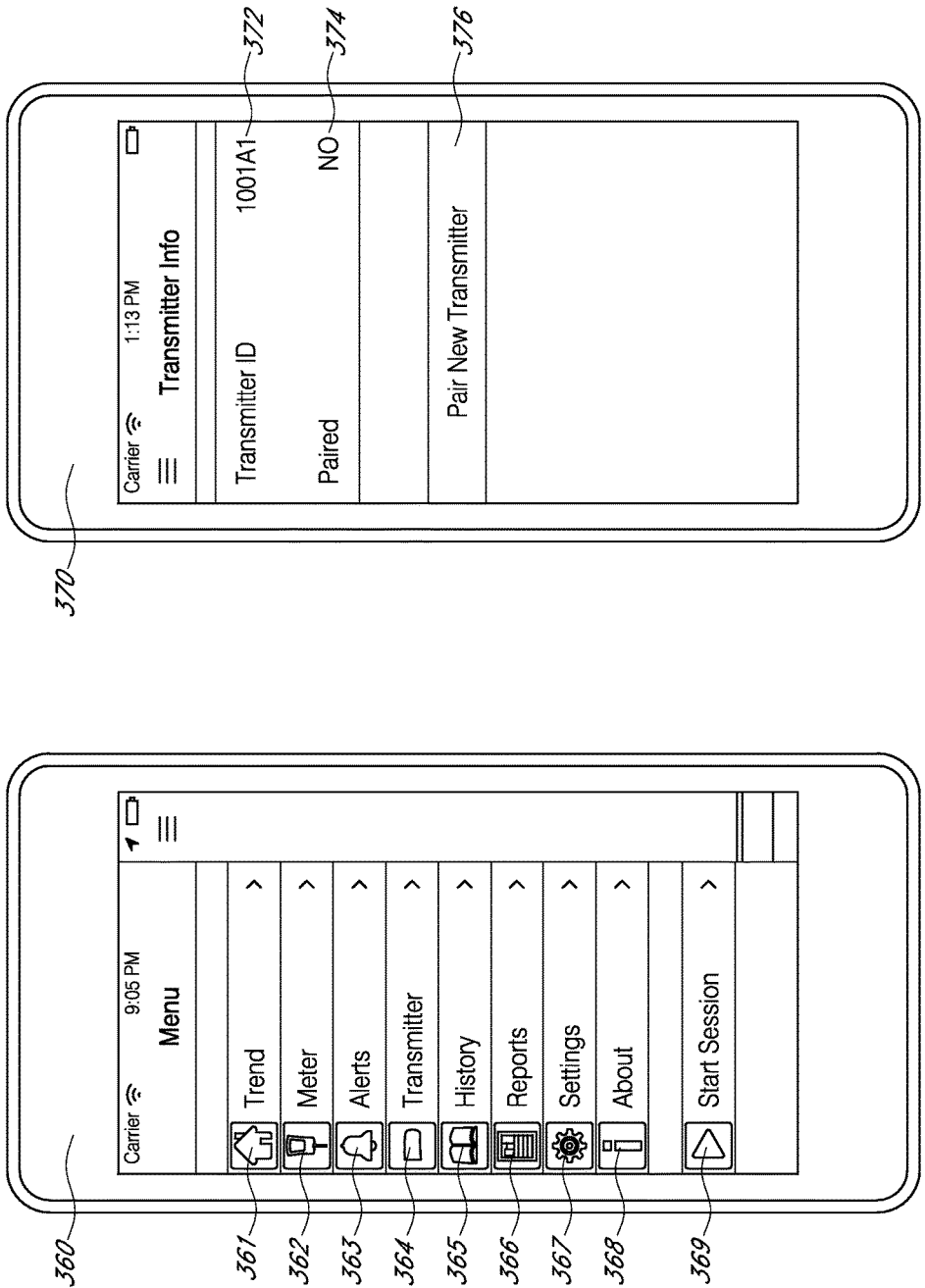

USER INTERFACES FOR CONTINUOUS GLUCOSE MONITORING

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 14/919,528, filed Oct. 21, 2015, which claims the benefit of U.S. Provisional Application No. 62/067,303, filed Oct. 22, 2014. Each of the aforementioned applications is incorporated by reference herein in its entirety, and each is hereby expressly made a part of this specification.

FIELD

The present disclosure generally relates to the presentation of glucose data on a computing device and, in particular, to the presentation of a patient's glucose data in a manner that provides the current status and projected status at a glance.

BACKGROUND

Diabetes mellitus is a disorder in which the pancreas cannot create sufficient insulin. In a diabetic state, a person suffering from high blood sugar may experience an array of physiological side effects associated with the deterioration of small blood vessels. These side effects may include, for example, kidney failure, skin ulcers, bleeding into the vitreous of the eye, and the like. A hypoglycemic reaction, such as a low blood sugar event, may be induced by an inadvertent overdose of insulin, or after a normal dose of insulin or glucose-lowering agent. In a severe hypoglycemic reaction, there may be a high risk for headache, seizure, loss of consciousness, and coma.

A diabetic person may carry a self-monitoring blood glucose (SMBG) monitor which typically requires the user to prick his or her finger to measure his or her glucose levels. Given the inconvenience associated with traditional finger pricking methods, it is unlikely that a diabetic will take a timely SMBG measurement and, consequently, may be unaware whether his or her blood glucose value is indicative of a dangerous situation.

Consequently, a variety of non-invasive, transdermal (e.g., transcutaneous) and/or implantable electrochemical sensors are being developed for detecting and/or quantifying blood glucose values. These devices generally transmit raw or minimally processed data for subsequent analysis at a remote device. The remote device may have a display that presents information to a user hosting the sensor. In some systems, a patient may check his or her glucose level on a hand held computing device. There are challenges to presenting this information discreetly and reliably.

SUMMARY

Methods and apparatus, including computer program products, are provided for presenting glucose level data.

In one aspect, glucose data is received for a patient. A current glucose level and a rate of change of the current glucose level are determined based on the received glucose data. A first interface is displayed on a screen of a device. The first interface includes a unitary icon. The unitary icon displays the current glucose level and a visualization of the rate of change.

The above methods, apparatus, and computer program products may, in some implementations, further include one or more of the following features.

The rate of change may be based on at least the current glucose level and a second value. The second value may be representative of the glucose level of the patient at a second time preceding a time associated with the current glucose level.

The visualization of the rate of change may include one or more arrows oriented in a first direction. The first direction may be representative of whether the current glucose level is increasing, decreasing, or stable. The visualization of the rate of change may change by at least varying the first direction of the one or more arrows.

The one or more arrows oriented in the first direction may have a first pointing direction of 0° when the rate of change is increasing, may have a second pointing direction of 180° when the rate of change is decreasing, or may have a third pointing direction of 90° when the rate of change is stable.

The number of the one or more arrows may be selected based on a magnitude of the rate of change.

The unitary icon may possess a background color based on at least the current glucose level.

The background color may be a first color when the current glucose level is associated with a high glucose level, a second color when the current glucose level is associated with a target glucose level, and a third color when the current glucose level is associated with a low glucose level.

The first interface may further include a graph displaying a plurality of glucose levels over a predetermined period of time. The plurality of glucose levels may include a plurality of data points representative of the current glucose level and one or more historical values.

The graph may be separated into one or more of a first band associated with a high glucose level, a second band associated with a target glucose level, and a third band associated with a low glucose level. The first band, the second band, and the third band may be different colors.

The current glucose level may be displayed on a rightmost side of the graph in a current band. The current band may include the first band, the second band, or the third band. The color of the current band may match the background color of the unitary icon.

The plurality of data points may include at least a first data point type and a second data point type. The current glucose level may be displayed on the graph using the first data point type. The one or more historical values may be displayed on the graph using the second data point type.

The first data point type may be a first circle having a black border and a white background. The second data point type may be a second circle having a black border and a black background.

The plurality of data points may further include a third data point type representative of an event. The event may be associated with a nearest one of the plurality of data points.

The third data point type may be a shape that surrounds the first data point type or the second data point type.

A description of the event may be displayed on the first interface when the third data point type is selected.

A second interface may be displayed when the screen is rotated. The second interface may include an extended view of the graph in the first user interface over a user-selected period of time. The user-selected period of time may be one hour, three hours, six hours, twelve hours, or twenty-four hours.

A miniature icon may be displayed on the second interface when one of the plurality of data points is selected. The miniature icon may display a glucose level associated with the selected data point. The miniature icon may further include a background color based on a value of the selected data point relative to one or more threshold values.

The first interface may further include a second icon that indicates whether a mute switch on the device is enabled.

The first interface may further include a third icon that indicates whether a calibration measurement is needed.

The first interface may further include a fourth icon that allows one or more events to be entered when the fourth icon is selected. The one or more events may be associated with one or more of food consumption, beverage consumption, exercise, and administration of a substance.

The first interface may further include a fifth icon that indicates whether remote monitoring is enabled, disabled, or experiencing an error.

The current glucose level may be shared with one or more remote monitors approved by the patient when the remote monitoring is enabled. The remote monitoring may experience an error when the device is unable to connect with one or more remote monitors approved by the patient.

The fifth icon may have a first color when the remote monitoring is disabled. The fifth icon may have one or more colors when the remote monitoring is enabled. The one or more colors may be different from the first color. The fifth icon may have a badge when the remote monitoring is experiencing an error.

The unitary icon may include a circular shape with one or more arrows that rotate about the circular shape based on the rate of change of the current glucose level.

The current glucose level may be displayed inside the circular shape.

In another aspect, a current glucose level of a patient and a rate of change of the current glucose level are accessed. A clinical risk to the patient is determined. A first interface is displayed on a screen of a device. The first interface includes a visualization of the clinical risk and a unitary icon. The unitary icon displays the current glucose level and a visualization of the rate of change.

The above methods, apparatus, and computer program products may, in some implementations, further include one or more of the following features.

The determining the clinical risk may be based on the current glucose level and the rate of change. The clinical risk may be associated with an extrapolated glucose level.

The rate of change may be based on at least the current glucose level and a second value. The second value may be representative of the glucose level of the patient at a second time. The second time may precede a time associated with the current glucose level.

The clinical risk may be high when one or more of the following conditions are satisfied: the current glucose level is greater than a first threshold value and the rate of change is increasing; the current glucose level is greater than the first threshold value and the rate of change is stable; the current glucose level is less than a second threshold value and the rate of change is decreasing; and the current glucose level is less than the second threshold value and the rate of change is stable.

The clinical risk may be low when one or more of the following conditions are satisfied: the current glucose level is greater than the first threshold value and the rate of change is decreasing; the current glucose level is less than the second threshold value and the rate of change is increasing; and the current glucose level is between the first threshold value and the second threshold value and the rate of change is stable.

The visualization of the clinical risk may include shading the screen of the device with a first color when the clinical risk is high. The visualization of the clinical risk may include shading the screen of the device with a second color when the clinical risk is low.

The visualization of the clinical risk may include incorporating a color gradient into a background of the unitary icon. The color gradient may include a plurality of colors. The plurality of colors may be arranged in a pattern to illustrate the clinical risk.

The visualization of the clinical risk may include displaying the extrapolated glucose level on a second unitary icon.

The visualization of the rate of change may include one or more arrows oriented in a first direction. The first direction may be representative of whether the current glucose level is increasing, decreasing, or stable.

The one or more arrows oriented in the first direction may have a first pointing direction of 0° when the rate of change is increasing, may have a second pointing direction of 180° when the rate of change is decreasing, or may have a third pointing direction of 90° when the rate of change is stable.

A number of the one or more arrows may be selected based on a magnitude of the rate of change.

The visualization of the clinical risk may include flashing the one or more arrows.

The visualization of the clinical risk may include enlarging the one or more arrows.

The visualization of the clinical risk may include shading the one or more arrows and a background of the unitary icon with different colors.

The determining the clinical risk may be further based on one or more events. The one or more events may be associated with one or more of food consumption, beverage consumption, exercise, and administration of a substance.

One or more of the current glucose level and the rate of change may be displayed on a locked screen when the device is locked.

In an additional aspect, an application is executed to generate one or more alerts on a device relating to a glucose level of a patient. The executing includes accessing a current glucose level of a patient. The executing also includes accessing one or more conditions associated with the one or more alerts. The one or more conditions define a relationship between the current glucose level and one or more threshold values. The executing further includes determining whether the one or more conditions are satisfied. The executing also includes generating the one or more alerts when the one or more conditions are satisfied. The one or more alerts that are generated are based on one or more of a state of the device and a state of the application.

The above methods, apparatus, and computer program products may, in some implementations, further include one or more of the following features.

The state of the device may include one or more of a locked state, an unlocked state, a muted stated, and an unmuted state. The state of the application may include an active state or an inactive state.

The application may be in an active state when the application is displayed on a foreground of a screen of the device. The application may be in an inactive state when the application is displayed on a background of the screen of the device.

The one or more alerts may include one or more non-audible alerts when the device is in a muted state. The one or more non-audible alerts may include one or more of a vibration or a visualization displayed on a screen of the device. The visualization may include a flashing screen or a shaded screen.

The one or more alerts may include one or more local notifications displayed on a locked screen of the device when the device is in a locked state. The one or more local notifications may display an identifier associated with the one or more alerts.

The one or more local notifications may further display the current glucose level and a trend arrow representative of a rate of change of the current glucose level.

The one or more alerts may include one or more banners when the device is in an unlocked state and when the application is in an inactive state. The one or more banners may display an identifier associated with the one or more alerts for a predetermined period of time on a screen of the device.

The one or more alerts may further include one or more audible alerts.

The one or more alerts may be re-generated at a predetermined frequency until an acknowledgment of the one or more alerts is received or when the one or more conditions are no longer satisfied.

The one or more alerts may include an urgent low alert, a low alert, a high alert, a rise rate alert, a fall rate alert, or a no data alert.

The urgent low alert may not be modifiable.

The one or more threshold values associated with the one or more alerts may be adjusted during a predetermined period of time. The adjusting may cause the one or more conditions of one or more alerts to be satisfied more frequently than without the adjusting. The adjusting may be performed during a night mode.

In yet another aspect, one or more alerts relating to a glucose level of a patient are maintained. The one or more alerts are generated when one or more conditions are satisfied. The one or more conditions define a relationship between a current glucose level of the patient and one or more threshold values. It is detected whether a mute function on the first device is enabled. The generation of the one or more alerts is modified based on the detecting.

The above methods, apparatus, and computer program products may, in some implementations, further include one or more of the following features.

The patient may be notified that the mute switch is enabled using one or more notifications. The notifying may be based on the detecting.

An image may be displayed on a screen of the first device. The image may indicate that the mute function is enabled on the first device. A message may be displayed on the screen. The message may indicate that the mute function is enabled on the first device. An e-mail may be sent to the patient. The e-mail may indicate that the mute function is enabled on the first device.

One or more vibrating alerts may be generated until an acknowledgment of the one or more notifications is received.

A message may be sent to a second device. The message may cause the second device to notify one or more remote monitors of the patient that the mute function is enabled on the first device.

The modifying may include initiating a communication with one or more remote monitors of the patient. The communication may indicate that the one or more conditions of the one or more alerts are satisfied. The communication may include one or more of a phone call, a text message, and an e-mail.

The modifying may include sending a message to a second device. The message may indicate that the one or more conditions of the one or more alerts on the first device are satisfied and may cause the second device to generate the one or more alerts.

The modifying may include adjusting the one or more threshold values. The adjusting may cause the one or more conditions of the one or more alerts to be satisfied more frequently than without the adjusting. The adjusting the one or more threshold values may be performed during a predetermined period of time.

A message may be sent to a pump in communication with the first device. The message may cause the pump to suspend delivery of a medication to the patient.

In another aspect, an application is executed on a first device for monitoring a glucose level of a patient. It is determined whether the application on the first device has stopped execution. A notification is generated based on the determination. The notification indicates that the application has stopped execution.

The above methods, apparatus, and computer program products may, in some implementations, further include one or more of the following features.

The notification may be generated before the application has stopped execution and may indicate that the application will terminate.

The notification may be locally generated on the first device.

A message may be sent to a second device. The message may cause the second device to notify one or more remote monitors of the patient that the application has stopped execution.

The application may be activated upon receiving a communication from a third device. The communication may be associated with an operation of the application. The first device and the third device may be paired using a Bluetooth connection.

An alarm may be set on the first device. The alarm may be configured to be activated at a predetermined time. The alarm may be reset on the first device before the alarm is activated by extending the predetermined time. Determining whether the application has stopped execution may be based on an activation of the alarm.

The notification may be generated upon receiving a message indicating that the application has failed to communicate with a second device during a predetermined period of time.

The determining may include determining whether a battery of the first device has sufficient power to continue operation of the first device during a predetermined period of time.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated herein and constitute a part of this specification, show certain aspects of the subject matter disclosed herein and, together with the description, help explain some of the principles associated with the subject matter disclosed herein. In the drawings.

FIG. 3I illustrates a menu in accordance with some exemplary implementations;

FIG. 3J illustrates a user interface for displaying transmitter information in accordance with some exemplary implementations;

Figure 1:
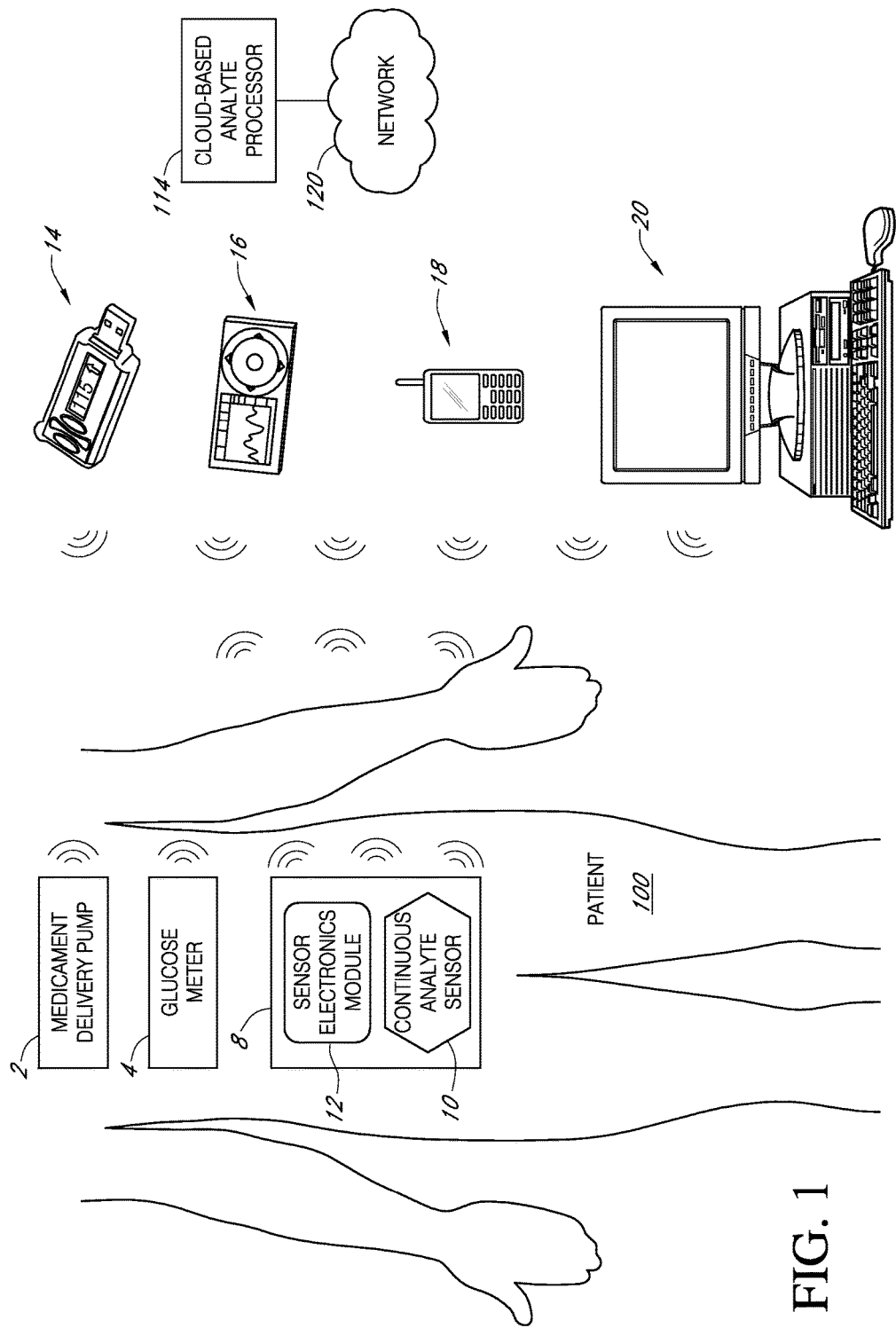
FIG. 1 illustrates a continuous analyte sensor in accordance with some exemplary implementations.

Like labels are used to refer to same or similar items in the drawings.

DETAILED DESCRIPTION

A continuous glucose monitoring system can closely monitor a patient's glucose levels at frequent intervals. By increasing the frequency of glucose level measurements and sending these measurements to the patient, the patient may be able to prevent prolonged durations of high glucose levels which may damage tissues over time and prevent or shorten the duration of dangerously low glucose levels. The continuous glucose monitoring system may have a dedicated display device, such as a receiver. A patient or a remote monitor may use this receiver to view the patient's glucose levels and receive alerts when the patient's glucose level becomes high or low. Because patients may find it cumbersome to carry a separate glucose monitoring device, it may be advantageous to incorporate the receiver's functionality into a multi-functional computing device, such as a smart phone or other hand-held device.

FIG. 1 depicts an exemplary system that includes a continuous analyte sensor system (e.g., continuous glucose meter) 8. The continuous analyte sensor system 8 may include a sensor electronics module 12 and a continuous analyte sensor 10 that is connected to a patient 100. The system may include other devices and/or sensors, such as medicament delivery pump 2 and blood glucose meter 4. The continuous analyte sensor 10 may be physically connected to sensor electronics module 12 and may be integral with (e.g., non-releasably attached to) or releasably attachable to the continuous analyte sensor 10. The sensor electronics module 12, medicament delivery pump 2, and/or blood glucose meter 4 may couple with one or more devices, such as display devices 14, 16, 18, and 20.

It should be understood that FIG. 1 is for illustrative purposes, and that the system can include other components as well. For example, the system can further include a gastric pacemaker that communicates with the continuous analyte sensor system 8 and medicament delivery pump 2. The components of the system can communicate with one another to trigger gastric pacemaker to perform pacing to promote processing of food/drink of the patient. To illustrate, the continuous glucose sensor system 8 can trigger a message to the gastric pacemaker to begin pacing if a hyperglycemic event has been detected by the system, or to stop pacing when measured glucose levels are below or within predefined threshold(s).

The system can also communicate to other devices in some implementations. For example, the system can communicate with electronics of an automobile. A display of the automobile electronics can be used as a display device to display and/or alert a user of glucose levels measured by the analyte sensor system 8. Further, the automobile electronics can facilitate operation of the automobile depending upon glucose levels measured by the analyte sensor system. For instance, the automobile electronics can disable ignition if the glucose levels are too low, or pull the automobile over to the side of the road and stop in an instance where the automobile includes autonomous driving capabilities.

In some exemplary implementations, the system may include a cloud-based analyte processor 114 configured to analyze analyte data (and/or other patient related data) provided via network 120 (e.g., via wired, wireless, or a combination thereof) from sensor system 8 and other devices, such as display devices 14, 16, 18, and 20, associated with the host (also referred to as a patient). Cloud-based analyte processor 114 may be configured to generate reports providing high-level information, such as statistics, regarding the measured analyte over a certain timeframe.

In some exemplary implementations, the sensor electronics module 12 may include electronic circuitry associated with measuring and processing data generated by the continuous analyte sensor (e.g., continuous glucose meter) 10. This generated continuous sensor data may also include algorithms, which can be used to process and calibrate the continuous sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor.

The sensor electronics module 12 may couple (e.g., wirelessly and the like) with one or more devices, such as display devices 14, 16, 18, and/or 20. The display devices 14, 16, 18, and/or 20 may be configured to present (and/or alarming) information, such as sensor information transmitted by the sensor electronics module 12 for display at the display devices 14, 16, 18, and/or 20. In some implementations, display devices 14, 16, 18, and/or 20 may implement the algorithms performed by sensor electronics module 12.

The display devices may include a relatively small, key fob-like display device 14, a relatively large, hand-held display device 16, a cellular phone (e.g., a smart phone, a tablet, and the like) 18, a computer 20, and/or any other user equipment configured to at least present information (e.g., a medicament delivery information, discrete self-monitoring glucose readings, heart rate monitor, caloric intake monitor, and the like).

In some exemplary implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device) and may be configured to display certain types of displayable sensor information, such as a numerical value and an arrow.

In some exemplary implementations, the relatively large, hand-held display device 16 may comprise a hand-held receiver device, a palm-top computer, and the like. This large display device may include a relatively large display (e.g., larger than the small display device) that may be configured to display information, such as a graphical representation of the continuous sensor data including current and historic sensor data output by sensor system 8.

In some exemplary implementations, the continuous analyte sensor (e.g., continuous glucose meter) 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some exemplary implementations, the continuous analyte sensor 10 may analyze a plurality of intermittent blood samples, although other analytes may be used as well.

In some exemplary implementations, the continuous analyte sensor 10 may comprise a glucose sensor configured to measure glucose in the body using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a patient 100. The data stream may be raw data signal, which is converted into a calibrated and/or filtered data stream used to provide a value of glucose to a user, such as a patient or a remote monitor (e.g., a parent, a relative, a guardian, a teacher, a doctor, a nurse, or any other individual that has an interest in the wellbeing of the patient). Moreover, the continuous analyte sensor 10 may be implemented as at least one of the following types of sensors: an implantable glucose sensor, a transcutaneous glucose sensor, implanted in a host vessel or extracorporeally, a subcutaneous sensor, a refillable subcutaneous sensor, an intravascular sensor, and a non-invasive analyte sensor.

Although the description herein refers to some implementations that include a continuous analyte sensor 10 comprising a glucose sensor, the continuous analyte sensor 10 may comprises other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, Acetyl Co A, triglycerides, fatty acids, intermediaries in the citric acid cycle, choline, insulin, cortisol, testosterone, and the like.

Figure 2A:
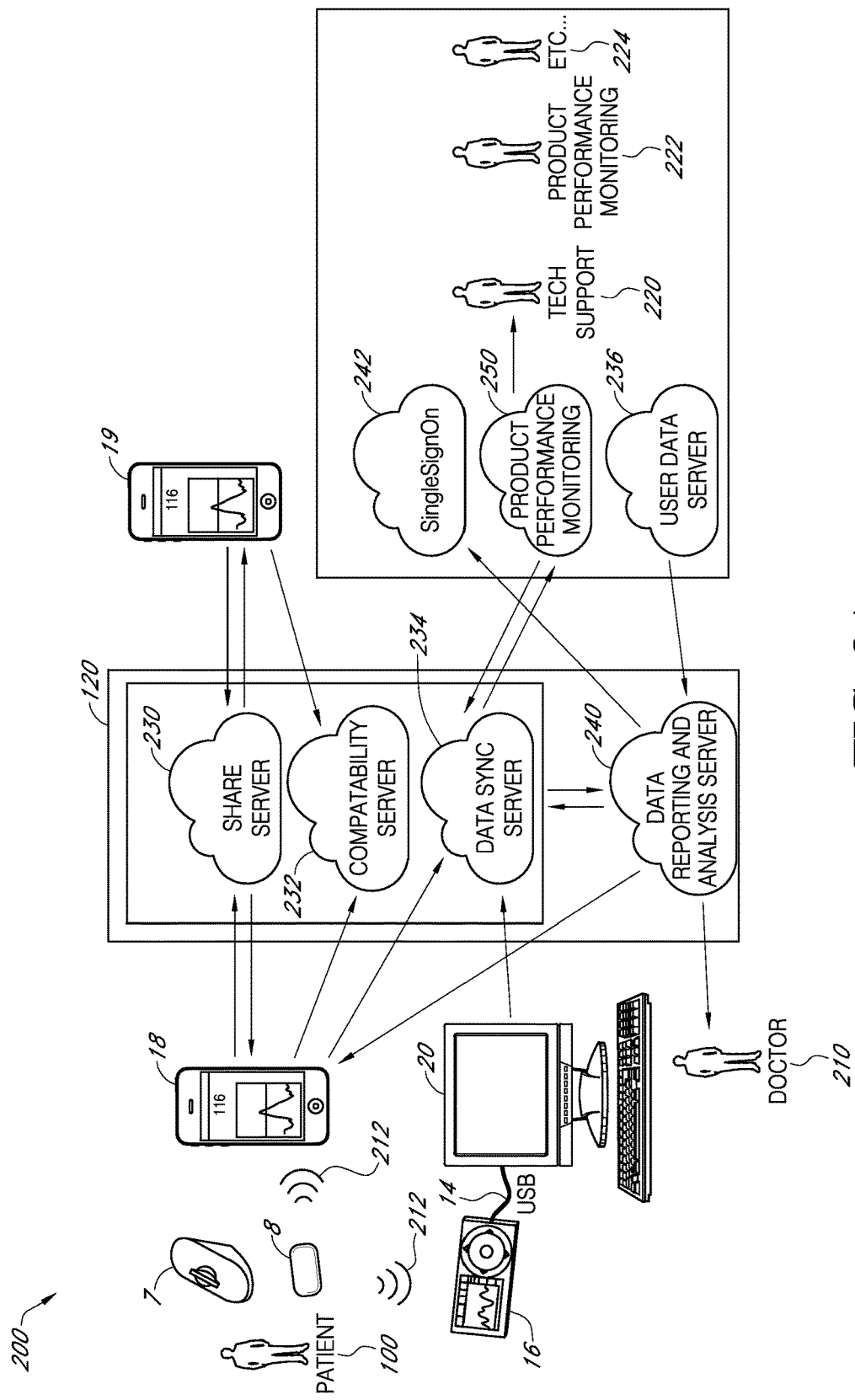
FIG. 2A illustrates a system diagram in accordance with some exemplary implementations.

FIG. 2A depicts a system 200 for exchanging and communicating glucose level data among various components in accordance with some implementations. System 200 is a variation of the system of FIG. 1A. In particular, system 200 includes additional components that may receive and/or exchange information with sensor system 8 and further identifies the features of network 120. Patient 100 may have a continuous glucose sensor system 8 on his or her body. Sensor system 8 may be applied to patient 100 using an application device 7. Data receiver 16 and a primary hand held computing device 18 may communicate with the sensor system 8. The system may also include one or more desktop or laptop computing devices 20, a network 120 that includes one or more servers, one or more secondary hand held computing devices 19, and one or more additional persons who monitor the performance of the system. These other persons can include technical support personnel 220, product performance monitoring personnel 222, and remote monitors (e.g., family members, guardians, doctors, nurses) 224.

The continuous glucose sensor system 200 may include various connections between the electronic components. Sensor system 8 may be connected to primary hand held computing device 18 and receiver 16 via a low-energy, close proximity wireless connections 212. In some implementations, connection 212 may utilize Bluetooth® wireless technology. Receiver 16 and laptop or desktop computing device 20 may be connected via a wired and/or wireless connection 14. This wired and/or wireless connection 14 may utilize Universal Serial Bus (USB) ports, FireWire (e.g., IEEE 1394 High Speed Serial Bus) ports, and the like. Sensor system 8 may establish a constant or intermittent connection with primary hand held computing device 18 and receiver 16. In some implementations, receiver 16 and/or primary hand held computing device 18 may establish a constant or intermittent connection with sensor system 8. These intermittent connections may be established at one or more predetermined frequencies, such as every 3, 5, 7, or 10 minutes and the like.

Once a connection is established between sensor system 8 with one or more of receiver 16 and the primary hand held computing device 18, data corresponding to one or more glucose levels from patient 100 may be exchanged between these components. In some implementations, sensor system 8 may establish only one connection at a time such that such that the sensor system is either connected to receiver 16 or to primary hand held computing device 18. Each connection may be automatically ended or actively ended, such as after a predetermined amount of data has been transferred, after a predetermined amount of time, or after a user has initiated disconnection.

In some implementations, receiver 16 may be connected with computing device 20 via a device cradle. This cradle may connect electrical contacts on receiver 16 to a port on laptop or desktop computing device 20. Primary and secondary computing hand held devices 18 and 19 and laptop or desktop computing device 20 may communicate with each other via network 120.

Network 120 may include servers 230, 232, 234, and 240. In some implementations, servers 230, 232, 234, and 240 may be located in the cloud. While these servers are illustrated as separate devices in the implementation of FIG. 2A, they may be consolidated as a single server, or one or all of these illustrated servers may be distributed across multiple devices or servers.

In the systems of FIGS. 1 and 2A, patient 100 or another user may discreetly monitor the patient's current glucose level and clinical risk, as well as the functioning of the continuous glucose monitoring sensor system 8. The other user may be a remote monitor, such as a parent, guardian, physician, nurse, and the like. These remote monitors may remotely monitor the status of patient 100 using a hand held computing device 19. Remote monitoring server 230 may receive glucose level data from primary hand-held computing device 18 or computing device 20 and push this data to remote monitor devices 19. This data may also include settings for communicating with the remote monitor device 19. In some implementations, remote monitoring server 230 may also push one or more alerts to remote monitors as described below with respect to FIGS. 3E-G. Hand held computing device 19 may be a mobile smart phone, a tablet computer, a music or video player device with Internet connectivity, and the like. Although FIG. 2A illustrates remote monitor device 19 as a smart phone, the remote monitor may also access this information via a website, at a desktop computing device 19, and the like. In some implementations, the patient's hand held computing device 18 may be used in conjunction with receiver 16. Using both a dedicated receiver 16 and a hand held computing device 18 may provide insurance against scenarios where one of the devices 16 or 18 fails. This redundancy also provides a safeguard for receiving alarm notifications if, for example, one of the devices is placed in a silent mode or malfunctions.

Compatibility server 232 may ensure the compatibility of the various components in the system. This may include the compatibility of software (e.g., operating systems) running on devices 18, 19, and/or 20 with other components or necessary functions of system 200. Data sync server 234 may collect and store data and synchronize data transfer with additional components according to pre-defined permissions. For example, data sync server 234 may synchronize data with data analysis and reporting server 240 and product performance monitoring server 250.

In some implementations, system 200 of FIG. 2A may include one or more additional servers configured to monitor the performance of the system. User data server 236 may maintain medical information regarding users of the system (e.g., patient 100, remote monitors, and the like). Product performance monitoring server 250 may monitor the functioning of sensor system 8 and servers 230, 232, 234, and 240. Server 242 may provide account information, such as sign-on or login information, for accessing the various servers in system 200.

Figure 2B:
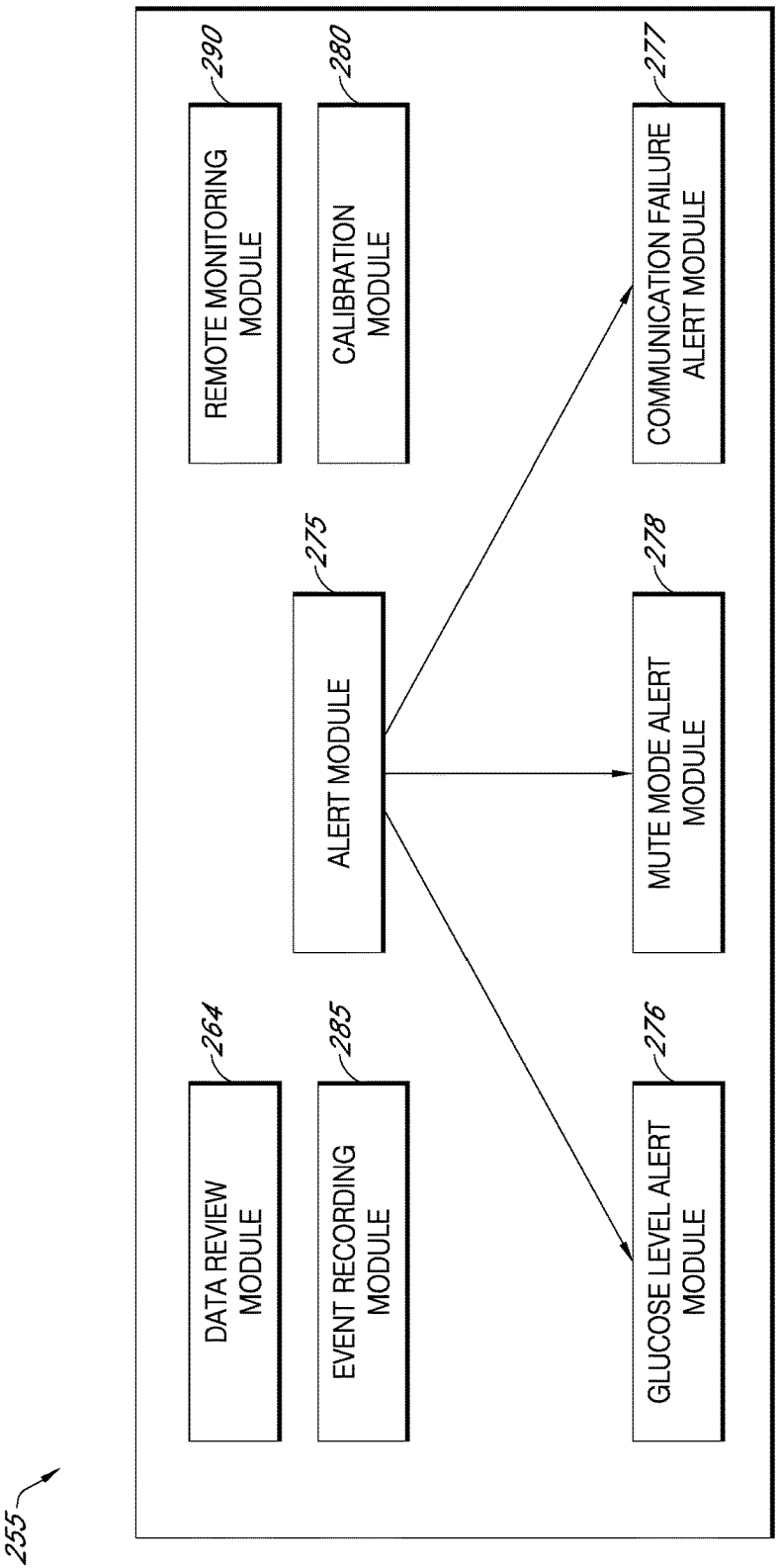
FIG. 2B illustrates a functional block diagram of the continuous glucose monitoring application in accordance with some exemplary implementations.

FIG. 2B illustrates a functional block diagram of the continuous glucose monitoring application 255 running on computing devices 18 and/or 19. This block diagram includes various software modules or features that control the behavior of application 255. For ease of explanation, the software modules or features of application 255 are described as being performed by computing devices 18 and/or 19. However, these software modules and features may be performed by other devices including, for example, cloud based analyte processor 114, any of servers 230, 232, 234, 236, 240, 242, and 250, or any combination thereof. The software modules and features of application 255 may include a data review module 264, an event recording module 285, a remote monitoring module 290, a calibration module 280, and an alert module 275. Each of these modules is described below.

Data review module 264 may display a patient's glucose levels. As described below with respect to FIGS. 4A-8D, the data review module 264 may provide information regarding a patient's current glucose level and its rate of change. Data review module 264 may also display a trend graph that illustrates variations in a patient's glucose level over time and may also indicate the presence of a clinical risk to the patient.

Remote monitoring module 290 may share a patient's glucose level information with other users, such as remote monitors 224. As described above with respect to system 200, share server 230 may push this information to secondary computing devices 19. A patient may use remote monitoring module 290 to invite remote monitors to receive this information and customize the type of information that may be viewed by invited remote monitors. Remote monitoring module 290 is described below with respect to FIGS. 3D and 3E.

A patient may use event recording module 285 to enter and recall events. Events may include food intake, medication intake, exercise, and the like. By recording this information, the patient may obtain a better understanding of how different types of events may influence his or her glucose levels. Event recording module 285 is described below with respect to FIGS. 3B and 3C.

Calibration module 280 may calibrate glucose data measurements received from sensor system 8. The calibration module 280 may alert a user when calibration measurements are needed. Calibration module 280 is described below with respect to FIG. 3H.

Alert module 275 may generate various alarms or alerts using glucose level alert module 276, mute mode alert module 278, and communication failure alert module 277. Glucose level alert module 276 may be a sub-module of alert module 275 and may be configured to generate an alarm if a patient's glucose level drops below or rises above a predetermined threshold value. A patient may use alert module 275 to set alerts for different parameters and designate which alerts to propagate to the remote monitors. Alert module 275 is described below with respect to FIGS. 9A-14 and 16A-17. Mute mode alert module 278 may be a sub-module of alert module 275 and may be configured to alert a patient if the patient's computing device 18 is determined to be muted. Because a patient may not hear any alerts when his or her device 18 is muted, mute mode alert module 278 may initiate one or more remedial actions, such as propagating one or more alerts to remote monitors. Mute mode alert module 278 is described below with respect to FIGS. 18 and 19. Communication failure alert module 277 may be a sub-module of alert module 275 and may be configured to alert a patient or remote follower if application 255 is determined to be terminated. This notification may prompt the patient to reboot or relaunch application 255 so that he or she may continue receiving glucose level data from sensor system 8. Communication failure alert module 277 is described below with respect to FIGS. 15 and 20.

Figure 3A:
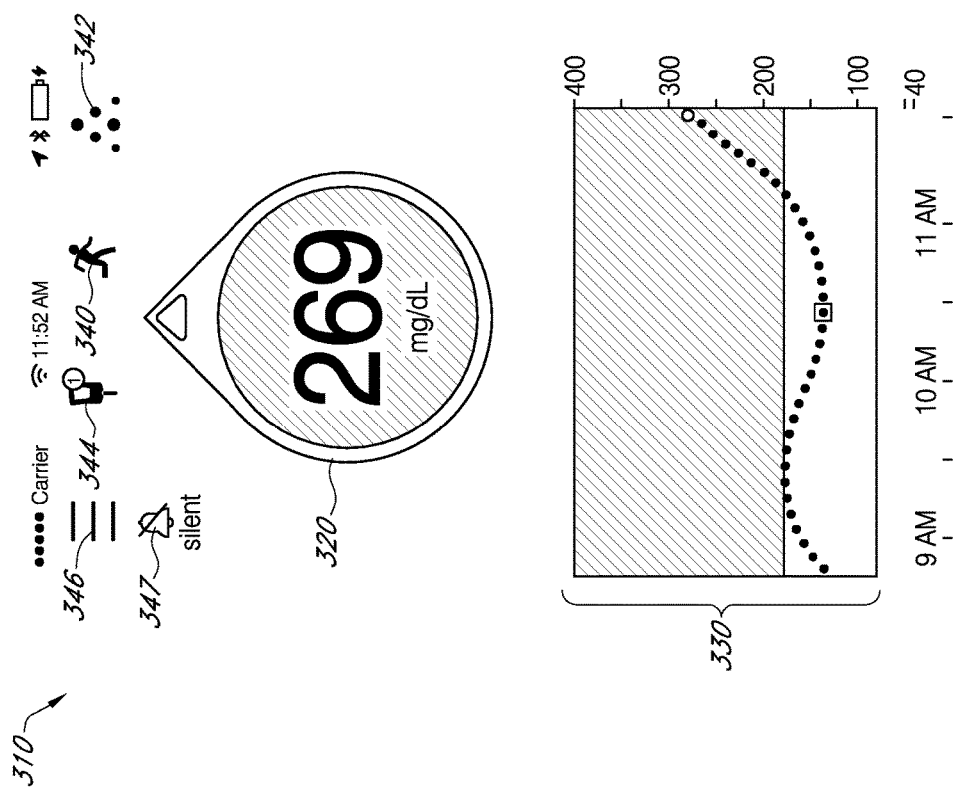
FIG. 3A illustrates a user interface for a mobile computing device in accordance with some exemplary implementations.
Figure 3C:
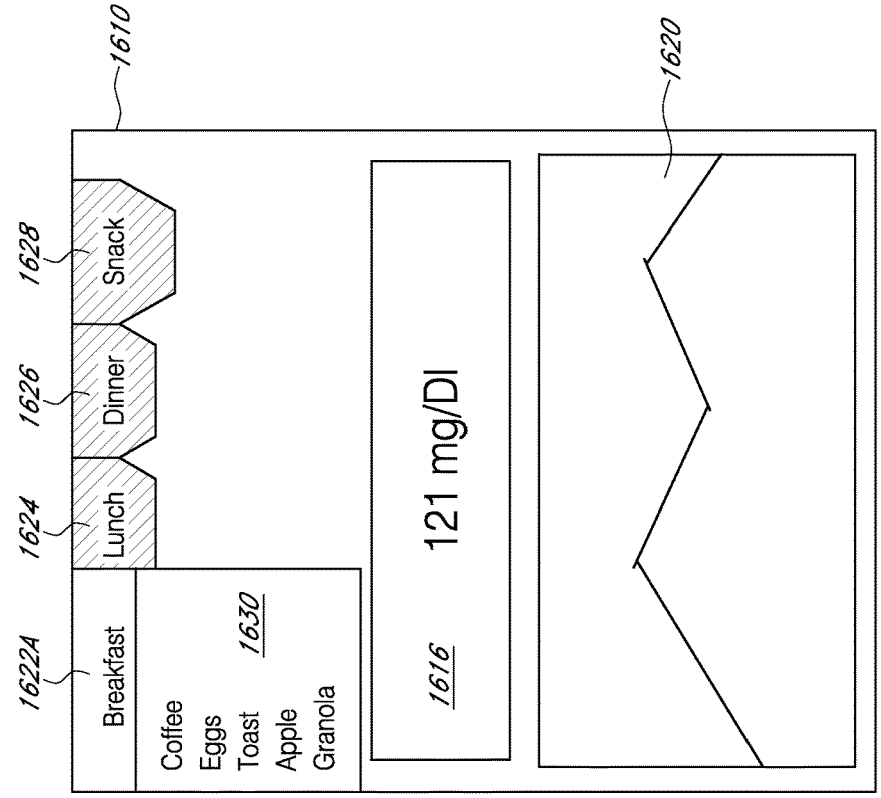
FIGS. 3B and 3C illustrate user interfaces for entering events in accordance with some exemplary implementations.

FIG. 3A illustrates a home screen 310 that may be displayed by data review module 264 when application 255 is launched. A user, such as a patient and/or remote monitor, may use home screen 310 to assess the status and clinical risk of a patient and to access various features associated with application 255. The home screen 310 may include one or more user-selectable icons 340, 342, 344, 346, and 347. Selection of an icon may cause application 255 to perform a function related to the icon (e.g., display a pop-up menu or open a new window relating to the function). A description of icons 340, 342, 344, 346, and 347 is provided below. Home screen 310 may also include a unitary icon 320 and a trend graph 330 that provides information regarding the patient's glucose levels. The unitary icon 320 and trend graph 330 are described in further detail below with reference to FIGS. 4A and 4B. Unitary icon 320 may provide an overall representation of a patient's glucose level. Unitary icon 320 may include one or more graphics, one or more symbols, and the like. The graphics and/or symbols in unitary icon 320 may be static or may change based on the patient's glucose level. While the graphics and/or symbols in unitary icon 320 are consolidated into a single unified image in the implementation of FIG. 3A, unitary icon 320 may be segmented into one or more non-contiguous graphics and/or symbols in other implementations.

A user may select event entry icon 340 to access event recording software module 285. As described above, a user may use event recording software module 285 to enter information regarding events that may affect the patient's glucose level. Events may include, for example, recent meals (e.g., food and beverage consumption), periods of activity or exercise, the administration of medication (e.g., bolus of insulin), and the like. Entered event information may be used to analyze the patient's health. In some implementations, as discussed below, event markers may be displayed on a glucose trend graph to allow a user to retrospectively analyze how different types of events affect the patient's glucose levels. The event information may also be used to determine when alerts should be generated (e.g., generating an alert 30 minutes after exercising) and whether adjustments are needed to the patient's medication regime (e.g., prompting the patient to administer a bolus of insulin after a particular event).

Figure 3B:
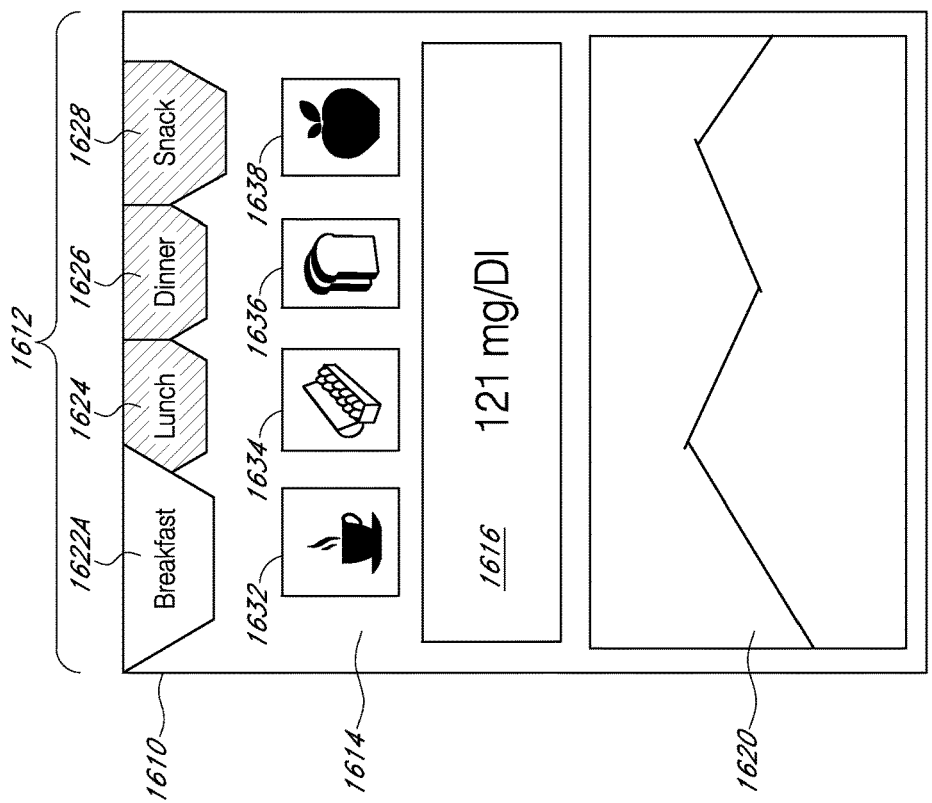

FIG. 3B illustrates an exemplary interface for entering meal-related event information. This interface may be displayed on the user interface of the patient's device 18 upon selection of the event entry icon 340 or may be automatically triggered when application 255 receives input indicating that the patent has eaten or is about to eat. The input may be one or more or time of day (e.g. lunchtime), a change in glucose levels indicative of eating a meal (e.g., a rising glucose level), location (e.g., a GPS location corresponding to a restaurant), and the like. A patient may use food input menu 1610 to provide information regarding recent meals, such as breakfast 1622A, lunch 1624, dinner 1626, and snacks 1628. Menu 1610 may include an area 1614 for logging the consumption of favorite foods. For example, if a user consumes coffee, eggs, bread, and fruit for breakfast, he or she may quickly log these items by selecting icons 1632, 1634, 1636, and 1638, respectively. The food input menu 1610 may also display the patient's current or most recent glucose level reading 1616 and a trend graph 1620. Trend graph 1620 may provide a graphical view of fluctuations in the patient's glucose level over a particular period of time.

FIG. 3C illustrates another interface for entering event information. This interface may appear when the patient selects breakfast tab 1622A from FIG. 3B. Drop down menu 1630 may list various breakfast items, such as coffee, eggs, toast, apple, granola, and the like. As a patient logs his or her food intake, event recording software module 285 may learn which foods are favored during each meal and appropriately populate drop down menu 1630. Module 285 may use this information to populate favorite foods section 1614 in FIG. 3B with different items. In some implementations, the module 285 may change the favorite foods that are displayed based on the time of day (e.g., display breakfast foods between 5 AM and 8 AM and display lunch foods between 11 AM and 1 PM).

Returning to FIG. 3A, icon 342 may dynamically change to indicate whether remote monitoring is enabled. To illustrate, a patient may wish to share his or her glucose levels with one or more remote monitors, such as a parent, guardian, or physician, particularly when the patient is a child or elderly person. A patient may enable or disable remote monitoring using primary device 18. In some circumstances, remote monitoring may not be enabled if, for example, the patient has not yet subscribed to the remote monitoring feature. Remote monitoring module 290 may display the status of the remote monitoring function by adjusting the appearance of icon 342 according to a plurality of states. In one implementation, the icon may be displayed in one of three states: an active sharing state, a remote monitoring disabled state, and a remote monitoring error state. The various states may be visually distinguishable by, for example, changing the color of icon 342 and/or displaying one or more badges with icon 342. In one exemplary implementation, icon 342 is displayed in multiple colors when device 18 is actively sharing data with other devices 19; icon 342 is displayed in a gray color when remote monitoring is disabled; and icon 342 is displayed in a gray color with a badge to indicate that device 18 is unable to share data due to a technical error (e.g., server 120 is unable to push date to secondary devices 19). It is understood that the above implementation is merely an example of how the icon 342 may visually change based on the status of the remote monitoring function, and that other visual changes may be used instead of or in addition to the above example.

Figure 3D:
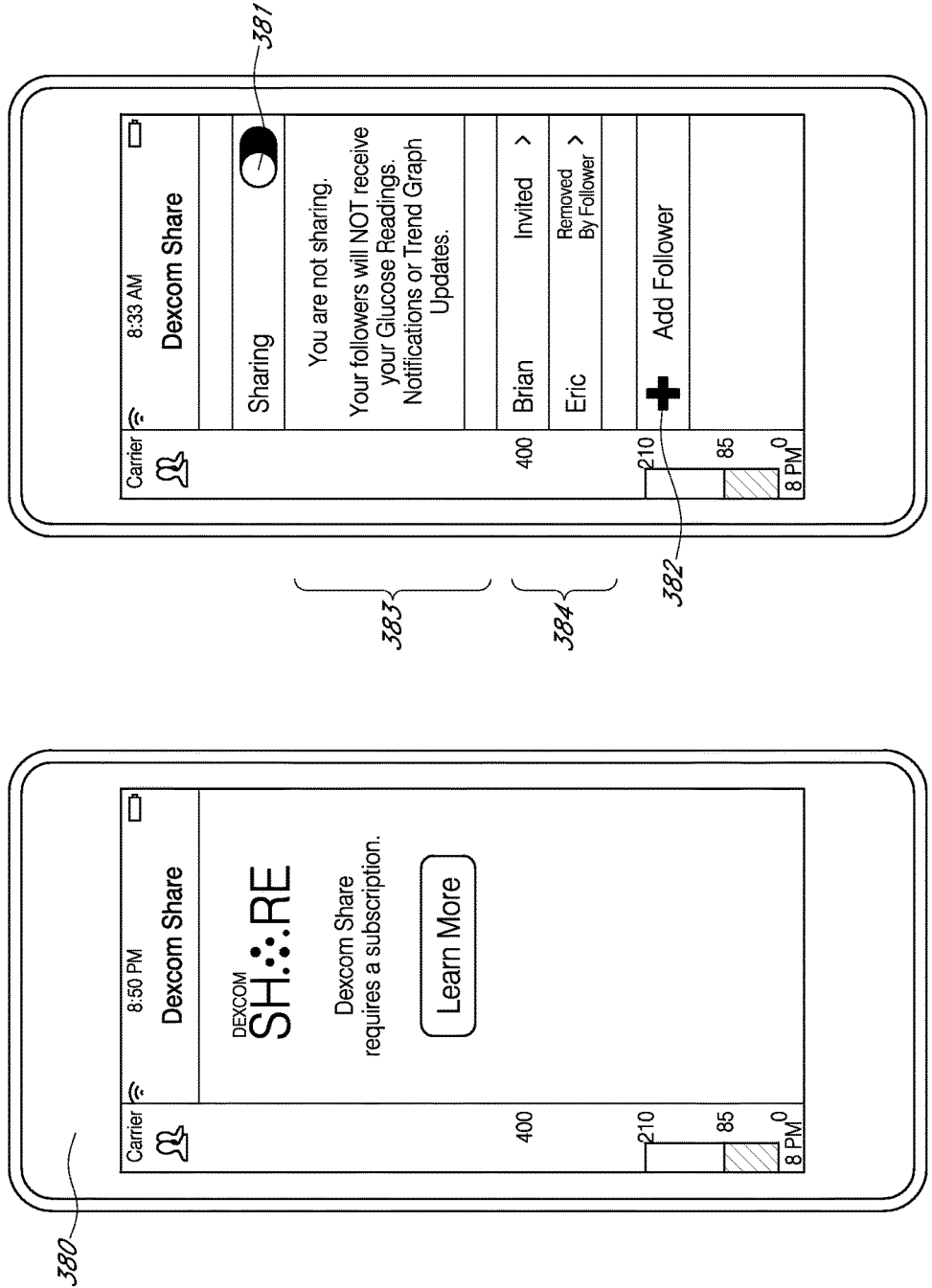
FIGS. 3D-3G illustrate user interfaces for adjusting remote monitoring settings in accordance with some exemplary implementations.
Figure 3E:
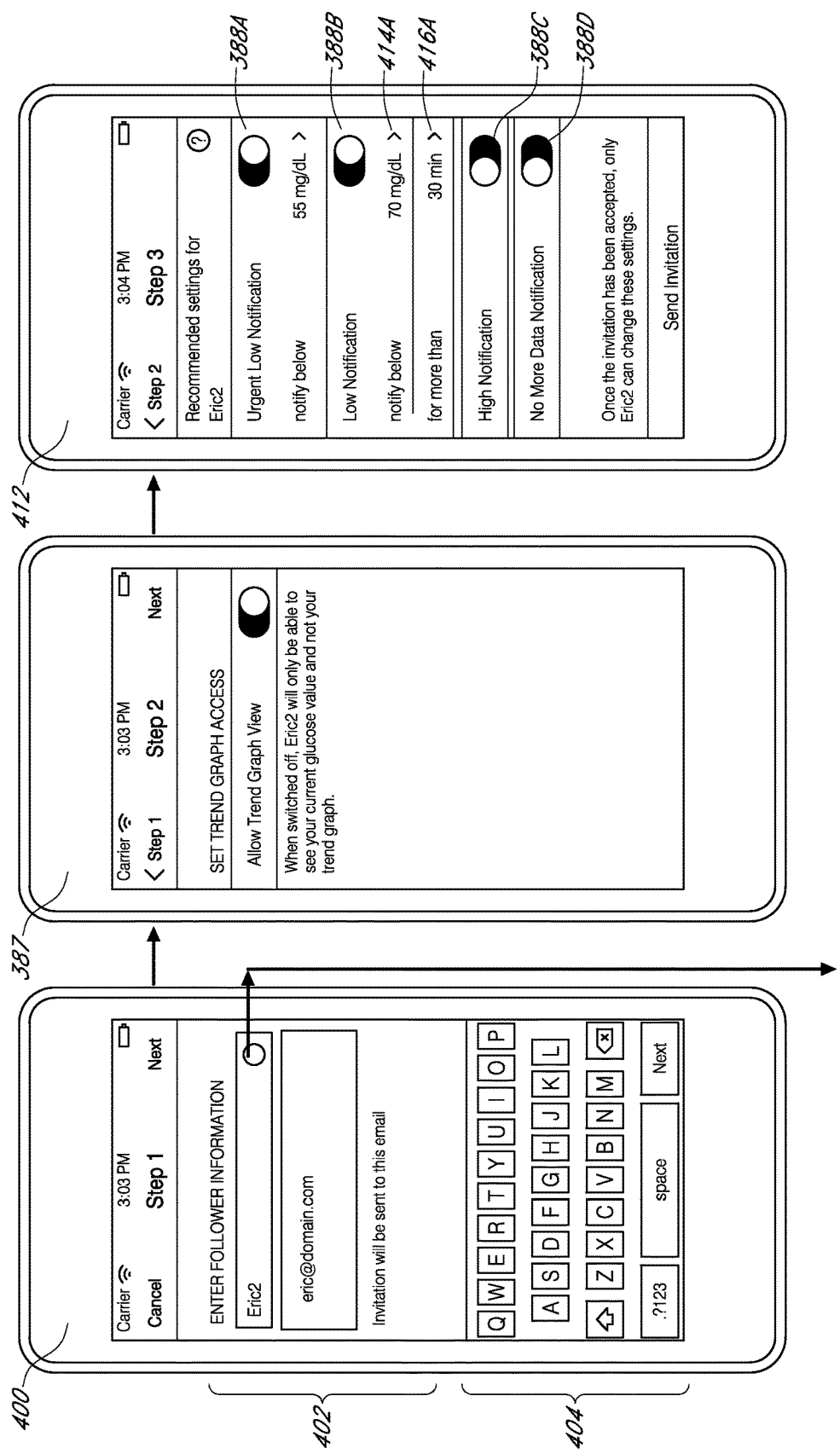
Figure 3F:
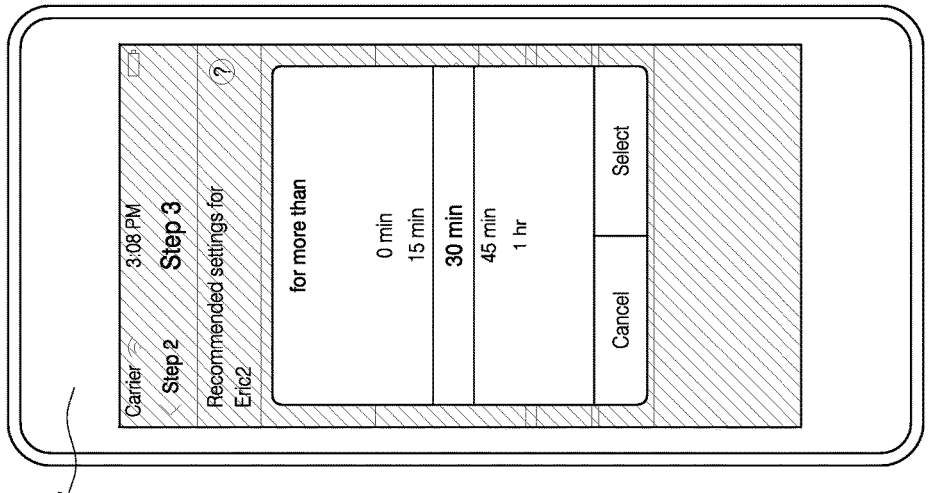
Figure 3F:
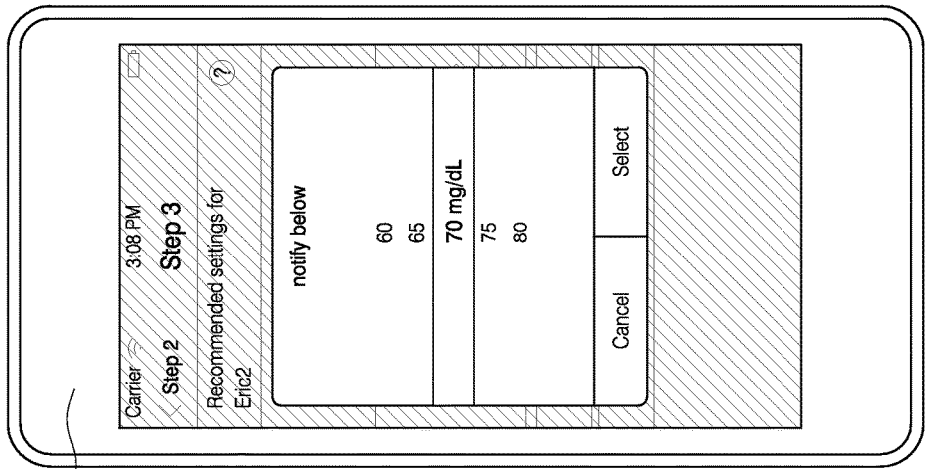
Figure 3G:
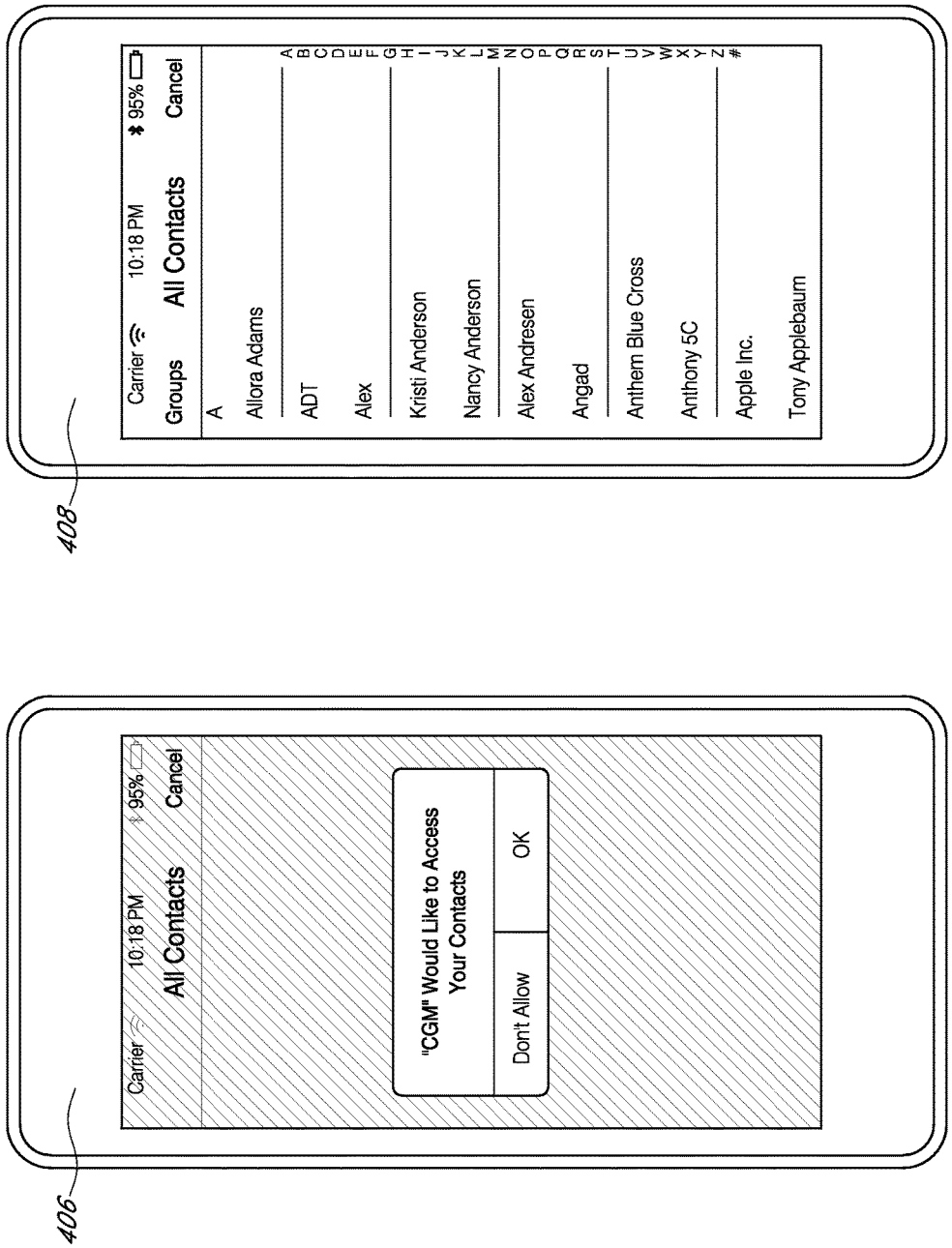

FIGS. 3D and 3E illustrate multiple interfaces for controlling data sharing settings. When sharing is enabled, a patient may allow one or more remote monitors to receive messages or alerts regarding the patient's glucose levels. Remote monitoring module 290 may display data sharing subscription screen 380 if a user has not subscribed to the remote monitoring service. The user may select the "Learn More" button to obtain additional information regarding this service. When the "Learn More" button is selected, the remote monitoring module 290 may launch and navigate a browser on device 18 to a website that provides additional information regarding the remote monitoring service. Alternatively or additionally, the remote monitoring module may connect to a server (e.g., server 230) to display this information directly within application 255. If, however, the user has subscribed to the remote monitoring service, remote monitoring module 290 may display data sharing screen 381. Message 383 may provide the user with a textual explanation about whether sharing is currently enabled and the type of data that may be viewed by the remote monitors. A patient may turn sharing on or off by toggling sharing button 381. Area 384 displays information regarding the user's remote monitors (e.g., identifier name and status indication) which may include invited remote monitors, removed remote monitors, and active remote monitors. A field may be associated with each remote monitor. When a particular field is selected, remote monitoring module 290 may navigate to a page that displays additional information regarding the selected remote monitor. The user may invite additional remote monitors by selecting button 382, which may initiate the remote monitor invitation process described below with respect to FIGS. 3E-3G.

FIGS. 3E-3H illustrates an exemplary workflow for the remote monitor invitation process and may begin when, for example, a user selects button 382 from data sharing screen 381. A user may enter remote monitor information using interface 400, as illustrated in the flow diagram of FIG. 3E. This information 402 may include, for example, the remote monitor's name and e-mail address. The system can send an invitation to the remote monitor using the entered e-mail address. The user may enter this information manually using keyboard 404. In some implementations, the user may add remote monitors from his or her contacts as illustrated in interfaces 406 and 408, which allows the application 255 to auto-populate the remote monitor's information.

The application 255 may allow the user to define the type of information that he or she wishes to share with remote monitors. For example, the user may use interface 387 to indicate whether the selected remote monitor has permission to see the user's glucose trend graphs. The user may use interface 412 to identify which alerts should be generated on secondary computing device 19. These alerts may include, for example, an urgent low notification 388A, a low notification 388B, a high notification 388C, and a no data notification 388D. The urgent low notification 388A and the low notification 388B may have certain threshold values 414A and 416A that define when an alarm is triggered. For example, Eric2 may receive a "Low Notification" alert when the user's glucose level is below 70 mg/dL for more than 30 minutes. The user may set threshold values 414A and 416A using interfaces 414B and 416B, respectively. A user may recommend different alert settings for each invited remote monitor during the invitation process described above with respect to FIG. 3E. The remote monitor may accept or modify these alert settings in some implementations.

Returning to FIG. 3A, icon 344 may be a reference calibration icon. When a calibration measurement is needed, calibration module 280 may display a badge on icon 344. In the implementation of FIG. 3A, the badge may include a circle with a number positioned over the calibration icon 344. This number may represent how many calibration readings are needed. For instance, during initialization or warm up of a new sensor system 8, two calibrations may be needed. In some implementations, a calibration measurement may be required at predetermined frequencies (e.g., every 12 hours) or when erratic glucose level readings are detected by sensor system 8. Erratic data may be caused by a faulty sensor, illness, interfering components in the patient's bodily fluid, or electrostatic interference with device electronics, for example.

Figure 3H:
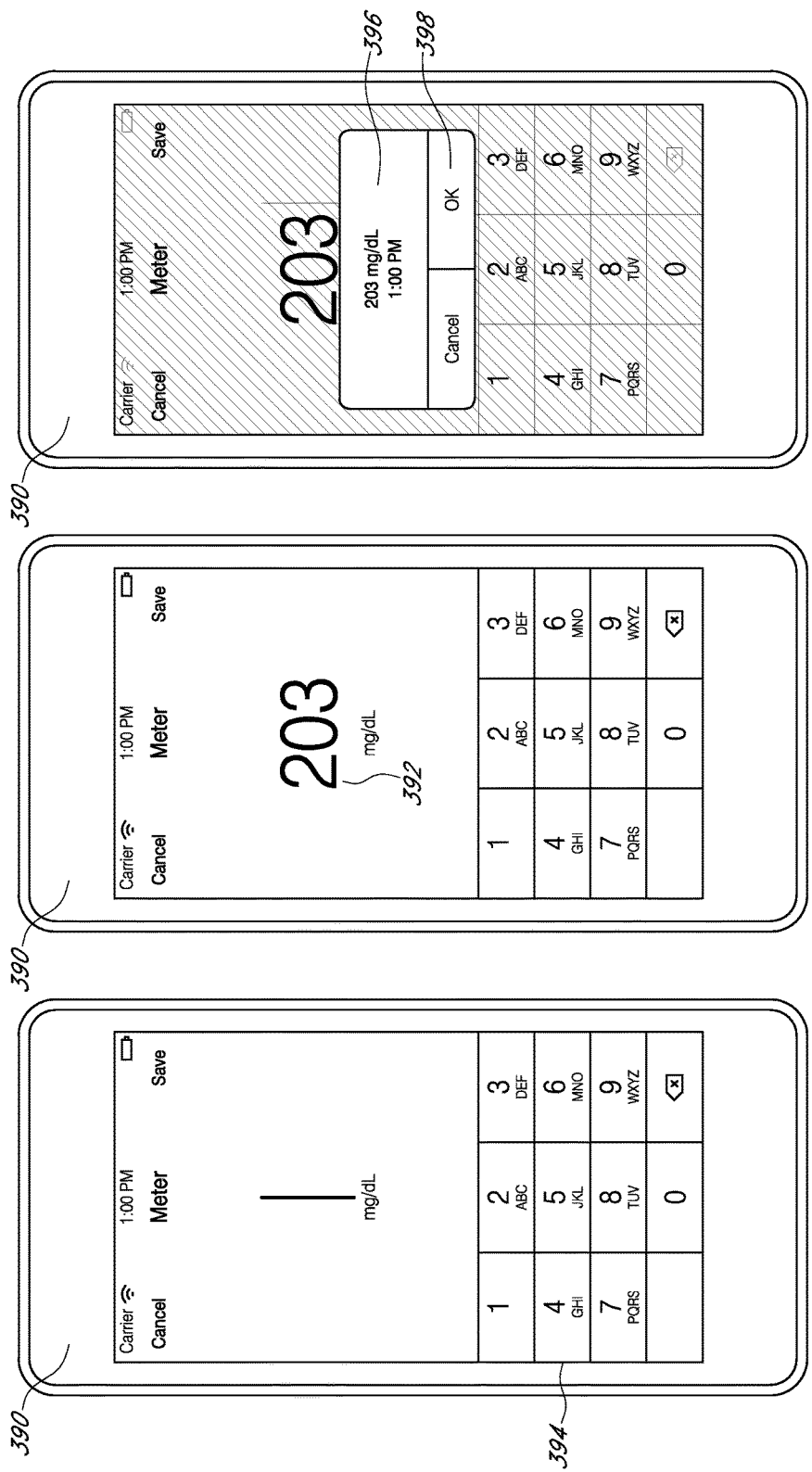
FIG. 3H illustrates user interfaces for calibrating a glucose monitor in accordance with some exemplary implementations.

FIG. 3H illustrates a user interface 390 for entering a calibration measurement. Calibration module 280 may display user interface 390 when a user selects calibration icon 344 of FIG. 3A, for example. A user may be prompted to measure his or her glucose level using an external blood glucose meter when a badge appears on icon 344. The user may enter measurement 392 into interface 390 using numerical keypad 394. Once the glucose measurement 392 is entered, interface 390 may prompt the user to confirm the value and time 396 of the reading using OK button 398. Once these values are confirmed, the application may initiate calibration of the system using the entered value.

Returning to FIG. 3A, icon 346 may be a menu icon. Selecting icon 346 may cause application 255 to display menu 360 illustrated in FIG. 3G. A user may use menu 360 to view or change various features of application 255. Menu 360 may include various submenus that allow a user to navigate to other screens and information. In the implementation of FIG. 3I, menu 360 includes the following submenus: Trend 361 which, when selected, causes application 255 to display home screen 310 illustrated in FIG. 3A; blood glucose meter 362 which, when selected, causes application 255 to display the blood glucose entry screens illustrated in FIG. 3H; alerts 363 which, when selected, causes application to display the alert setting screen 910 illustrated in FIG. 9B; transmitter information 364 which, when selected, causes application 255 to display a screen that contains information about the transmitter currently being used including, for example, the transmitter's serial number, activation date, battery level, expiration date, and pairing information (i.e., which devices the transmitter is currently paired with) as described below with respect to FIG. 3J; history 365 which, when selected, causes application 255 to display a log of past actions including, for example, triggered alerts, entered events, a sensor session start time, a sensor session stop time, share connectivity, and the like; reports 366 which, when selected, causes application 255 to display a screen that provides retrospective analysis of the user's data, including trend graphs comparing different timeframes of data and identification of patterns in selected timeframes of data; settings 367 which, when selected, causes application 255 to display information regarding how the application displays information (e.g., the height of the trend graph), user account information, and factory settings; and start session 369 which, when selected, causes application 255 to start a new sensor session if a sensor session is not already under way. With regard to button 369, if a session is currently under way, then a stop session option may appear which allows the user to end the current sensor session.

When transmitter button 364 is selected, application 255 may display exemplary interface 370 illustrated in FIG. 3H.

Interface 370 displays the transmitter ID 372 of sensor system 8, whether the transmitter is directly paired with the patient's glucose sensor 374, and a pairing button that a user may select to initiate pairing the transmitter with the current display device operating the application (e.g., device 18).

Returning to FIG. 3A, application 255 may display an icon on its user interfaces to indicate that the user's device is muted. Users may not understand that enabling a mute mode on a hand held computing device, such as smart phone 18, may prevent application 255 from generating audible alerts. Icon 347 may indicate whether a mute mode on computing device 18 is enabled or disabled (e.g. via a mute switch on the device). When the mute mode is enabled as illustrated in this figure, application 255 may be unable to generate any audible alerts on device 18.

Figure 4A:
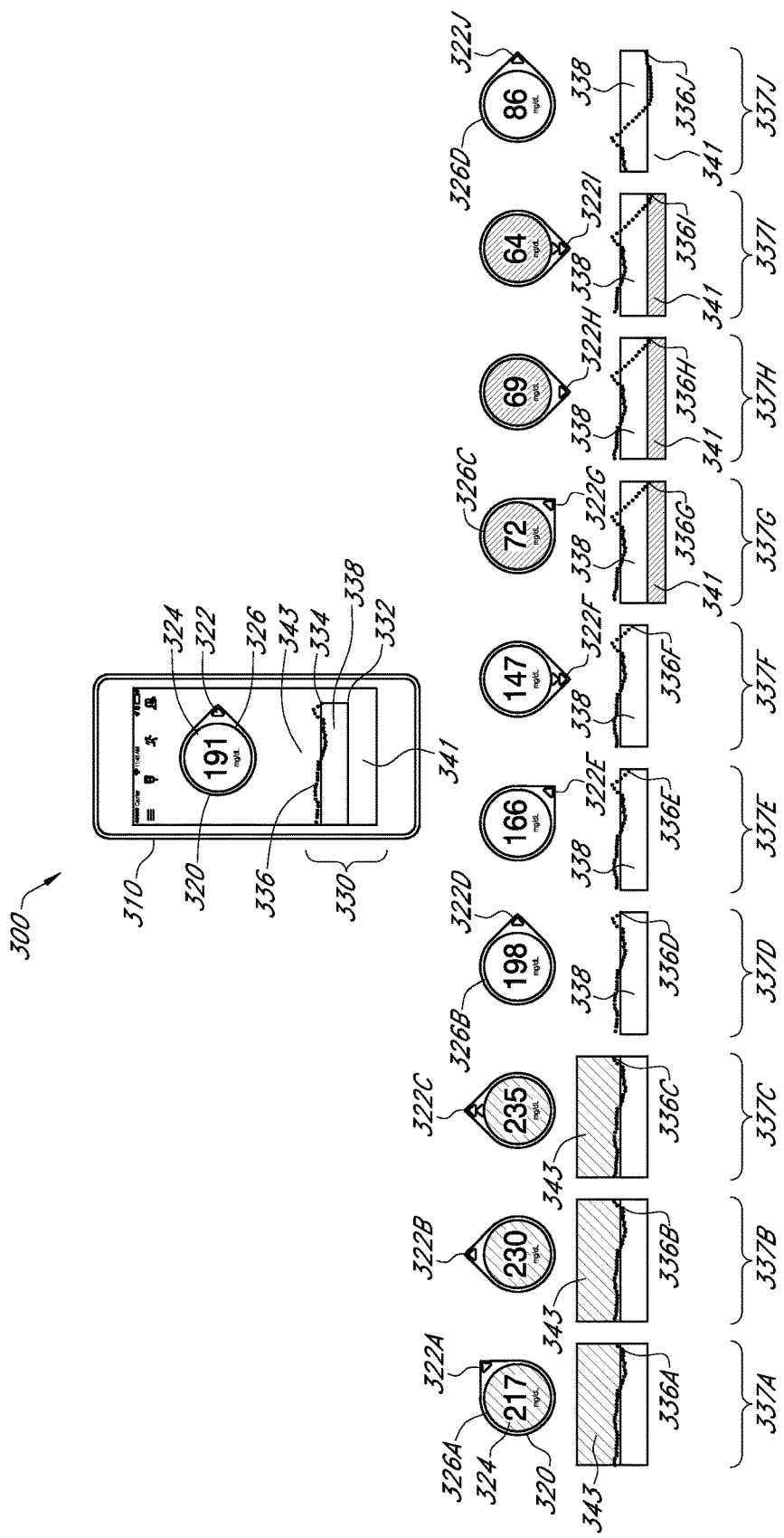
FIGS. 4A and 4B illustrate various views of a user interface for providing glucose level information in accordance with some exemplary implementations.

FIG. 4A illustrates an exemplary user interface 300 that provides a patient's glucose level information. Data review module 264 may change the information displayed in user interface 300 based on measurements received from sensor system 8. For example, data review module 264 may shows different representations 337A, 337B, 337C, 337D, 337E, 337F, 337G, 337H, 337I, and 337J of home screen 310 as the patent's glucose level changes over a period of time. A patient may quickly and discreetly ascertain his or her current glucose level, the rate of change of the current glucose level, and risk status from user interface 300. Interface 300 may be displayed on the patient's hand held computing device 18 as well as on remote monitor devices 19. User interface 300 may have a home screen 310 that includes a unitary icon 320 and a graph 330. Graph 330 may display the patient's glucose levels over a predetermined period of time.

A user, such as the patient or remote monitor, may quickly assess the patient's current glucose value, its rate of change, and the patient's state by looking at unitary icon 320. Unitary icon 320 may be substantially circular in shape and may display a numerical indicator 324 that corresponds to the patient's current glucose value. Unitary icon 320 may also include one or more arrows that indicate whether the patient's current glucose value is increasing, decreasing, or stable (i.e., the rate of change). Background color 326 may change to indicate a patient's glycemic state, such as whether the patient's current glucose level is low (e.g., hypoglycemic), in target, or high (e.g., hyperglycemic) relative to various threshold values. These threshold values may be provided by a user or as default values by application 255.

Background 326 may dynamically change based on a determined clinical state of the user. For example, the background color 326 may be a first color when the patient's current glucose level is high (e.g., greater than or equal to an upper threshold level 334, such as 210 mg/dL), a second color when the patient's current glucose level is in a target zone (e.g., between a lower threshold level 332 and an upper threshold level 334, such as between 80 and 210 mg/dL), and a third color when the patient's current glucose level is low (e.g., less than or equal to a lower threshold level 332, such as 80 mg/dL). In the implementation of FIG. 4A, the first color may be yellow (as illustrated at 326A), the second color may be gray (as illustrated at 326B), and the third color may be red (as illustrated at 326C). In some implementations, different colors, patterns, or textures (e.g., a dotted or crosshatched background) may be used alone or in combination in unitary icon 320 to illustrate the patient's current glucose level.

Unitary icon 320 may also visually change based on a current, determined rate of change of the user's glucose level. For example, the unitary icon may have a rate of change indicator 322 that points in different directions as it rotates about the perimeter of the unitary icon, as illustrated in FIG. 4A. The direction in which indicator 322 points may represent a calculated rate of change of the patient's current glucose level. This rate of change may be based on current and historical glucose measurements received from sensor system 8. In some implementations, the direction in which indicator 322 points may be represented by a numerical degree value. Moving clockwise around the perimeter of unitary icon 320, indicator 322 may point north towards the top of user interface 300 (corresponding to a 0° pointing direction), east towards the right side of the user interface (corresponding to a 90° pointing direction), south towards the bottom of the user interface (corresponding to a 180° pointing direction), and west towards the left side of the user interface (corresponding to a 270° pointing direction). It is understood that the aforementioned degree values are exemplary, and that the pointing direction may be between 0° and 359°. For example, indicator 322 may have a pointing direction of 45° when it points in a northeast direction.

The indicator 322 may point north or northeast (i.e., have a pointing direction between 0° and 90°) as illustrated at 322A, 322B, and 322C when the patient's glucose level is increasing. In these cases, the patient's glucose level may experience a positive rate of change at the current point in time.

The indicator 322 may point east (i.e., have a pointing direction of 90°) as illustrated at 322J when the patient's glucose level is stable. In some implementations, indicator 322 may point west (i.e., have a pointing direction of 270°) or omitted altogether from unitary icon 320 when the patient's glucose level is stable.

The indicator 322 may point south (i.e., have a pointing direction of 180°) or southeast (i.e., have a pointing direction between 90° and 180°) as illustrated at 322E, 322F, 322G, 322H, and 322I when the patient's glucose level is decreasing.

The indicator 322 may include one or more arrows or triangles to indicate how quickly a patient's glucose level is increasing or decreasing. For example, indicator 322C may include two arrows that point north (i.e., at a 0° pointing direction) to indicate that the glucose level is increasing rapidly. In another example, indicators 322F and 322I may include two arrows that point south (i.e., at a 180° pointing direction) to indicate that the glucose level is decreasing rapidly. The number of arrows in arrow indicator 322 may vary based on the magnitude of the rate of change.

Data review module 264 may compare the calculated rate of change to one or more predetermined ranges to determine the direction in which indicator 322 points and the number of indicators to display. These predetermined ranges may be automatically set as default values or manually set by an administrator or the patient. For illustrative purposes, the following examples describe how data review module 264 may make these determinations:

If the rate of change of the current glucose value is between −0.5 and 0.5, then indicator 322 may point east or west (i.e., have a pointing direction of approximately 90° or 270°, respectively) with one arrow to indicate that the rate of change is stable. In some implementations, indicator 322 may be absent.

If the rate of change of the current glucose value is between 0.6 and 1.5, then indicator 322 may point northeast (i.e., have a pointing direction of approximately 0°-90°) with one arrow to indicate that the rate of change is increasing.

If the rate of change of the current glucose value is between 1.6 and 2.5, then indicator 322 may point north (i.e., have a pointing direction of approximately) 0° with one arrow to indicate that the rate of change is increasing.

If the rate of change of the current glucose value is greater than 2.5, then indicator 322 may point north (i.e., have a pointing direction of approximately) 0° with two arrows to indicate that the rate of change is increasing rapidly.

If the rate of change of the current glucose value is between −1.5 and −0.5, then indicator 322 may point southeast (i.e., have a pointing direction of approximately 90°-180°) with one arrow to indicate that the rate of change is decreasing.

If the rate of change of the current glucose value is between −1.6 and −2.5, then indicator 322 may point south (i.e., have a pointing direction of approximately) 180° with one arrow to indicate that the rate of change is decreasing.

If the rate of change of the current glucose value is less than −2.5, then indicator 322 may point south (i.e., have a pointing direction of approximately) 180° with two arrows to indicate that the rate of change is decreasing rapidly.

A patient or remote monitor may only have a brief amount of time to glance at home screen 310 to check the patient's glucose levels. In some situations, the patient may want to check his or her glucose levels discreetly without attracting the attention of others. Having easily identifiable indicators of the patient's glucose level and clinical risk may be beneficial. In some implementations, data review module 264 may incorporate different visual elements into trend graph 330 and unitary icon 320 to represent the patient's current glycemic state. These visual elements may include different colors, textures, patterns, and the like. The strategic use of these visual elements may also allow the patient or remote monitor to quickly assess the patient's glucose levels and determine whether medical attention is needed at a glance.

The use of these visual elements may be incorporated into trend graph 330 of FIG. 4A, for example. Graph 330 may include a trend line 336 that shows how a patient's glucose level changes over a predetermined period of time. The current glucose level may be displayed as the right-most data point on graph 330. The current glucose level may correspond to the user's glucose level at the present time or the most recently received glucose level. Graph 330 may include one or more horizontal bands, such as a first band 343, a second band 338, and a third band 341. The bands may be defined by high and low threshold values which are illustrated as horizontal lines 334 and 332, respectively. These threshold values may be visually distinct from one another. For example, graph 330 may include an upper threshold value 334 in a first color (e.g., yellow), and a lower threshold value 332 in a different second color (e.g., red). The upper threshold value 334 may be 210 mg/dL of glucose, and the lower threshold value 332 may be 85 mg/dL of glucose, for example. However, any value may be chosen by a user, as discussed further herein. For illustrative purposes only, glucose levels greater than or equal to the upper threshold value 334 (i.e., within band 343) may be interpreted as high glucose levels; glucose levels less than or equal to the lower threshold value 332 (i.e., within band 341) may be interpreted as low glucose levels; and glucose levels between the lower threshold value 332 and upper threshold value 334 (i.e., within band 338) may be interpreted as target glucose levels.

Bands 343, 338, and 341 may represent different ranges of glucose levels. In order to distinguish one band from another, bands 343, 338, and 341 may be visually different. In some embodiments, each band may be shaded with a different color or colors. Other forms of visual distinction may also be used including the use of different textures or patterns as described above. The use of different visual elements may facilitate quick visual recognition of whether a patient's most recently measured glucose level is high, in target, or low.

In the implementation of FIG. 4A, for example, when the patient's current glucose level is in target, then bands 343 and 341 may be white or void of color, and band 338 may be gray. When the patient's current glucose level exceeds the high threshold 334, then band 343 may changes colors, such as from white to yellow. When the patient's current glucose level falls below the low threshold 332, then band 341 may change colors, such as from white to red. Note, in this implementation, the in-target band 338 remains the same color (e.g., gray) whether or not the current glucose data point falls inside or outside of the in-target range.

The use of different visual elements may also be incorporated into unitary icon 320 in some implementations. Like the bands in trend graph 330, the background color 326 of unitary icon 320 may correspondingly change depending on whether the patient's current glucose level is high, in target, or low in the implementation of FIG. 4A. As illustrated, background color 326 may match the color of the band that the current glucose value falls in. For example, when the patient's current glucose level is high (i.e., within band 343), then background color 326 of unitary icon 320 may match the color of band 343. If, for example, band 343 is yellow, then background color 326 may also be yellow. In another example, when the patient's current glucose level is in target (i.e., within band 338), then background color 326 may match the color of band 338 (e.g., gray). In yet another example, when the patient's current glucose level is low (i.e., within band 341), then background color 326 may match the color of band 341 (e.g., red).

Trend line 336 may include a plurality of glucose value markers or glucose data points. Each data point may correspond to a particular glucose level measured at a particular time. These data points may be represented differently depending on the band in which the data point falls and/or whether the data point is the current data point.

As an example, data points within a particular band may be the same color as all other data points within that band. That is, all data points in the same band are colored the same but are colored differently than data points falling within one or more other bands. For example, data points falling within band 341 are colored differently than data points falling within bands 338 and 343. However, data points falling within band 338 can be colored the same.

In some implementations, the color of a data point may depend upon the band in which the current data point lies. In these implementations, the color of the data points within a particular band may change depending on whether the current data point also falls within the same band. For example, as illustrated in the implementation of screen 337J, data points in band 341 may be a first color or shade when the current data point is in a different band (i.e., band 338). However, if the current data point is also in band 341, then the data points in this band may change colors or shades from the first color or shade to a second color or shade as illustrated in the implementations of screens 336G-336I.

While data points may change colors or shades depending on whether they lie in the same band as the current data point, this change may only occur in certain bands, in accordance with some implementations. For example, this change may only occur for data points having a value that is less than lower threshold value 332 (i.e., within band 341) but may not apply to in-target data points (i.e., within band 338) or data points having a value greater than the upper threshold value 334 (i.e., within band 343). This implementation can be beneficial to a user as it allows the user to differentiate a critical low glucose level from a less dangerous in target or high glucose level.

In some implementations, the data point corresponding to the current glucose measurement may have its own unique visual representation that is different from all other data points on trend graph 330. For example, while data points lying within the same band as the current data point may have the same color, the current data point may be a different color and/or may be presented differently. For example, a border may be drawn around the current data point. In another example, the current data point may be represented using a different shape (e.g., a star) instead of the circular dots used for the other data points.

In some implementations, the colors of the data points may be chosen to provide visual contrast from the color of the bands. This may be a particular problem if, for example, a white data point is located within a yellow band. In these situations, data review module 264 may change the color of the data point from white to black, for example, when a band is changed to yellow so that the black data point stands out against the yellow band.

FIG. 4A shows different representations 337A, 337B, 337C, 337D, 337E, 337F, 337G, 337H, 337I, and 337J of home screen 310 over a period of time. The view on the left side of FIG. 3A may correspond to the earliest point in time. The view on the right side of FIG. 3A may correspond to the latest point in time (e.g., the current time or the most recent point in time). Intermediate views may represent intermediate points in time.

In views 337A, 337B, and 337C the patient's current glucose level is high (i.e., the current data point falls within band 343). The color of band 343 (e.g., yellow) matches the background color 326A of unitary icon 320. Indicators 322A, 322B, and 322C point north (i.e., have a pointing direction of approximately 0°) or northeast (i.e., have a pointing direction of approximately 0°-90°) to represent a positive rate of change in the patient's current glucose level.

In views 337D, 337E, and 337F the patient's current glucose levels is within target (i.e., within band 338). Consequently, the color of band 338 (e.g., gray) matches the background color 326B of the unitary icon. Although the patient's current glucose level is within target in views 337D, 337E, and 337F, the rate of change in each view is different as indicated by indicators 322D, 322E, and 322F.

For example, indicator 322D points east (i.e., have a pointing direction of approximately 90°) to indicate that there is no substantial change in the patient's glucose level over time. Because the patient's current glucose level is within target and the rate of change is stable, the patient's glucose level remains steady. Indicators 322E and 322F, however, point southeast (i.e., have a pointing direction of approximately 90°-180°) and south (i.e., have a pointing direction of 180°), respectively, to indicate that the rate of change of the current glucose level is decreasing. The presence of two downward pointing triangles in indicator 322F indicates that the rate of change is decreasing rapidly (i.e., has a large magnitude) in view 337F.

In views 337G, 337H, and 337I, the patient's current glucose levels is low (i.e., within band 341). Consequently, the color of band 341 (e.g., red) matches the background color 326C of the unitary icon. As trend lines 336G, 336H, and 336I move from band 338 into the band 341 (i.e., from target glucose levels to low glucose levels), the indicator points in different directions to indicate how quickly the patient's glucose level is decreasing. For example, indicators 322G, 322H, and 322I move from pointing southeast (as illustrated at 322G) (i.e., have a pointing direction of approximately 90°-180°) to pointing south (as illustrated at 322H) (i.e., have a pointing direction of approximately 180°). If the patient's glucose level is decreasing rapidly (i.e., has a large rate of change magnitude), then two arrows are used as illustrated in indicator 322I.

In view 337J, trend line 336J rises within band 341 to band 338 (i.e., from a low glucose level to a target glucose level). As the current glucose level is in the target range (i.e., within band 338), the background color 326D of the unitary icon 320 matches the band's color (e.g., gray). The indicator 322J points east (i.e., have a pointing direction of approximately 90°) to indicate that the rate of change of the patient's glucose level is relatively stable, and that the patient's current glucose level is not likely to change.

Figure 4B:
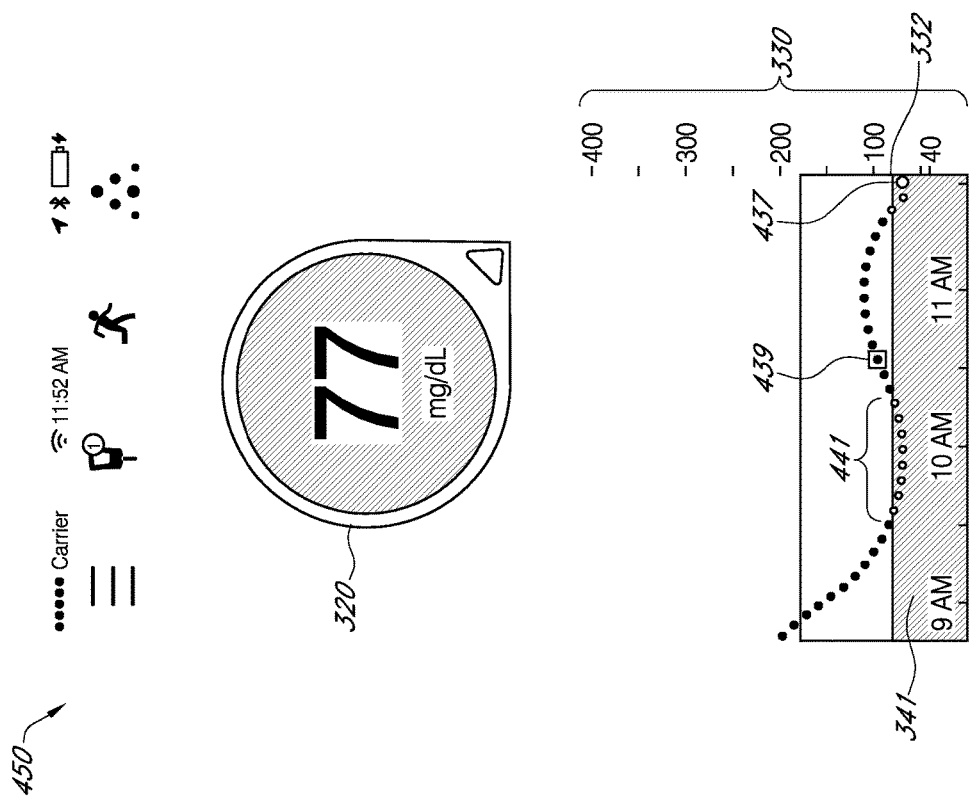
Figure 5A:
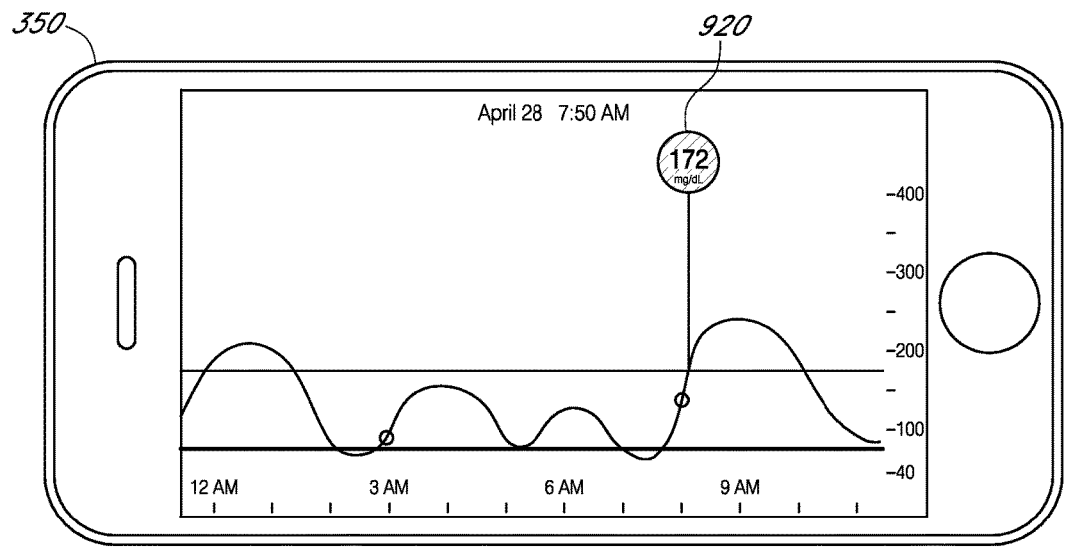
FIGS. 5A-5D illustrate various views of a user interface in reflection mode in accordance with some exemplary implementations.
Figure 5B:
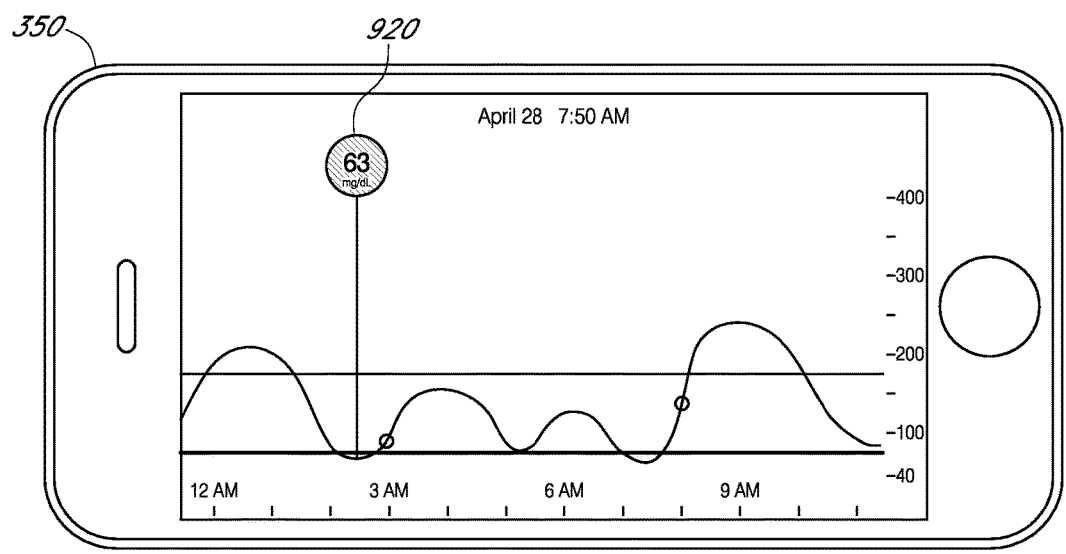
Figure 5C:
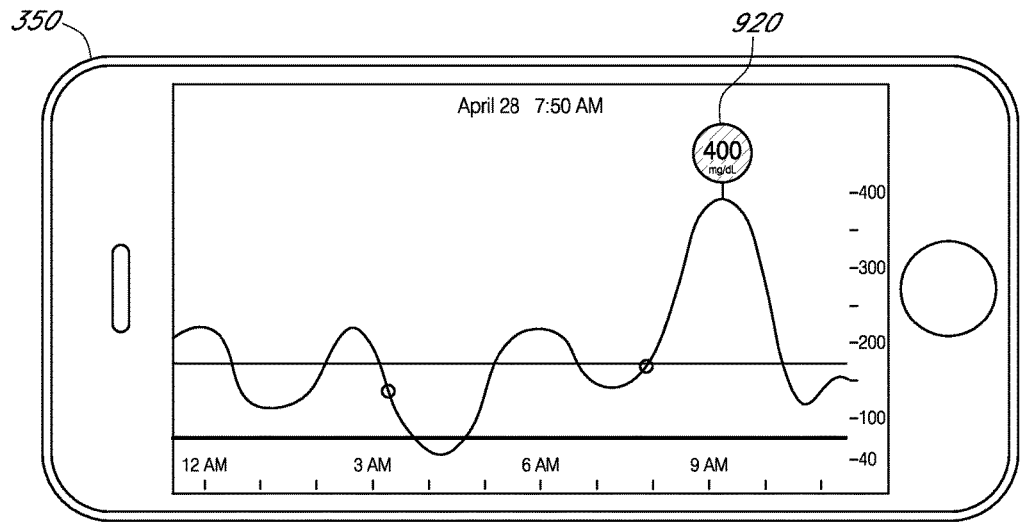
Figure 5D:
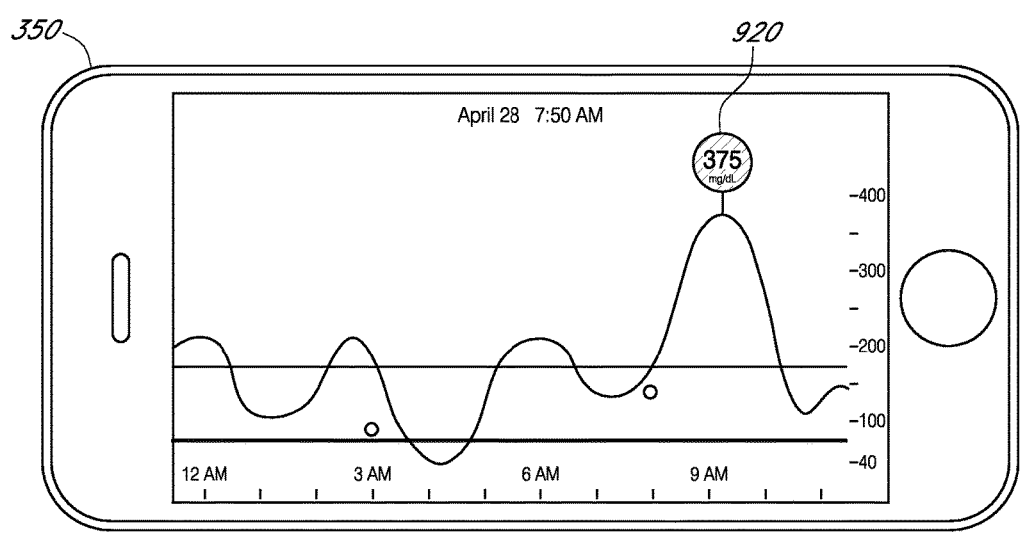

FIG. 4B illustrates another view 450 of user interface 300 that includes a unitary icon 320 and a trend graph 330. Unitary icon 320 indicates that the current or most recently received glucose level is 77 mg/dL. This current glucose value may correspond to data point 437 on the right-most side of trend graph 330. Data point 437 may be less than lower threshold level 332, may lie in band 341, and may correspond to a low glucose value. In order to indicate that the patient's current or most recent glucose value is low, data review module 264 may shade band 341 and the background color of unitary icon 320 with a red color to indicate that the patient may require attention. Data points above trend line 332 may be black, and data points 441 and 437 below trend line 332 may be white. The change in data point color from black to white may provide higher visual contrast between the data points and the color of the band. In addition, this change in color may allow a user to quickly determine how long the patient's glucose values have been low. In addition to using different colors to distinguish data points in different bands, data review module 264 may also use different graphics, shapes, sizes, and the like.

The current data point 437 may also be illustrated differently than older data points using different data point types. Doing so allows a user to quickly distinguish the current reading from historical readings. Data point 437 may be a circle having a black border and color background fill. The color of the background fill may be white because data point 437 lies below threshold value 332. Previous or historical glucose level readings may be illustrated using solid circles. The color of the circles may be white or black depending on whether the data point lies above or below threshold value 332 as described above.

Events may also be illustrated different than other data points. In some implementations, an event marker may be placed around the data point that is closest in time to the event. Quick identification of events from a trend graph 330 may allow a patient or remote monitor to discern whether an event may have influenced the patient's glucose levels. An event may be associated with the data point recorded at the time closest to when the event took place. In graph 330, data point 439 may be associated with an event. If, for example, the patient consumed a beverage or administered a bolus of insulin and recorded this event using interface 1610, then a box may appear around the data point closest to the recorded event. In this implementation, the box has a black border with a white background although other colors, shapes, patterns, and textures may be used.

FIGS. 5A, 5B, 5C, and 5D illustrate another view 350 (e.g., 350 in FIG. 5A) of a user interface. View 350 may provide detailed information regarding a patient's glucose level history and may correspond to a reflection mode. Data review module 264 may enter reflection mode when computing device 18 and/or 19 detects that it has been rotated from a portrait orientation into a landscape orientation based on an accelerometer input or the like.

FIGS. 5A, 5B, 5C, and 5D display various views of a trend graph as a user interacts with the user interface. Time may be shown on the horizontal axis, and the glucose level may be illustrated on the vertical axis. These trend graphs may be similar to the trend graphs described above with respect to FIG. 4A but may be extended over a different period of time (e.g., a longer or a shorter period of time). The implementation of FIGS. 5A, 5B, 5C, and 5D shows glucose levels over a default, twelve-hour period. Like the trend graphs of FIGS. 4A and 4B, the current or most recent glucose level reading may be shown on the right. Data points to the left of the current data point may represent earlier readings. These trend graphs may include horizontal lines that represent the lower and higher threshold values described above.

When a user hovers over or selects a data point, a miniature icon 920 may appear above the data point nearest to the user's point of interaction with the user interface (e.g., the data point closest to the detected position of the user's finger, stylus, mouse, etc.). The miniature icon 920 may display a numerical value corresponding to the glucose level at the day and time displayed at the top of the graph. This day and time may be associated with the data point nearest to the user's point of interaction with the user interface. The miniature icon 920 may have a background color or fill to indicate whether the glucose level at that data point was low, in target, or high as described above with respect to FIG. 4A. As a user traces his or her pointing device (e.g., finger, mouse, stylus, and the like) along the trend graphs illustrated in FIGS. 5A, 5B, 5C, and 5D, a miniature icon 920 may appear at each data point. Although miniature icon 920 in FIGS. 5A, 5B, 5C, and 5D do not include a rate of change indicator, this indicator may be included with the miniature icon to represent the rate of change at that point in time in some implementations.

Figure 6A:
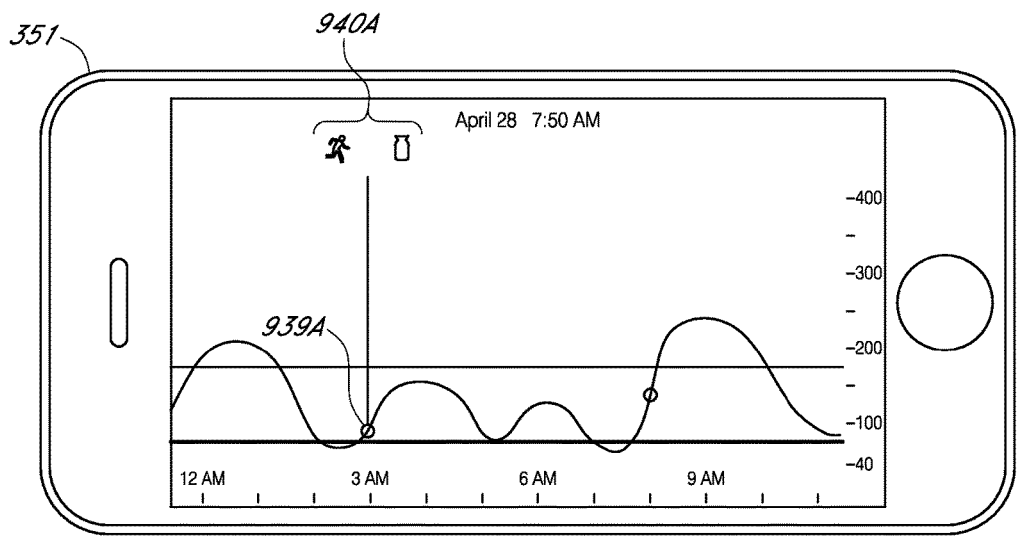
FIGS. 6A-6C illustrate various views of a user interface in reflection mode in accordance with some exemplary implementations.
Figure 6B:
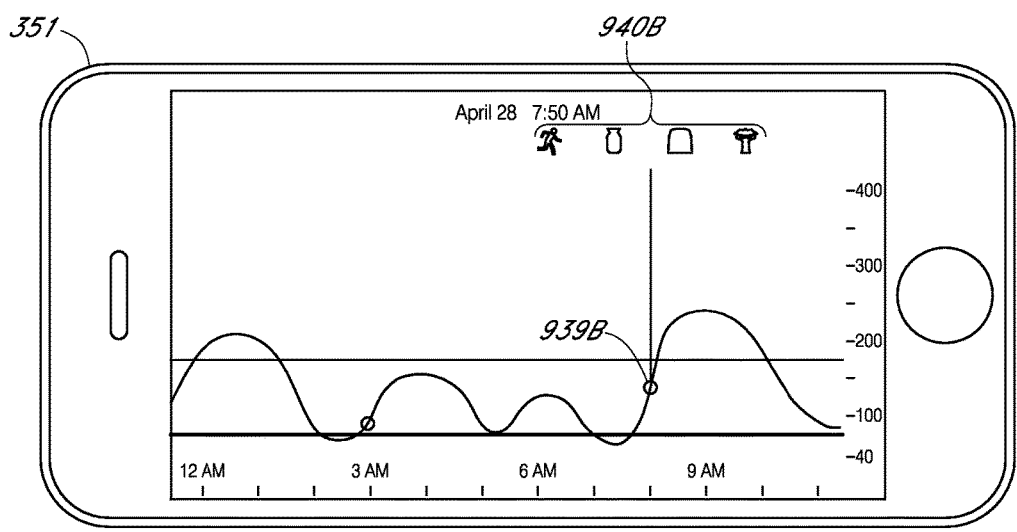
Figure 6C:
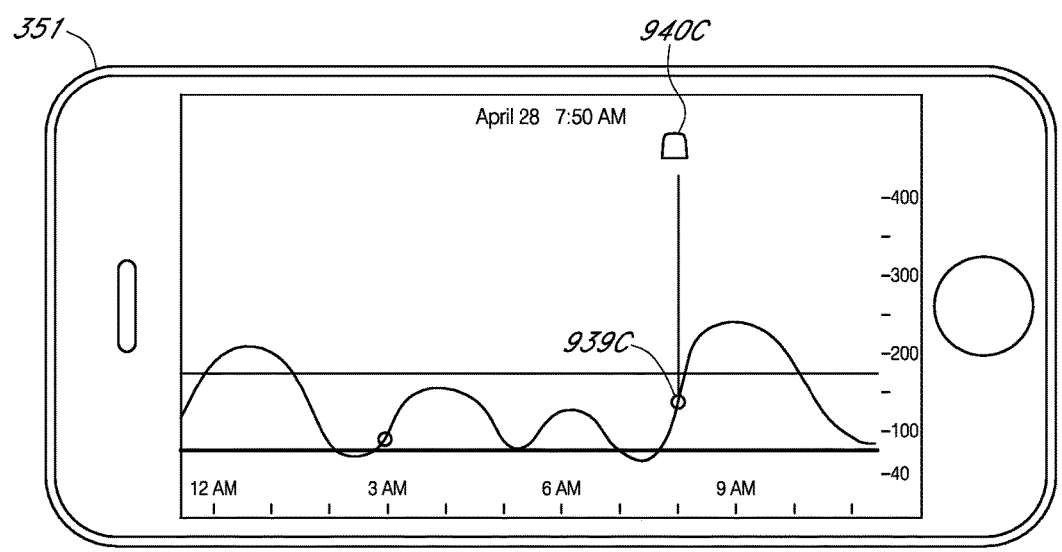
Figure 7A:
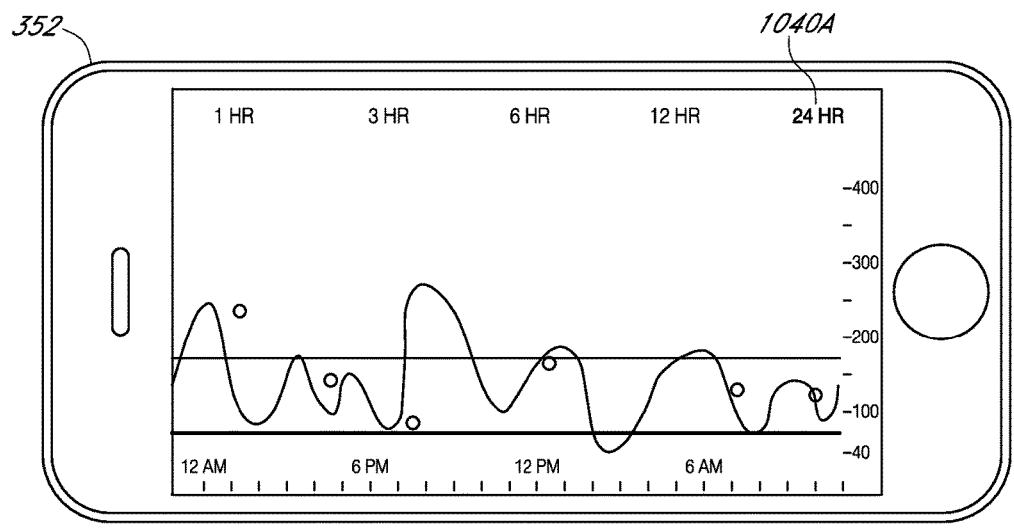
FIGS. 7A-7E illustrate various views of a user interface in reflection mode in accordance with some exemplary implementations.
Figure 7B:
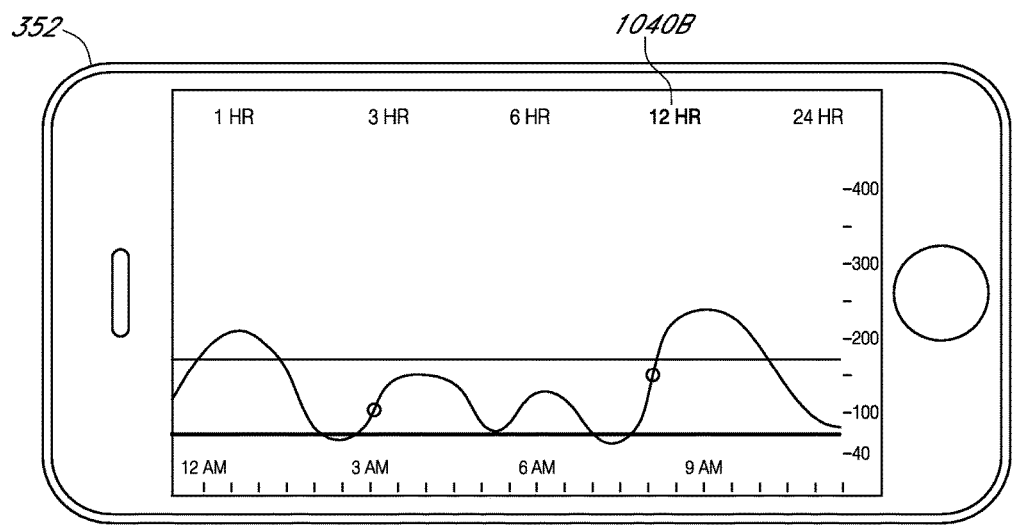
Figure 7C:
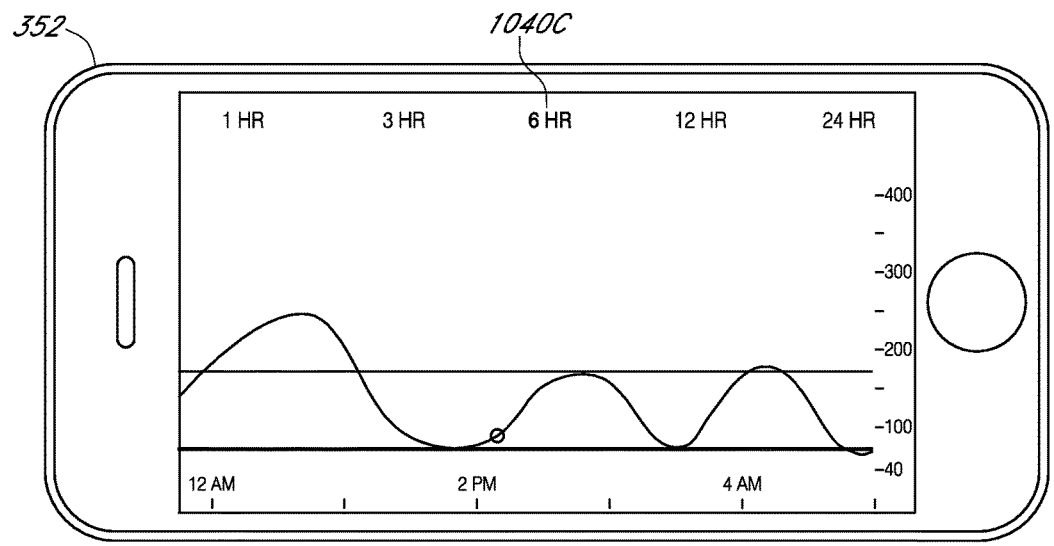
Figure 7D:
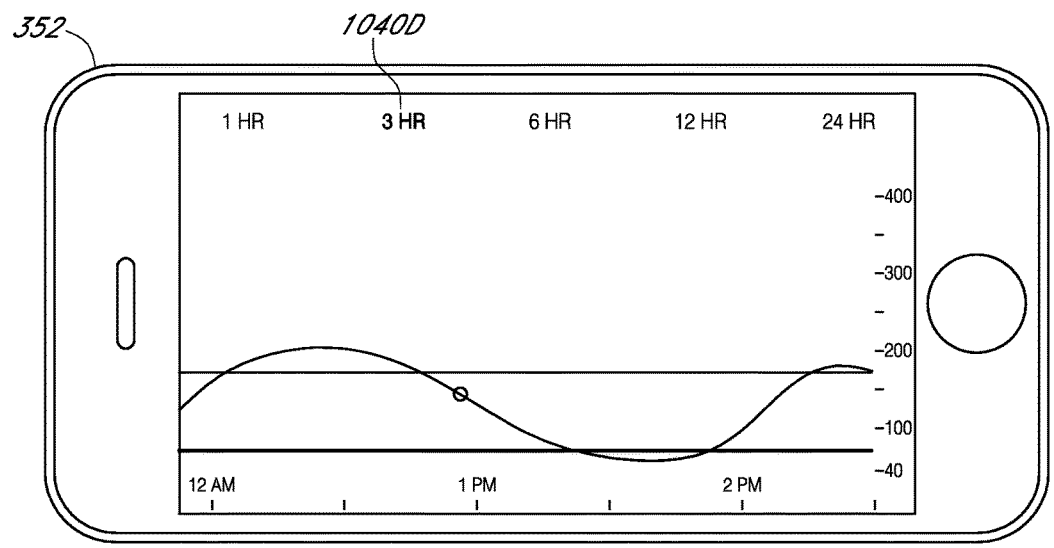
Figure 7E:
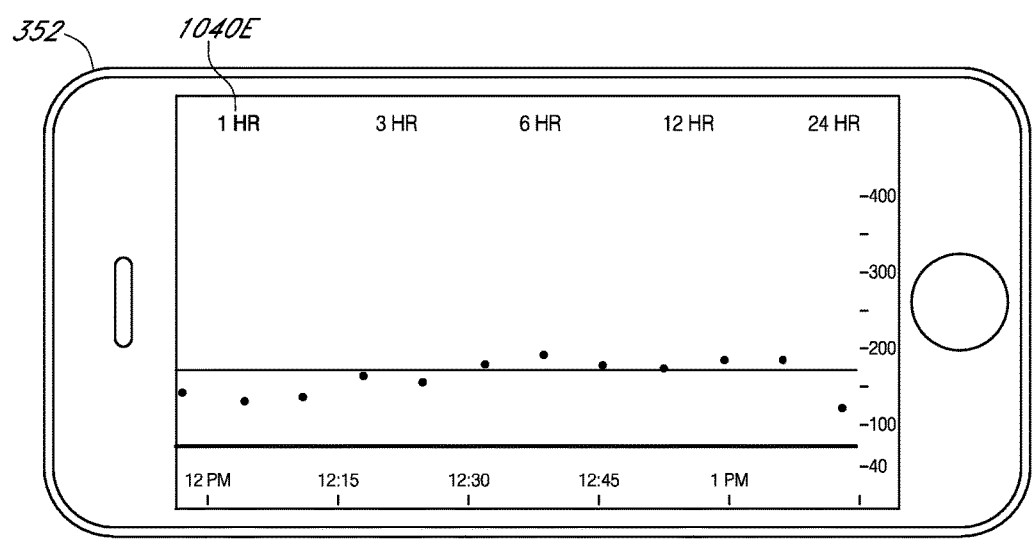

FIGS. 6A, 6B, and 6C illustrate additional views 351 of a user interface in a reflection mode as the user interacts with event information displayed on the user interface. Data review module 264 may generate views 351 when computing device 18 and/or 19 detects that it has been rotated into a horizontal position. This detection may be based on input from an accelerometer within computing device 18 and/or 19, for example. The trend graphs in these views may include data points associated with events 939A, 939B, and 939C. Data points associated with events may be illustrated differently than other data points, as described above. In the implementation of FIGS. 6A, 6B, and 6C, data points 939A, 939B, and 939C may be illustrated with white boxes, and non-event data points may be illustrated with solid black circles. Different colors, shapes, patterns, textures, sizes of data points, and the like may be used to distinguish data points associated with events from other data points. When data points 939A, 939B, or 939C are selected, icons 940A, 940B, or 940C may appear. These icons may indicate the type of activities associated with the events (e.g., a calibration event, food intake, and the like). Additional information regarding these activities or events may be displayed by selecting icons 940A, 940B, and 940C, including, for example, the time of the event, any corresponding amount (e.g., calories consumed), and the like.

FIGS. 7A, 7B, 7C, 7D, and 7E illustrate additional views 352 of a user interface in a reflection mode. Data review module 264 may generate views 352 when computing device 18 and/or 19 is rotated from a portrait orientation into a landscape orientation or held in the landscape orientation. Views 352 may include trend graphs that span different lengths of time. For example, in views 350 and 351 of FIGS. 5A-5D and 6A-6C, respectively, the trend graphs display glucose level data over a 12-hour period of time. If a user wishes to see more data (e.g., over a 24 hour period of time) or less data (e.g., over a 3 hour period of time) on the trend graph, the user may change the amount of data that is displayed using view 352. In view 352, one or more selectable timeframe icons (1 HR, 3 HR, 6 HR, 12 HR, and 24 HR) may be displayed at the top of the view. A user may select the desired timeframe icon to indicate the amount of data that he/she wishes to see. These timeframe icons may appear when a user is not interacting with the screen (e.g., computing device 18 and/or 19 does not detect any user input including the presence of a touch or selection). Other actions, such as hand gestures, may also be used to increase or decrease the timeframe (e.g., swiping, pinching, and stretching the display on devices 18 and/or 19). These hour designations are merely exemplary and other increments may be used. The current time may be displayed on the right side of each trend graph. As the time period increases, more data points may be displayed, and the trend line may resemble a continuous line. As the time period decreases, fewer data points may be displayed, and the individual data points may become more discernible because data points are generated at regular intervals, such as every five minutes. Allowing the user to adjust the time scale and, consequently, the amount of data that is displayed may help the user detect trends in the patient's glucose levels.

The application 255 running on hand held computing devices 18 and/or 19 may provide a snapshot of the patient's current and previous glucose levels. In some implementations, the application may also indicate whether the patient is at risk in the near future of becoming hypoglycemic or hyperglycemic. Providing risk information may be beneficial as some users (i.e., patients and/or remote monitors) focus solely on the current glucose value without giving much thought to whether the value is dropping or increasing to dangerous levels. This clinical risk may be based on the patient's current or most recent glucose level and the rate of change. For illustrative purposes, the application may use the following guidelines to assess a patient's risk level:

Patient's current glucose level is high, and the rate of change is increasing=High clinical risk to patient;
Patient's current glucose level is low, and the rate of change is decreasing=High clinical risk to patient;
Patient's current glucose level is low, and the rate of change is stable (i.e., not changing)=High clinical risk to patient;
Patient's current glucose level is high, and the rate of change is stable (i.e., not changing)=High clinical risk to patient;
Patient's current glucose level is high, and the rate of change is decreasing=Low clinical risk to patient;

Patient's current glucose level is low, and the rate of change is increasing=Low clinical risk to patient; and Patient's current glucose level is in target, and the rate of change is stable (e.g., not changing or relatively low rate of change)=Low clinical risk to patient.

FIGS. 8A, 8B, 8C, and 8D illustrate various mechanisms for communicating a patient's clinical risk level to a patient or remote monitor. These mechanisms may be used in isolation or in combination with each other to indicate a high clinical risk, a low clinical risk, or both.

Figure 8B:
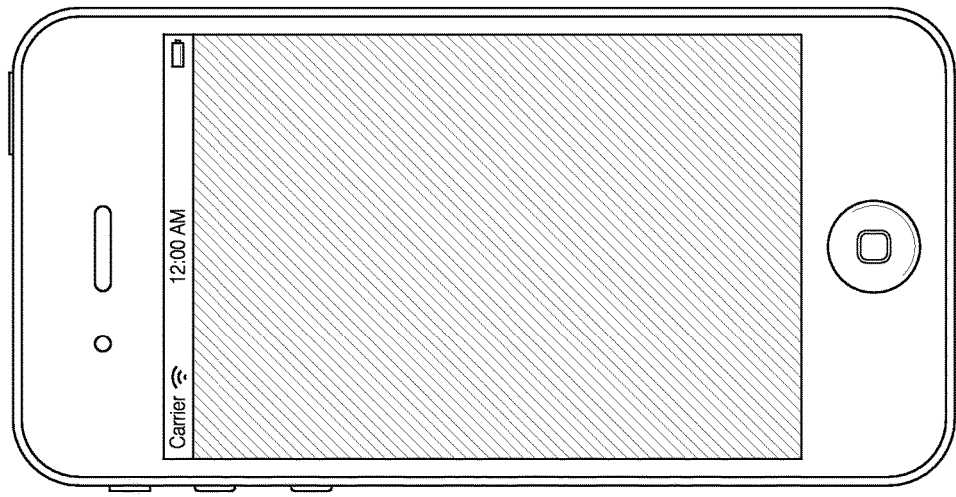
FIGS. 8A-8D illustrate various views of user interfaces that display a user's clinical risk in accordance with some exemplary implementations.
Figure 8A:
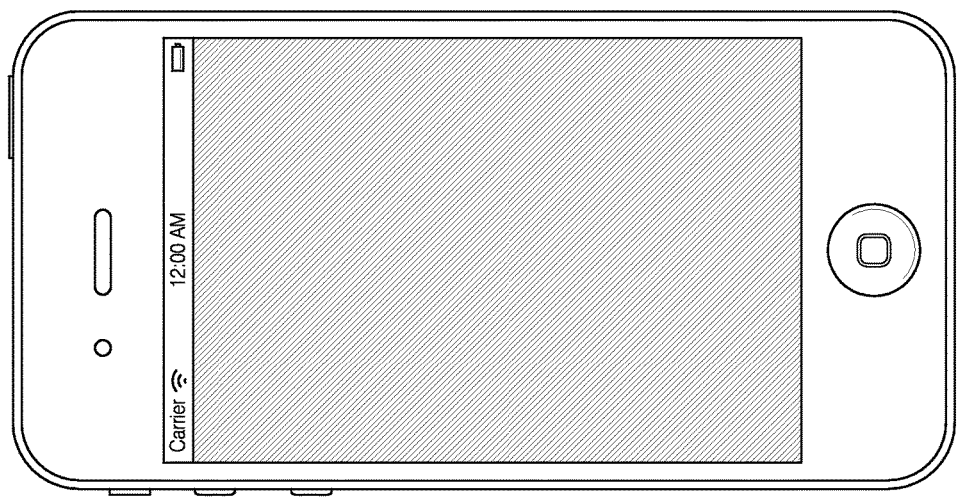

FIGS. 8A and 8B illustrate an implementation for alerting a user of a clinically risky situation by applying a color scheme to the display on a hand held computing device. The hand held computing device in these figures may be running multiple applications. In the instant implementation, the glucose monitoring application may be running in the background (i.e., inactive) as the user manipulates a different application in the foreground. If the application determines that the patient may enter a clinically risky state as described above, the application may apply a color scheme to shade the display with a particular color. The color that is selected may be based on, for example, whether it is determined that the patient is at risk of becoming hypoglycemic or hyperglycemic, whether the clinical risk is low or high, and the like. In some implementations, one or more of these parameters may be used in combination to determine the color scheme. In the implementation of FIG. 8A, the application may apply a red color scheme 1710 to indicate that the patient may be in danger of becoming hypoglycemic. In the implementation of FIG. 8B, the application may apply a yellow color scheme 1720 to indicate that the patient may be in danger of becoming hyperglycemic. In some implementations, application 255 may apply a red color scheme 1710 for a high-risk situation, a yellow color scheme 1720 for a moderate risk situation, and no shading or a grey shading for a relatively low risk situation. The shading on the screen may discreetly prompt the patient or remote monitor to take action to raise or lower the patient's glucose level as needed.

Figure 8D:
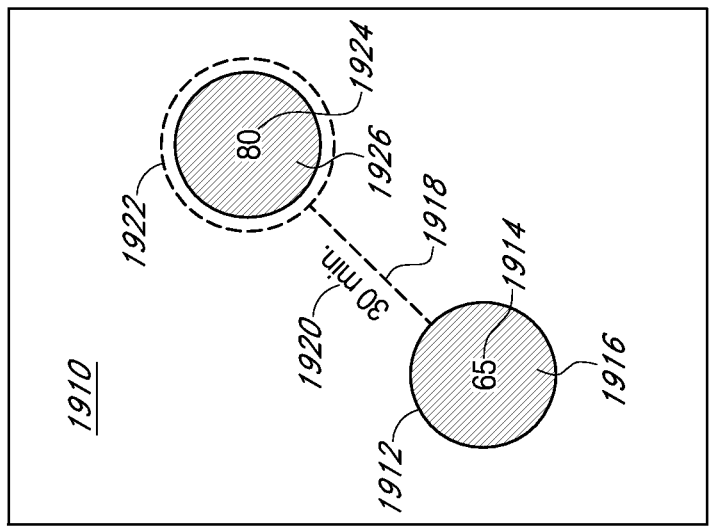
Figure 8C:
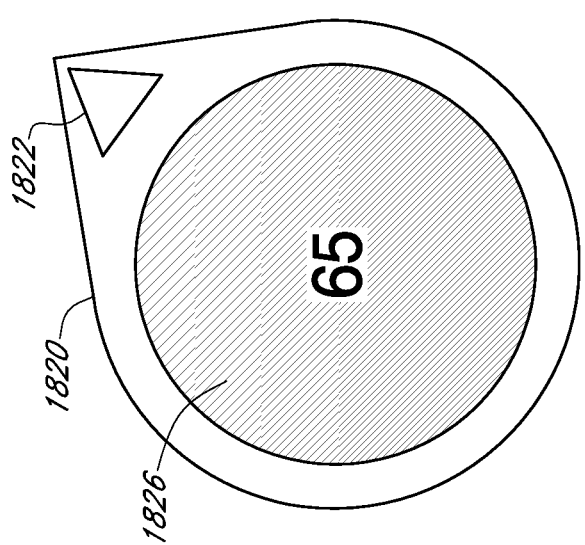

FIG. 8C illustrates an implementation for discreetly communicating a clinically risky situation to a user by varying the background color 1826 of unitary icon 1820. In the implementation of FIG. 8C, unitary icon 1820 has a background of a gradient of colors. This gradient may include multiple colors arranged in various patterns to represent the patient's clinical risk. Illustrating the patient's clinical risk using a gradient of colors allows a patient to quickly ascertain whether remedial action is needed. For example, if a patient's current glycemic state is low but rising into an in-target value, then the clinical risk to the patient may be low. Rather than display a solid red color in the unitary icon based on the patient's current glycemic state, a gradient of colors may be used to represent the predicted change in the patient's glycemic state using, for example, a red-gray gradient. In this example, the red-gray gradient may allow a user to quickly understand this his/her low glucose levels are rising.

In the implementation of FIG. 8C, the patient's current glycemic state may be visually represented in the lower left side of unitary icon 1820, and the patient's extrapolated glycemic state may be visually represented in the upper right side of the unitary icon. Other variations are possible including, for example, illustrating the current glycemic state on the bottom or left side of unitary icon 1820, and an extrapolated glycemic state on the top or right side of the unitary icon, and the like. Here, the patient's current glucose level is 65 mg/dL, which is determined to be low. As such, the lower left side of the unitary icon is shaded red. Because indicator 1822 is pointing northeast (i.e., a positive rate of change), the patient's glucose level is likely to rise at a steady rate of change. Consequently, even though the patient's glucose level is currently low, the patient's clinical risk may be considered low because his or her current glucose level is predicted to rise due to the positive rate of change. Because the patient's extrapolated glycemic state presents a low clinical risk, the upper right side of the unitary icon is shaded gray. In contrast, by way of example, should the rate of change be decreasing, then background color 1826 may be completely red, without any grey shading, to indicate that the patient's current glycemic state (which is low) may continue to drop and put the patient in a high clinical risk condition.

In some implementations, the application may change the appearance of indicator 1822 to indicate a clinically risky situation. For example, the application may enlarge indicator 1822, flash or blink the indicator, and/or change its color depending upon the level of the patient's determined clinical risk. In an implementation, the indicator 1822 may flash and/or may be a first color when it is determined that the user is in a high risk clinical situation, and may not flash and/or may be a different second color when the user is determined to be in a low risk clinical situation.

FIG. 8D illustrates another mechanism for visualizing a patient's clinical risk state using application 255. View 1910 may include two icons 1912 and 1922. Icon 1912 displays the patient's current glucose level 1914 and has a background color 1916. Background color 1916 indicates the patient's current glucose level, such as whether the current glucose level is low, in target, or high. Icon 1922 represents the patient's extrapolated glucose level 1924 and has a background color 1926. Background color 1926 indicates whether the extrapolated glucose level is predicted to be low, in target, or high. Extrapolation line 1918 connects unitary icons 1912 and 1922. A time indicator 1920 may be displayed adjacent to extrapolation line 1918 to indicate when the extrapolated glucose level is estimated to occur. In the implementation of FIG. 8D, unitary icons 1912 and 1922 do not have indicators to represent the rate of change. Omitting these indicators may be beneficial as it reduces the amount of information displayed to the user. In some implementations, however, these indicators may be added to unitary icons 1912 and 1922.

The glucose monitoring application may supplement the visualizations described above with textual messages to indicate the clinical risk. These messages may include suggested actions to mitigate the risk. For example, when the user is at risk for becoming hypoglycemic, the message may prompt the patient to administer insulin, consume glucose or food, seek medical attention, and the like.

Application 225 running on hand held computing devices 18 and/or 19 may be configured to issue alerts using alert module 275. Alerts may notify a user of glucose levels that exceed or fall below certain predetermined thresholds, for example. Generating these alerts may prompt a patient or remote monitor to take corrective action in order to prevent injury to the patient. Different types of alerts may be generated including, for example, audible alerts, visual alerts, haptic alerts, message alerts (e.g., sending an e-mail to a patient or remote monitor), and a combination thereof.

Figure 9A:
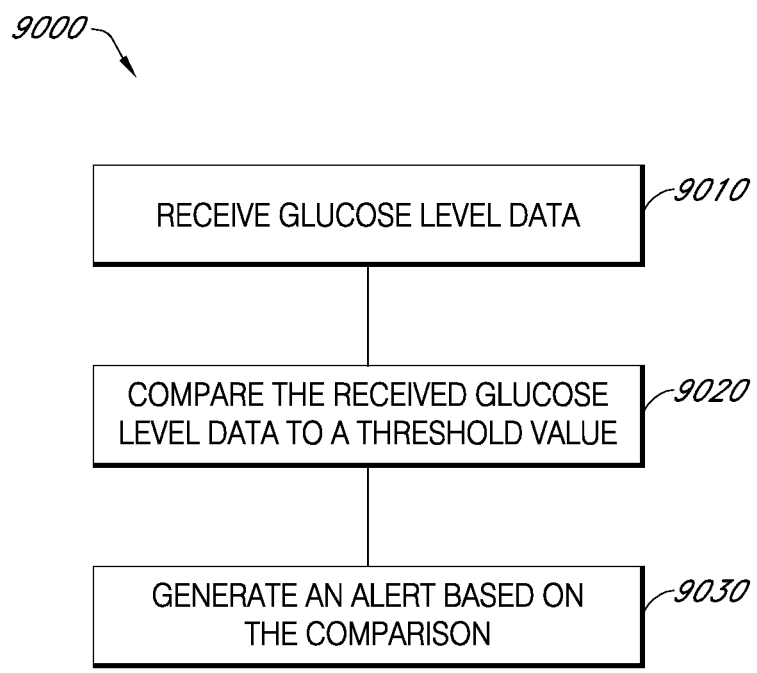
FIG. 9A illustrates a process for generating an alert in accordance with some exemplary implementations.

Alert module 275 may generate different alerts using process 9000 illustrated in FIG. 9A. At 9010, alert module 275 may receive glucose level data from sensor system 8. At 9020, alert module 275 may compare the received glucose level data to various predetermined thresholds, such as glucose value threshold and/or a rate of change threshold.

For example, if the low glucose level alert is set in alert module 275, the alert module may compare the received glucose level to a corresponding threshold value for this alert. Based on this comparison, alert module 275 may generate an alert on device 18 and/or 19 at 9030. For example, alert module 275 may generate an alert if the received glucose level is less than the threshold value. The following paragraphs describe different types of alerts maintained by alert module 275.

Figure 9B:
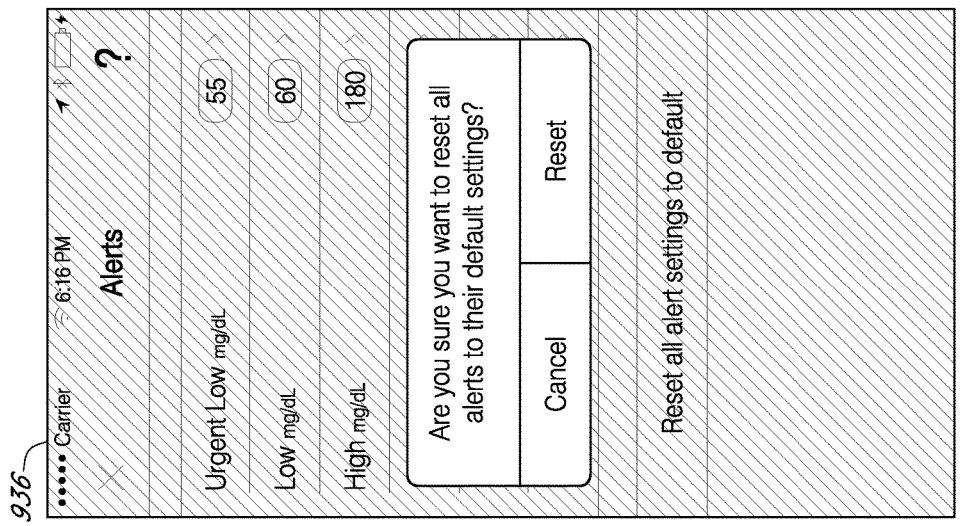
FIG. 9B illustrates user interfaces for managing a user's alerts in accordance with some exemplary implementations.
Figure 9B:
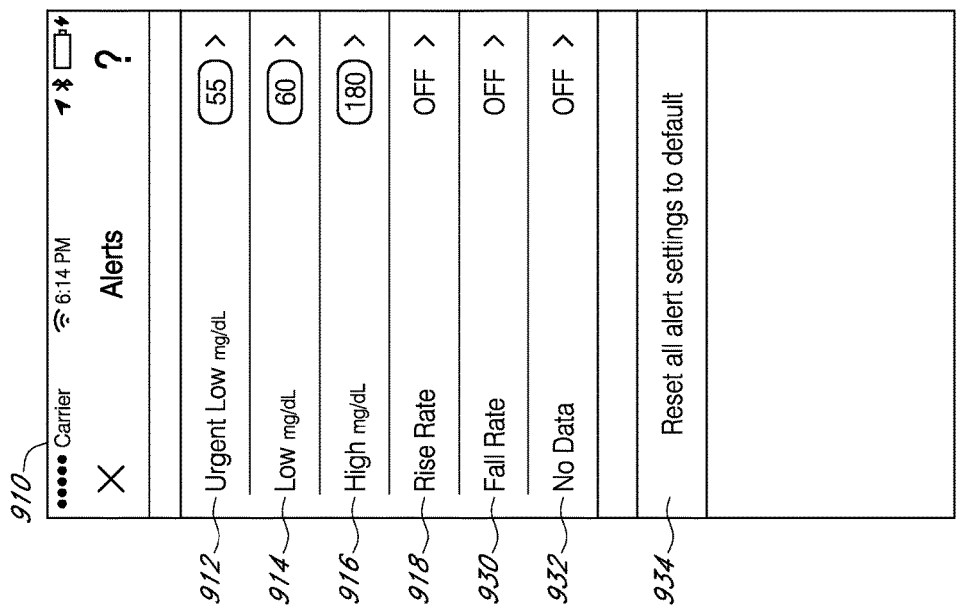

FIG. 9B illustrates a user interface 910 for managing a user's alerts. These alerts may include glucose level alerts, such as an urgent low alert 912, a low alert 914, a high alert 916, a rise rate alert 918, and a fall rate alert 930. Glucose level alert module 276 may manage these glucose level alerts. User interface 910 may also include alerts relating to a communication failure, such as no data alert 932. Communication failure alert module 277 may manage no data alert 932.

Alert menu 910 may indicate whether these alerts are enabled or disabled. For example, rise rate alert 918 may be disabled as indicated by the word "OFF" in alert menu 910. In another example, urgent low alert 912 may be enabled as indicated by the adjacent green label. This green label may display a number or threshold value that indicates when the alarm may trigger. In the implementation of FIG. 9B, urgent low alert 912 may trigger if the glucose level falls below 55 mg/dL. The user may reset all alert settings to default values by selecting item 934. Upon doing so, user interface 936 may appear, asking the user to confirm the reset request. If, however, the user wishes to adjust a particular alert's settings, he or she may do so by selecting the appropriate alert. Each of these alerts is described below with respect to FIGS. 10A, 10B, 11, 12, 13, 14, and 15.

Figure 10A:
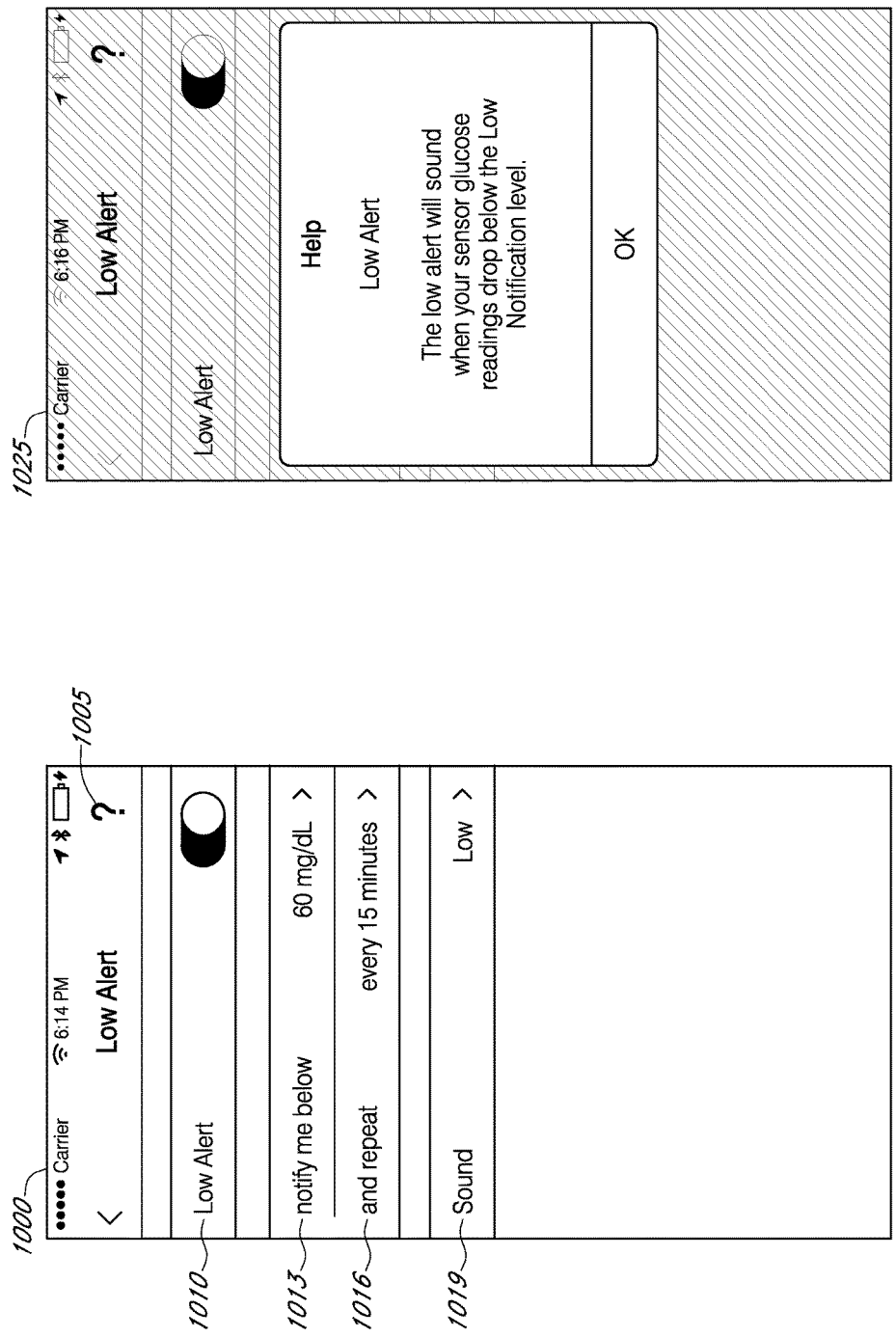
FIGS. 10A and 10B illustrate user interfaces for a low alert in accordance with some exemplary implementations.
Figure 10B:
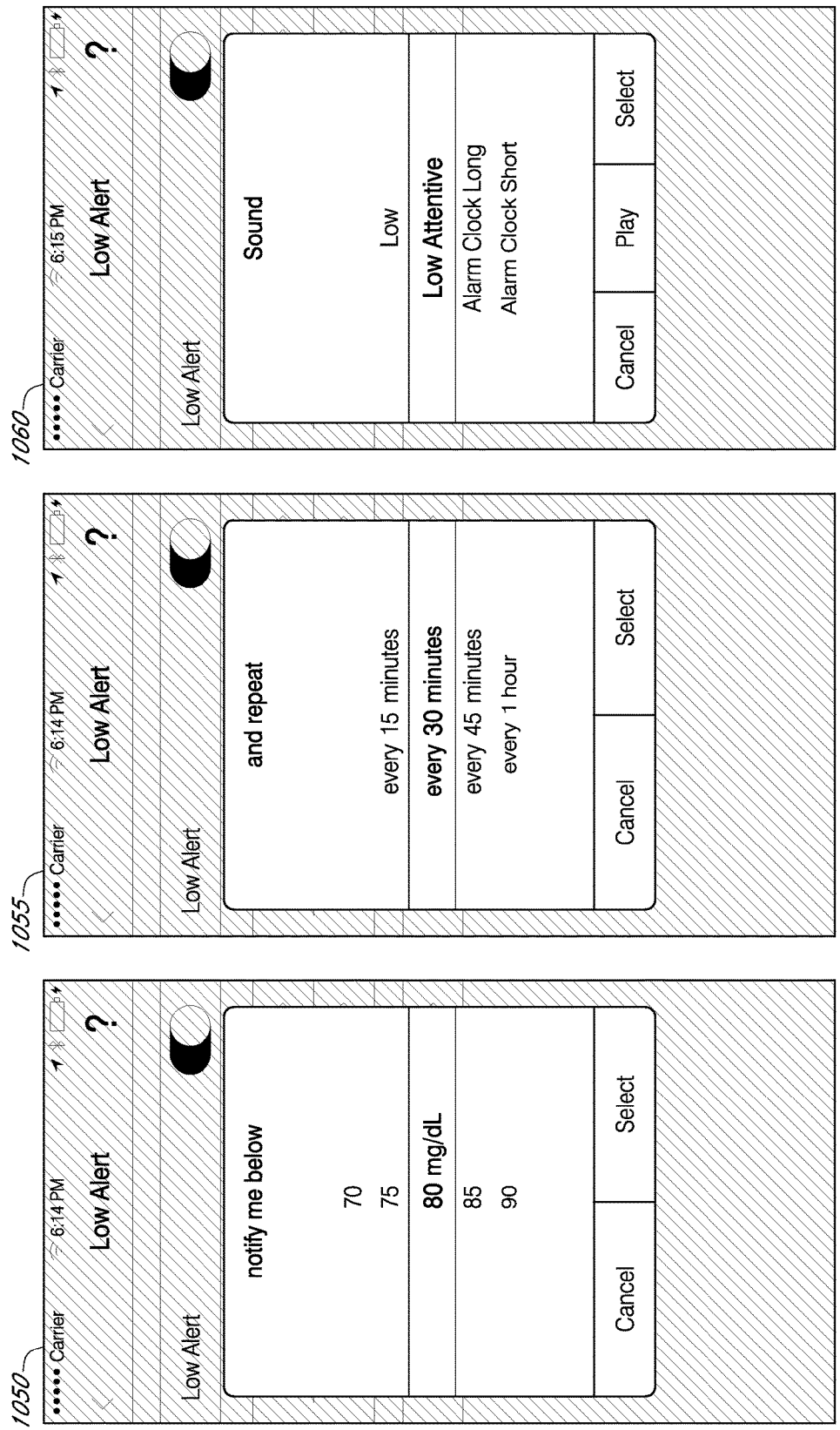

FIGS. 10A and 10B illustrate various user interfaces for adjusting the settings associated with the low alert. User interface 1000 may appear when low alert 914 is selected from alert menu 910. The user may enable or disable the low alert by adjusting slider 1010. The user may obtain information regarding the low alert by selecting question mark icon 1005. Upon doing so, user interface 1025 may be displayed. User interface 1025 may be a help screen that provides a description of the low alert. The low alert may be generated or triggered when the patient's glucose level falls below a particular threshold. User interface 1000 may also display various settings associated with the low alert. These settings may include the threshold value or trigger 1013 for the alert, how often the alert should be repeated 1016, and the sound 1019 for the alert. User interface 1000 may display the current values for settings 1013, 1016, and 1019. The user may change these values by selecting the desired setting.

For example, if the user selects item 1013 to change the threshold value, then user interface 1050 may be displayed. If the user selects item 1016 to change the alert's repeat settings, then user interface 1055 may be displayed. Likewise, if the user selects item 1019 to change the sound associated with the alert, then user interface 1060 may be displayed. The user may select a sound from a predetermined list of sounds. Designating different sounds for different alerts may allow a user to distinguish the alerts from each other. The user may use the scrolling keypads on interfaces 1050, 1055 and 1060 to select the desired values for settings 1013, 1016, and 1019, respectively.

Figure 11:
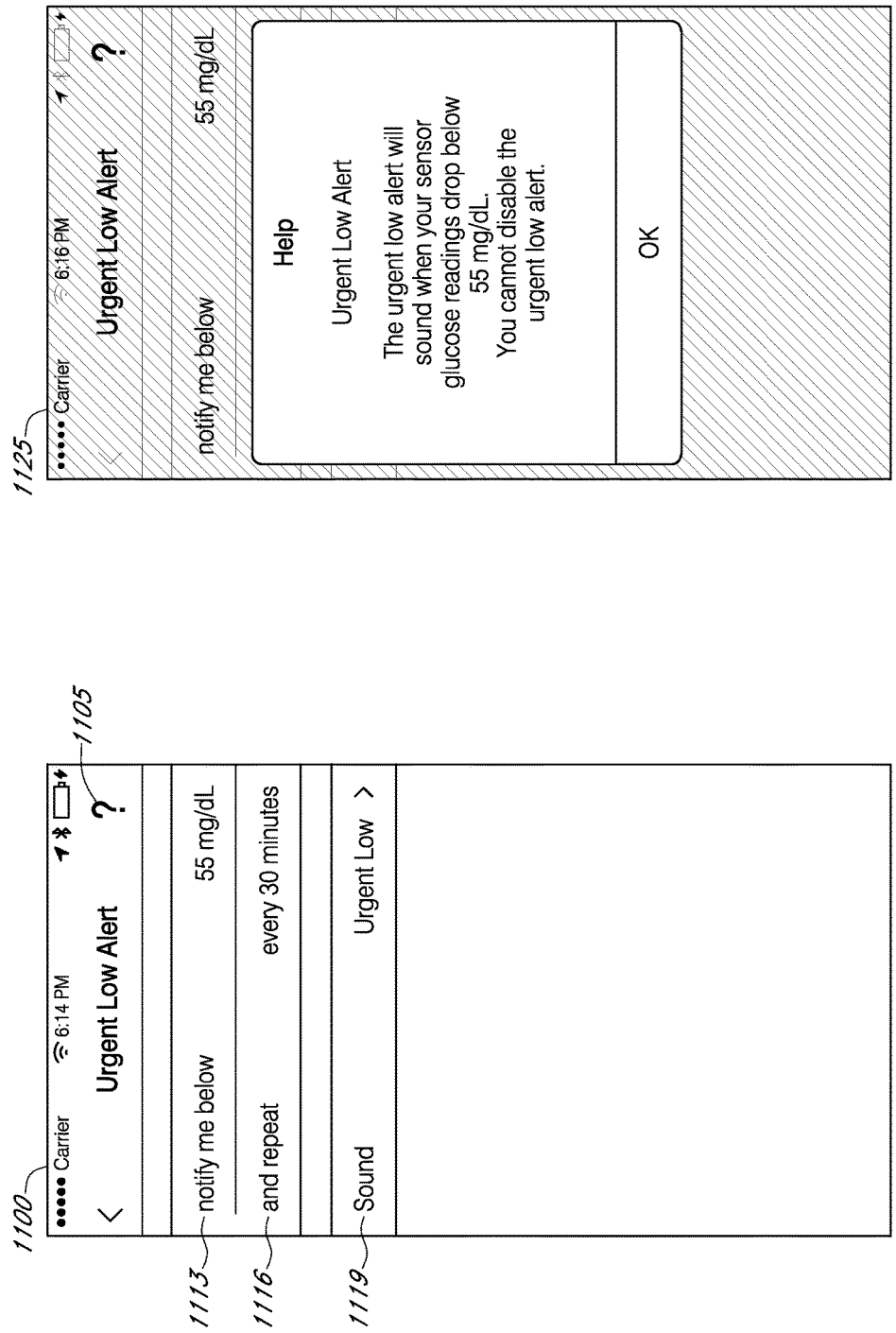
FIG. 11 illustrates user interfaces for an urgent low alert in accordance with some exemplary implementations.

FIG. 11 illustrates user interfaces 1100 and 1125 associated with the urgent low alert. User interface 1100 may appear when urgent low alert 912 is selected from alert menu 910. The user may obtain information regarding the urgent low alert by selecting question mark icon 1105. Upon doing so, user interface 1125 may be displayed. User interface 1125 may be a help screen that provides a description of the urgent low alert. The urgent low alert may be generated or triggered when the patient's glucose level falls below a predetermined threshold. In some implementations, this predetermined threshold may not be adjusted, and this alert may not be disabled. User interface 1100 may also display various settings associated with the urgent low alert. These settings may include the threshold value or trigger 1113 for the alert, how often the alert should be repeated 1116, and the sound 1119 for the alert. The values associated with settings 1113, 1116, and 1119 may be adjusted using interfaces similar to those illustrated in FIG. 10B.

Figure 12:
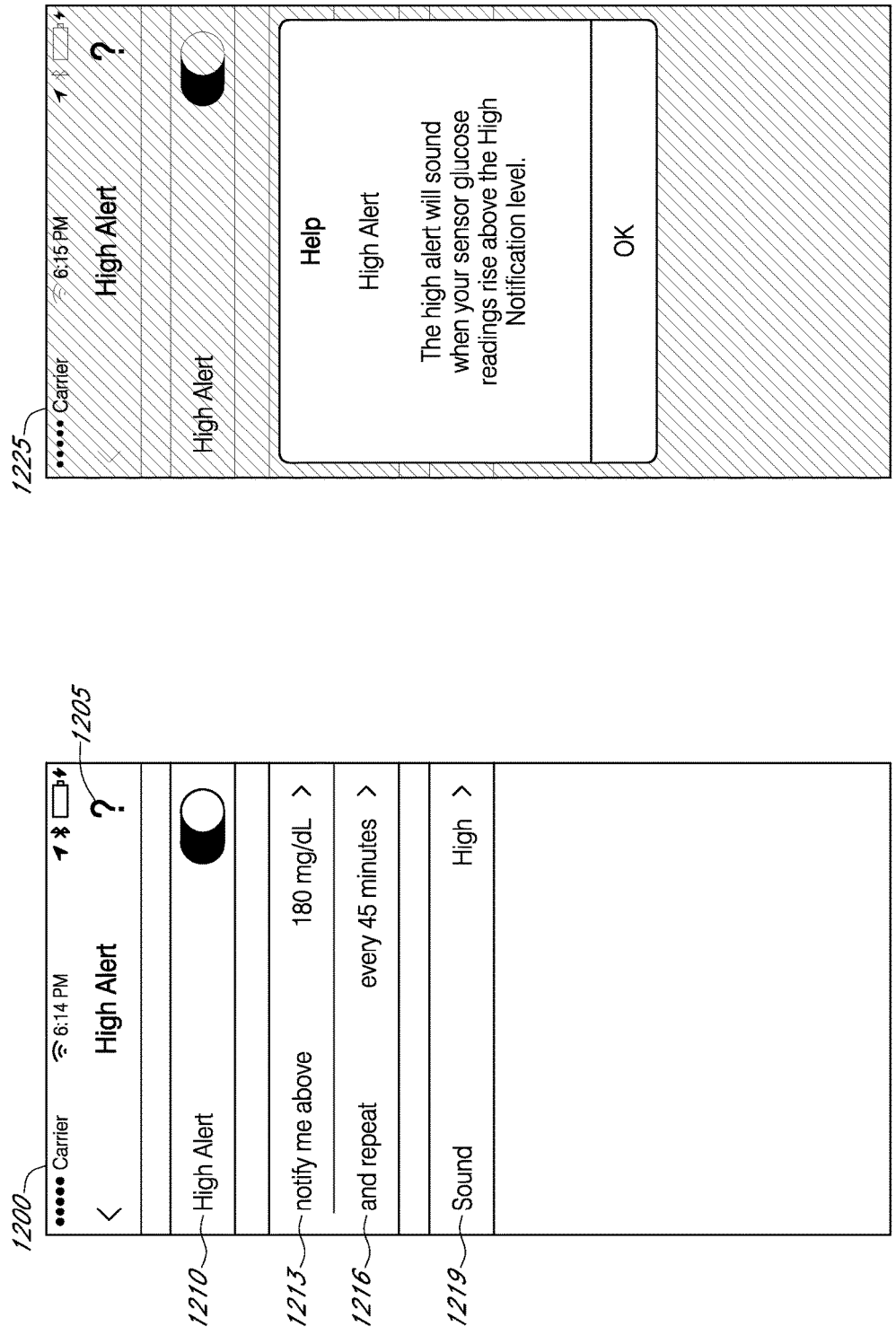
FIG. 12 illustrates user interfaces for a high alert in accordance with some exemplary implementations.

FIG. 12 illustrates user interfaces 1200 and 1225 associated with the high alert. User interface 1200 may appear when high alert 916 is selected from alert menu 910. The user may enable or disable the high alert by adjusting slider 1210. The user may obtain information regarding the high alert by selecting question mark icon 1205. Upon doing so, user interface 1225 may be displayed. User interface 1225 may be a help screen that provides a description of the high alert. The high alert may be generated or triggered when the patient's glucose level readings increase above a certain threshold. User interface 1200 may also display various settings associated with the high alert. These settings may include the threshold value or trigger 1213 for the alert, how often the alert should be repeated 1216, and the sound 1219 for the alert. The values associated with settings 1213, 1216, and 1219 may be adjusted using interfaces similar to those illustrated in FIG. 10B.

Figure 13:
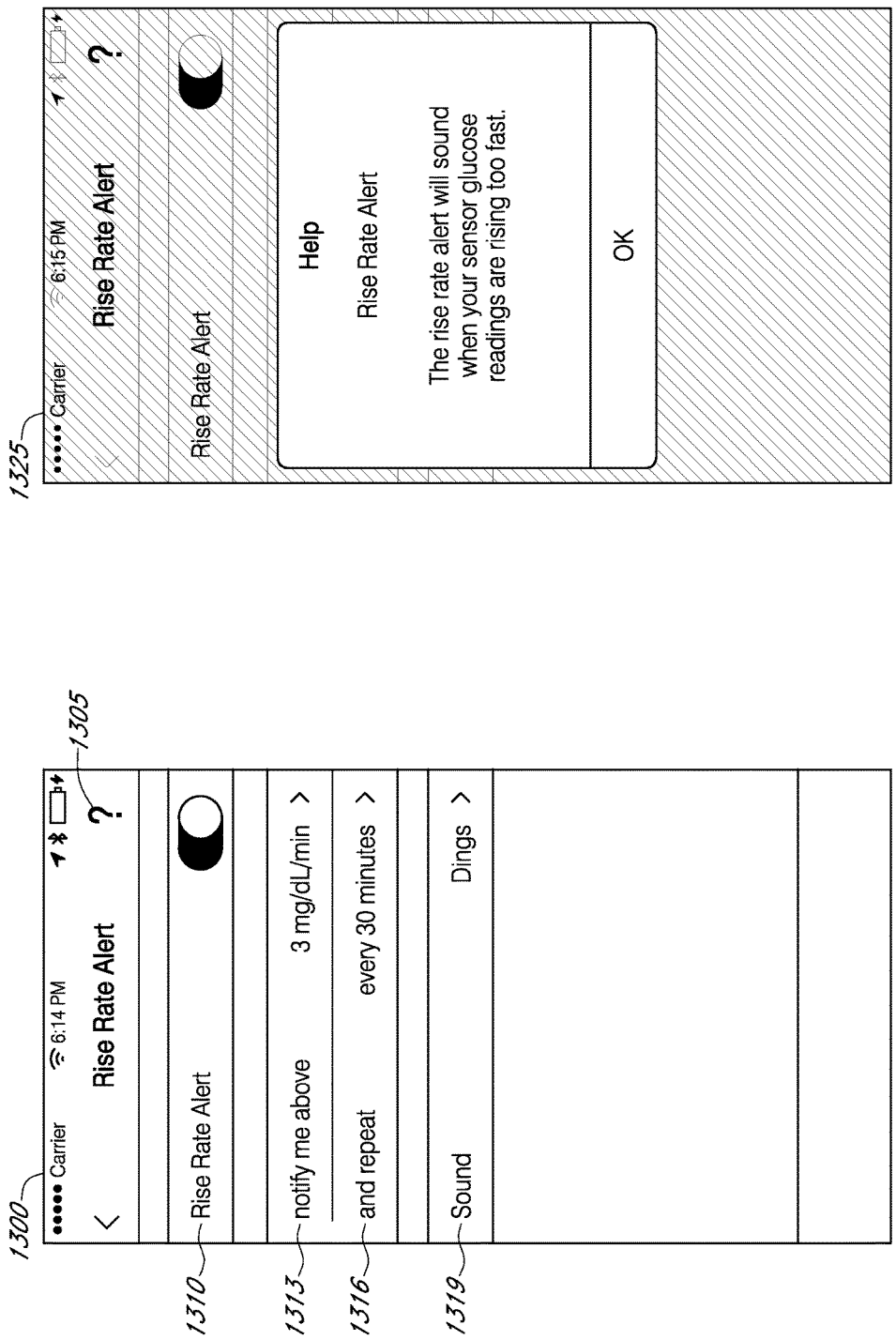
FIG. 13 illustrates user interfaces for a rise rate alert in accordance with some exemplary implementations.

FIG. 13 illustrates user interfaces 1300 and 1325 associated with the rise rate alert. User interface 1300 may appear when rise rate alert 918 is selected from alert menu 910. The user may enable or disable the rise rate alert by adjusting slider 1310. The user may obtain information regarding the rise rate alert by selecting question mark icon 1305. Upon doing so, user interface 1325 may be displayed. User interface 1325 may be a help screen that provides a description of the rise rate alert. The rise rate alert may be generated or triggered when the patient's glucose levels rise too quickly relative to a particular threshold. User interface 1300 may also display various settings associated with the rise rate alert. These settings may include the threshold value or trigger 1313 for the alert, how often the alert should be repeated 1316, and the sound 1319 for the alert. The values associated with settings 1313, 1316, and 1319 may be adjusted using interfaces similar to those illustrated in FIG. 10B.

Figure 14:
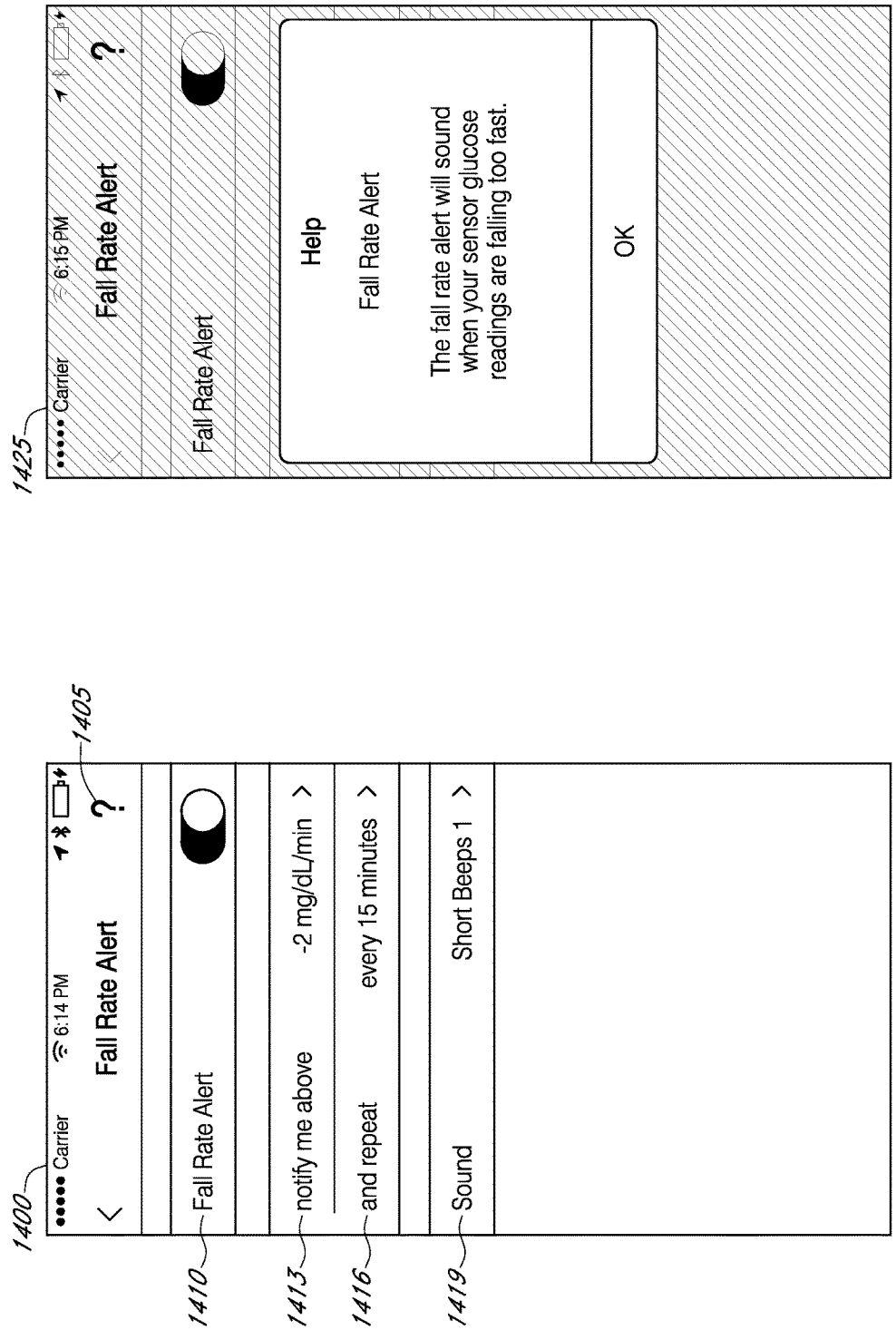
FIG. 14 illustrates user interfaces for a fall rate alert in accordance with some exemplary implementations.

FIG. 14 illustrates user interfaces 1400 and 1425 associated with the fall rate alert. User interface 1400 may appear when fall rate alert 930 is selected from alert menu 910. The user may enable or disable the fall rate alert by adjusting slider 1410. The user may obtain information regarding the fall rate alert by selecting question mark icon 1405. Upon doing so, user interface 1425 may be displayed. User interface 1425 may be a help screen that provides a description of the fall rate alert. The fall rate alert may be generated or triggered when the patient's glucose levels fall too quickly relative to a particular threshold. User interface 1400 may also display various settings associated with the fall rate alert. These settings may include the threshold value or trigger 1413 for the alert, how often the alert should be repeated 1416, and the sound 1419 for the alert. The values associated with settings 1413, 1416, and 1419 may be adjusted using interfaces similar to those illustrated in FIG. 10B.

Figure 15:
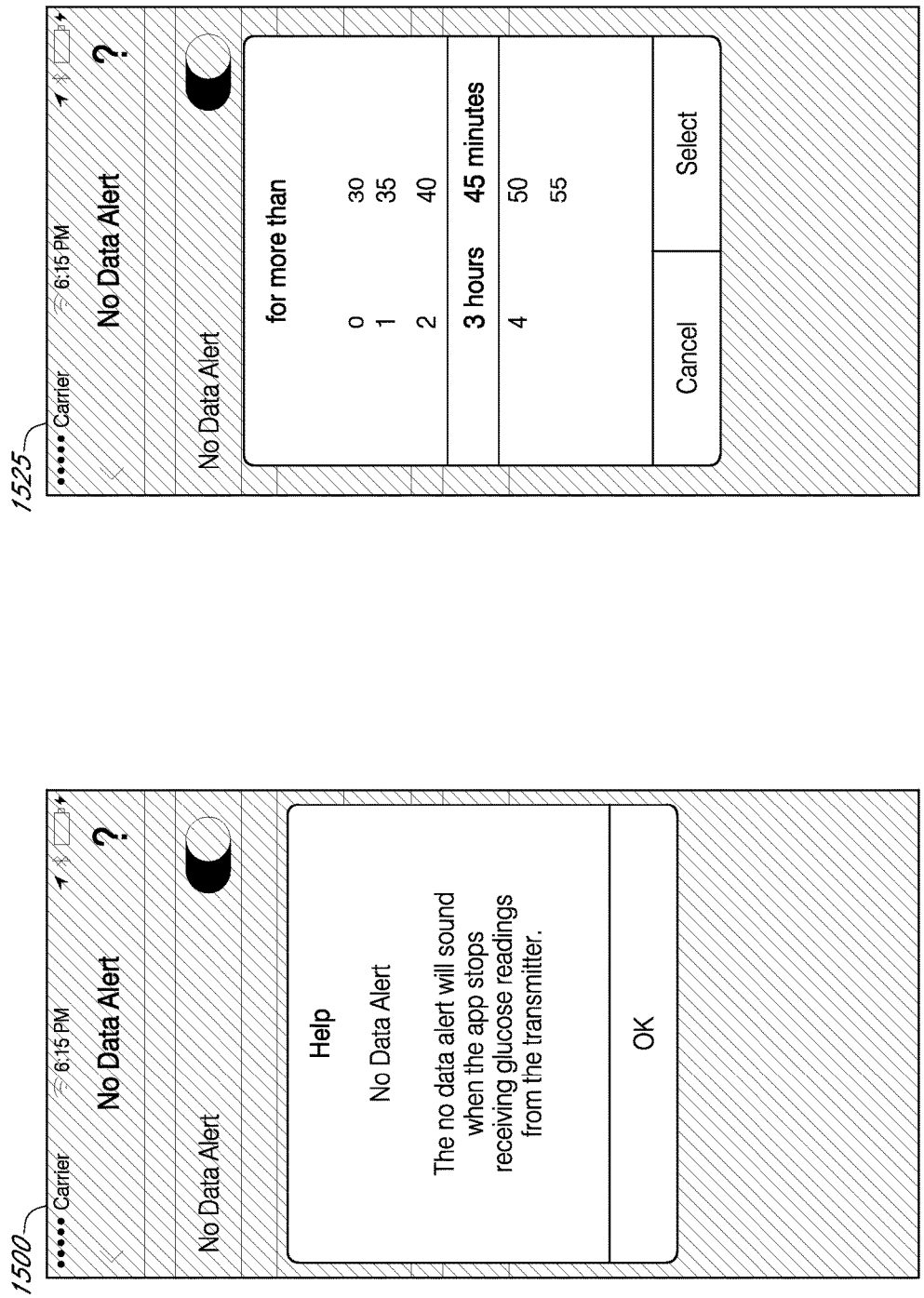
FIG. 15 illustrates user interfaces for a no data alert in accordance with some exemplary implementations.

FIG. 15 illustrates user interfaces 1500 and 1525 associated with the no data alert. User interface 1500 may be a help screen that provides a description of the no data alert. Communication failure alert module 277 may generate the no data alert when the application stops receiving glucose readings from sensor system 8 after a predetermined period of time. The user may adjust the value of this predetermined time using the scrolling keypad of user interface 1525.

Alert module 275 may generate an alert to advise a user that a particular threshold condition or level has been met. Because the application may be running on different hand held computing devices 18 and 19 that may be multi-use devices (i.e., not dedicated glucose monitoring devices), potentially with different operating platforms, these alerts may be tailored to operate within the constraints of each computing device. For example, the ring or alert volume in a smart phone's settings may determine the volume of an alert. If, for example, the mute switch is enabled on the phone, then application 255 may be unable to generate audible alerts. In another example, a user may set various notification settings in his or her phone. These settings may affect the manner in which alerts are displayed. Various factors may affect this process including, for example, whether the phone is locked or unlocked, whether the application is currently being used or idling in the background, and the like. The phone may be in a locked state when, for example, the user is unable to interact with applications running on the phone. While in a locked state, the user may be able to enter a passcode to bring the phone into an unlocked state. When the phone is in an unlocked state, a user may be able to interact with applications running on the phone. The following implementations disclose various solutions to these design constraints.

Figures 16A, 16B, 16C:
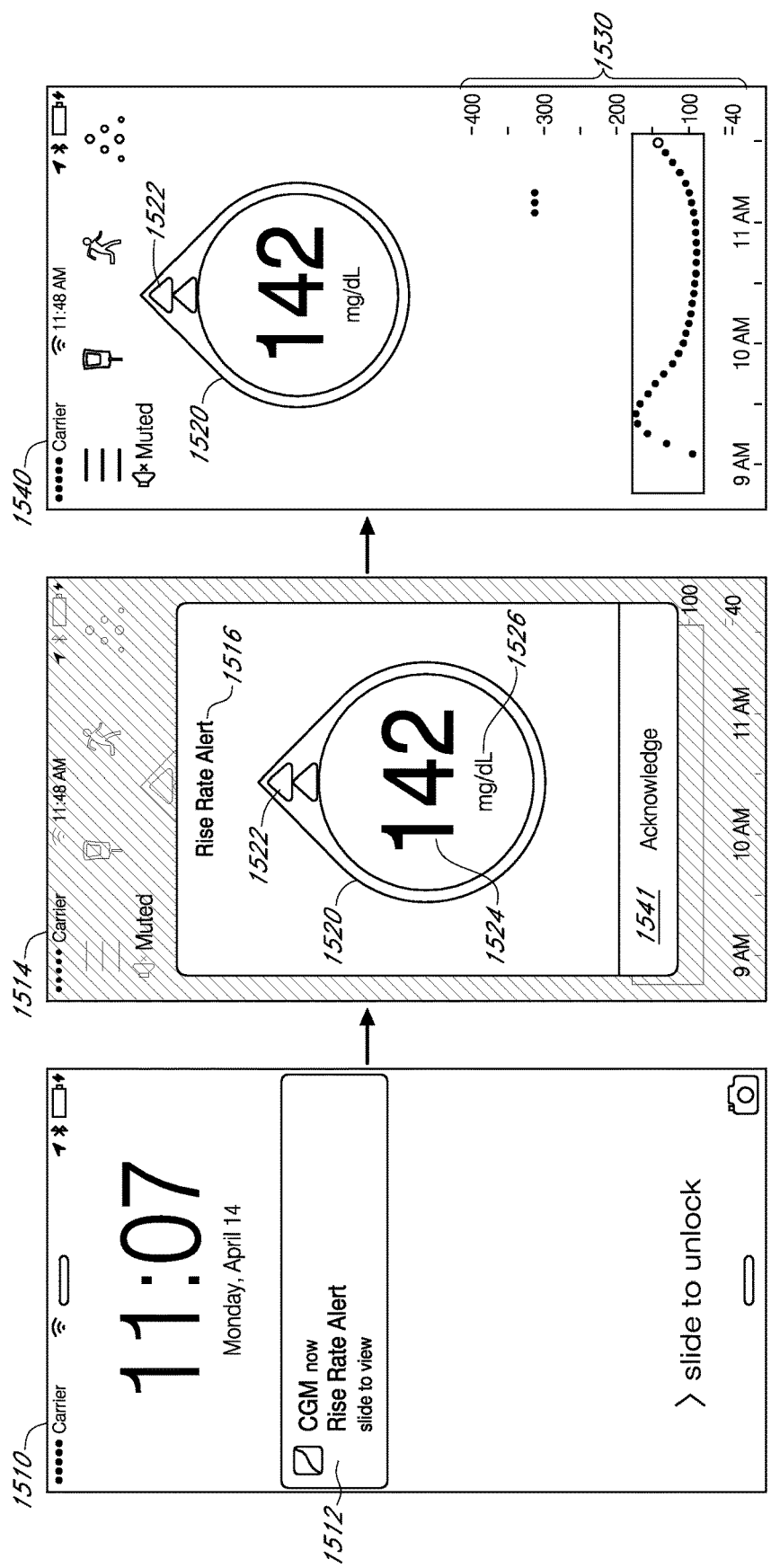
FIGS. 16A-16C illustrate various user interfaces for an alert in accordance with some exemplary implementations.

FIGS. 16A, 16B, and 16C illustrate a mechanism for alerting a user when his or her hand held computing device 18 and/or 19 is locked. Although the implementation of FIGS. 16A, 16B, and 16C is described with respect to a rise rate alert, this implementation may apply to any alert discussed herein.

FIG. 16A illustrates an interface 1510 that displays a rise rate alert 1512 on a locked screen. Glucose level alert module 276 may generate alert 1512 when the user has enabled the alert and when the threshold level has been reached as described above with respect to process 9000 of FIG. 9A. Alert 1512 may include text indicating the type of alert that has been generated or triggered, an icon or graphical representation of the alert, and the like. In the implementation of FIG. 16A, the alert does not display any numerical values associated with the alert (e.g., how quickly the patient's glucose level is rising and how long it has exceeded the threshold level). Omitting this information can allow a user to view his or her alerts discreetly in public without calling undue attention to himself or herself. Omitting this information can also prevent the presentation of stale data and encourage the user to launch the application in order to obtain more detailed information. For example, if alert 1512 displayed a patient's current glycemic state on device 18 and the device loses connectivity with sensor system 8, the patient may think that his/her current glycemic state is stable when, in fact, application 255 is unable to update this value. This situation may be especially dangerous if, for example, alert 1512 provides a numerical value indicating that the patient's current glycemic level is in-target but has actually dropped below lower threshold value 332 since the patient's phone 18 has lost connectivity with sensor system 8. Whether these numerical values and/or a representation of the rate of change are displayed may be configured by a user using alert module 275 and/or glucose level alert module 276 in some implementations.

Alert 1512 may display instructions for viewing additional information regarding the alert. In the instant implementation, the alert may instruct the user to "slide to view." Glucose alert module 276 may display user interface 1514 of FIG. 16B after the user has followed these instructions.

User interface 1514 may provide details regarding the nature of the alert. The details that are displayed may depend on the alert that is generated. For example, when the alert is related to the status of the system, the alert may provide information regarding the alert condition. For example, if no data alert 932 is generated, then user interface 1514 may display the duration of time since application 255 last received glucose level data from sensor system 8. In another example, if a calibration measurement is needed, then user interface 1514 may display a textual message indicating the same.

When the alert is related to the patient's glucose level, user interface 1514 may display, for example, the patient's current glucose level, the threshold value associated with the alert, and the like. User interface 1514 may specify the alert type 1516 and display a unitary icon 1520 for glucose level alerts. Unitary icon may display the patient's current glucose level 1524. The background color 1526 may indicate that this glucose level is in target. However, because indicator 1522 has two arrow indicators, the rate of change of this glucose level is rapidly increasing. Under these circumstances, the patient may become hyperglycemic if no action is taken. User interface 1514 may prompt the user to acknowledge this alert by selecting item 1541. If the user does not acknowledge the alert, the application may continue to re-alert until acknowledgement has been received or until the condition that triggered the alert is no longer satisfied. The application may re-alert at predetermined intervals (e.g., every 5 minutes) until the user acknowledges the alert. Continuing to re-alert may help ensure that a user sees the alert, particularly if application 255 is idling in the background.

Once the user acknowledges the alert, glucose alert module 276 may activate or launch the application and display user interface 1540 illustrated in FIG. 16C. User interface 1540 may be the home screen and provide detailed information regarding the patient's glucose levels. Like user interface 1514, this interface may include unitary icon 1520 and indicator 1522. In addition, this interface may also display a trend graph 1530 of the patient's glucose levels.

The implementation of FIGS. 16A, 16B, and 16C may be varied depending on the state of the hand held computing device and/or the state of the application. If, for example, the hand held computing device is unlocked and the application is active (i.e., currently being used), then alerts may be displayed within the application as notifications. If, however, the hand held computing device is unlocked and the application is idling in the background, then alerts may be displayed as banners. These banners may temporarily appear anywhere within the computing device's display screen (e.g., near the top) and vanish after a predetermined period of time (e.g., 5 seconds). If a user slides his or her finger over the banner alert, alert module 264 may display user interface 1514 of FIG. 16B, for example. If the mute switch on the device is enabled, then the application may generate various non-audible alerts including, for example, a vibrating alert or visualization. The visualization may include, for example, a flashing screen, a shaded screen, and the like as described above with respect to FIGS. 8A and 8B. If alerts may not be audibly generated on the patient's hand held computing device, another device, such as receiver 16 of FIG. 1, may generate these alerts. The application may re-generate these notifications, banners, vibrating alerts, and visualizations until the alert is acknowledged or until the condition that triggered the alert is no longer satisfied. A notification center on the hand held computing device may maintain a log of these alerts. This log may specify, for example, the type of alert, when the alert was triggered, how many times it was re-generated, and the like. The notification center may remove an alert after it has been acknowledged. A user may view old alerts from a history view in the application.

In some implementations, alert settings may be modified based on the time of day. If for, example, a patient is asleep at night between 10 PM and 6 AM, he or she may be less likely to be aware of his or her glycemic state and/or to hear or respond to alerts. In order to account for the patient's decreased awareness and responsiveness during these hours, the application may enter a night mode by automatically tightening the glucose threshold levels for various alerts. Adjusting these threshold levels may account for a reduced responsiveness in a patient as he or she may be sleeping. These adjustments may, in turn, allow more time for the patient or a remote monitor to take corrective action before the patient experiences serious injury.

Figure 17:
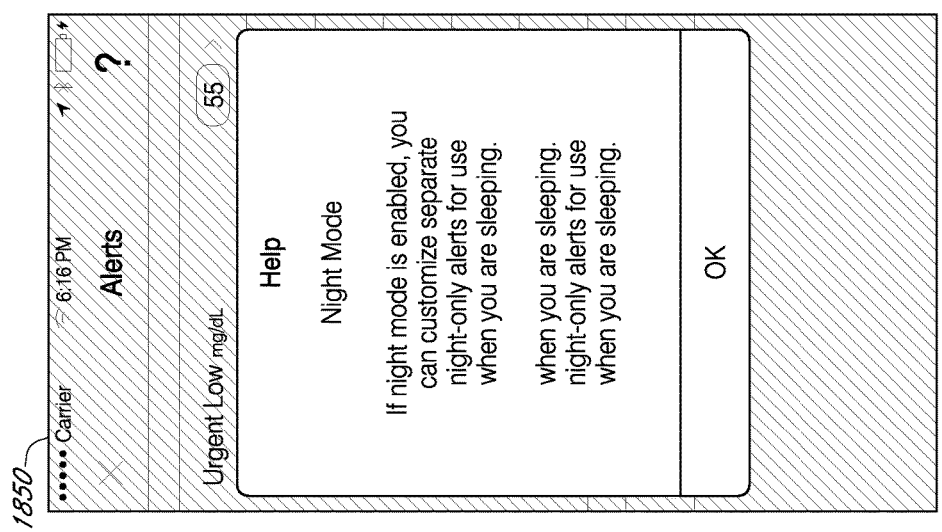
FIG. 17 illustrates a user interface for night mode operation in accordance with some exemplary implementations.

For example, if the low alert is normally triggered when the patient's glucose level drops below 60 mg/dL, then the night mode threshold may be 80 mg/dL. Increasing the threshold level for the low alert may allow the application to generate this alert earlier or more frequently. In another example, if the high alert is normally triggered when the patient's glucose level rises above 180 mg/dL, then the night mode threshold may be 190 mg/dL, so as to avoid disturbing the patient's sleep. Increasing the threshold level for the high alert may allow the application to generate this alert less frequently. FIG. 17 illustrates a user interface 1850 that describes night mode operation. A user may designate night mode hours and select which alerts are subject to night mode adjustments. If night mode is disabled, the alerts may be active all day. In some implementations, only low alerts may be activated during night mode operation and high alerts may be deactivated because a hypoglycemic state is more dangerous than a hyperglycemic state.

In implementations where an insulin pump is attached to the patient, the insulin pump may have a different insulin delivery profile during night mode hours. In some implementations, night mode alerts may have different alert sounds, volume, and repeat frequencies than non-night mode alerts. For example, the application may use high volume jarring sounds for alarms in order to wake the user during night mode hours.

Figure 18:
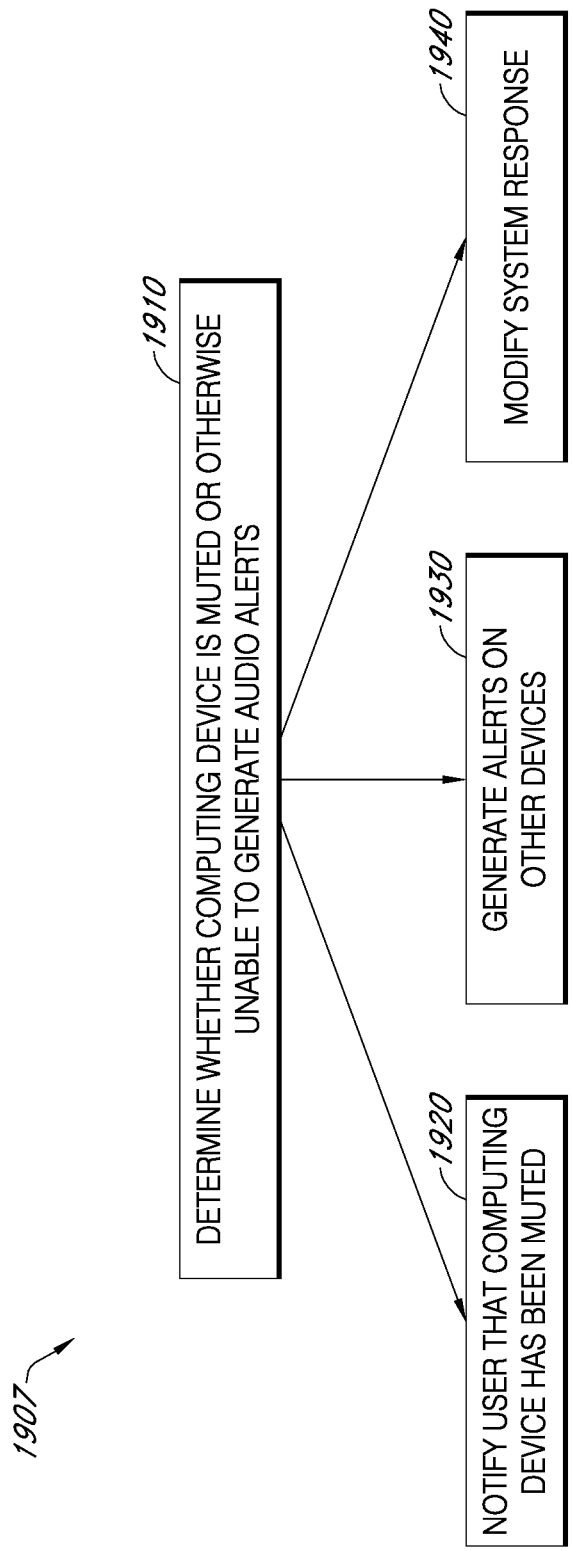
FIG. 18 illustrates a process for issuing an alert when a computing device is in mute mode in accordance with some exemplary implementations.
Figure 19:
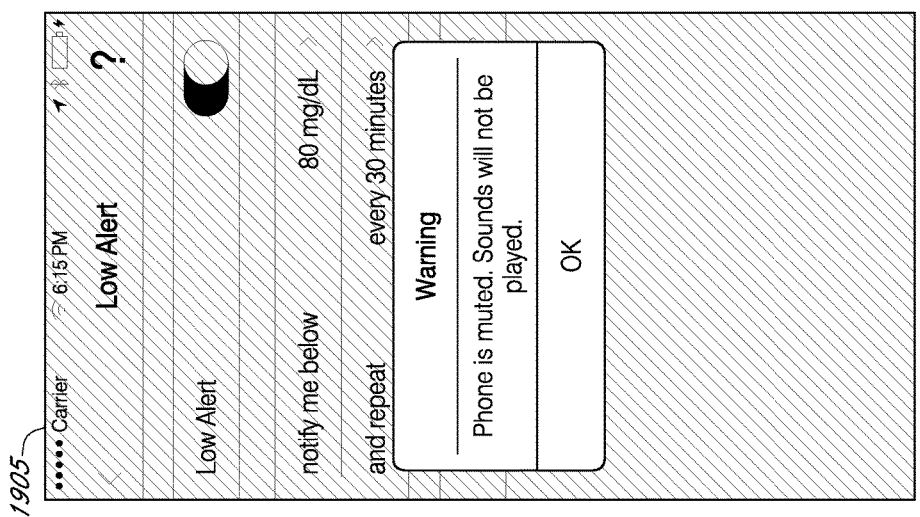
FIG. 19 illustrates a user interface for a muted computing device in accordance with some exemplary implementations.

As described above, the state of a user's hand held computing device may affect alert generation. If, for example, the hand held computing device is in a muted state, then a user may be unable to hear audible alerts. This may be problematic if, for example, the user accidentally mutes his or her hand held computing device. FIG. 18 illustrates a process 1907 for issuing an alert when computing device 18 is muted or otherwise unable to generate audible alerts.

At 1910, mute mode alert module 278 may determine whether the mute mode on computing device 18 has been enabled or if audible alerts from application 255 are suppressed. If so, mute mode alert module 278 may perform one or more of processes 1920, 1930, and 1940. These processes may be performed sequentially or substantially simultaneously.

At 1920, mute mode alert module 278 may notify the user that the mute mode has been enabled on computing device 18. In some implementations, mute mode alert module 278 may display graphical user interface 1905 illustrated in FIG. 19 to educate the user of the drawbacks of muting his or her computing device. User interface 1905 may indicate that sounds will not be played. Mute mode alert module 278 may display user interface 1905 when the user sets up alerts using alert menu 910 or when the application detects that the computing device is in a muted state. Mute mode alert module 278 may additionally generate a vibratory alert to catch the user's attention. In order to close user interface 1905 and to stop these vibrations, the user may be required to acknowledge the message. In some implementations, the mute mode alert module 278 may send a text message or email message to the user to indicate that the computing device has been muted. Additionally or alternatively, the mute mode alert module 278 may cause the computing device to send a message regarding the patient's muted device to a server, such as server 230. The server may, in turn, inform various remote monitors 19, such as family members, physicians, and the like.

In addition to informing remote monitors that the patient's device is muted, the mute mode alert module 278 may also inform remote monitors that an alert has been triggered at the patient's computing device and that the mute mode is enabled at the patient's computing device. For example, if the patient's low alert threshold level is satisfied, the mute mode alert module 278 may send a message to server 230 indicating the same. Server 230 may, in turn, relay the message to the remote monitors. These messages may be sent as a text message, a phone call, an e-mail, an audible sound, and the like at the remote monitors' devices 19. In order to reduce over alerting, the server 230 may relay these alerts if the patient has failed to acknowledge the alert on his or her computing device 18.

At 1930, the mute mode alert module 278 may work with other components in the system to generate alerts when the patient's computing device 18 is muted. For example, the mute mode alert module 278 on the patient's computing device 18 may cause receiver 16 to display the alert if the patient has failed to acknowledge the alert after a predetermined amount of time (e.g., 15 minutes). Under these circumstances, receiver 16 may become the primary alert device. When this occurs, receiver 16 may generate local audio and visual alarms and send messages regarding the same to the patient's remote monitors. In some implementations, receiver 16 may work with sensor system 8 to issue these local alarms and messages. If, for example, sensor system 8 detects that the patient's computing device is muted and that the user has not acknowledged any alerts, the sensor system may trigger an alert on receiver 16.

The severity of the alert may also alter the way in which the system responds at 1940. As described above, when the mute switch is first engaged on the patient's computing device 18, a warning alert may be visually presented. If the patient fails to acknowledge this warning and the patient progresses into a low/high risk state or becomes hypoglycemic/hyperglycemic for a predetermined time period, the system (e.g., mute mode alert module 278 on the patient's computing device, the receiver, and/or a remote monitor who receives a message through a server) may automatically alert medical personnel, such as an emergency responder. In some implementations, mute mode alert module 278 may also tighten alert threshold levels when the patient's computing device is muted. This tightening of threshold levels may be similar to the tightening of threshold levels described above with respect to night mode operation. Tightening threshold levels may cause alerts to trigger sooner and/or more frequently which, in turn, may provide the patient more time to react. The adjustments described above may be activated during different hours of the day. For example, because the effects of hypoglycemia are less likely to be felt while the patient is asleep, the option of contacting medical personnel may only be enabled at nighttime hours.

The activation of the mute switch on the patient's computing device 18 may also trigger the modification of other processes at 1940, such as the dosing of insulin. These adjustments may be helpful in implementations where the patient's computing device is in communication with an insulin pump. If, for example, mute mode alert module 278 detects that the mute switch is enabled, the application may suspend the activities of the insulin pump.

Process 1907 may be applied in any situation when audio alerts may not be heard on a patient's computing device 18. As such, process 1907 is not limited to scenarios when the patient's computing device 18 is muted. Process 1907 may also apply when headphones or earphones are inserted into the patient's computing device 18, when another application running on the device suppresses sounds from other applications, and the like.

Figure 20:
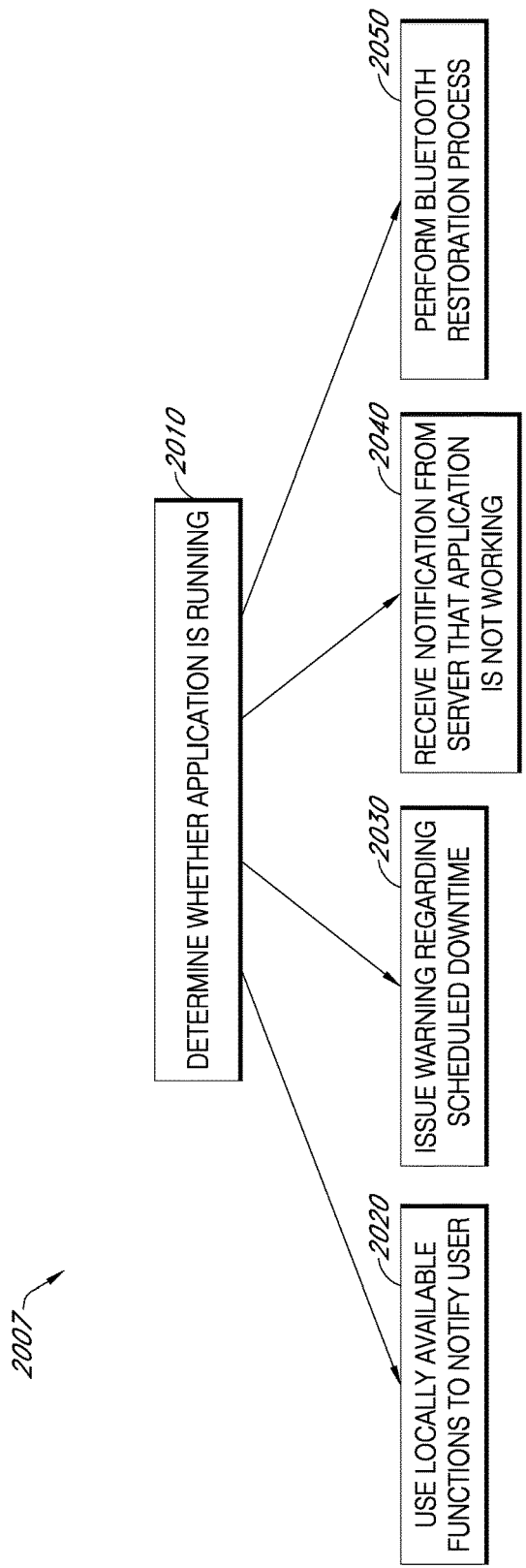
FIG. 20 illustrates a process for issuing an alert when the continuous glucose monitoring application has stopped running in accordance with some exemplary implementations.

Alert module 275 may check alert conditions so long as application 255 is running. In some circumstances, however, application 255 may stop running or functioning. This may occur if, for example, the patient's computing device 18 terminates application 255 due to competing resources, if the computing device 18 is turned off, if the user accidentally or intentionally terminates application 255, if application 255 and computing device 18 lack sufficient connectivity to receive glucose data from receiver 16 or issue alerts, and the like. Process 2007 as illustrated in FIG. 20 describes various mechanisms for alerting a user that application 255 has stopped running.

At 2010, communication failure alert module 277 may determine whether application 255 is running. If application 255 has stopped running or stopped functioning for any of the reasons described above, communication failure alert module 277 and/or computing device 18 may perform one or more of processes 2020, 2030, 2040, and 2050. These processes may be performed sequentially or substantially simultaneously.

At 2020, communication failure alert module 277 may use functions locally available on the patient's computing device 18, such as a local calendar application or alarm function, to warn a user that application 255 has stopped running. In these implementations, communication failure alert module 277 may schedule an alarm to trigger at a predetermined time, such as a half hour from the current time. Communication failure alert module 277 may continuously push this alarm out at fixed time intervals (e.g., every 15 minutes) to reschedule the alarm. Communication failure alert module 277 may be unable to reschedule the alarm, however, if application 255 is terminated. When this occurs, the local alarm may eventually trigger and sound off. The computing device 18 may display a notification indicating that application 255 is no longer working to accompany the local alarm.

In some circumstances, application 255 may have scheduled downtime. This may occur, for example, during a software upgrade or routine maintenance. At 2030, communication failure alert module 277 may issue a warning on computing device 18 and/or 19 to indicate that application 255 is scheduled to terminate. This warning may prompt the patient and his or her remote monitors to ensure that other alerting devices are available to generate alerts during this downtime.

In some circumstances, an event at computing device 18 may cause application 255 to stop running. These events may require the user to restart computing device 18 which, in turn, may stop application 255. These events may be, for example, an operating system upgrade and the like. If the glucose monitoring application is aware of these scheduled restarts, then communication failure alert module 277 may notify users ahead of time that application 255 will stop functioning.

At 2040, computing device 18 may receive a notification from a server that application 255 is not working. The server may expect a communication from application 255 at predetermined intervals (e.g., every 5 minutes). If the server does not receive the expected communication from application 255, it may send a notification, such as an e-mail or a text message, to computing device 18 and/or 19 to indicate that application 255 is not working. Upon receiving this notification, computing device 18 and/or 19 may notify communication failure alert module 277 of the same and restart application 255.

At 2050, computing device 18 may perform a Bluetooth® restoration process when application 255 has stopped running A terminated application 255 may be awakened via a signal from sensor system 8. As described above with respect to FIG. 2A, sensor system 8 may be connected to computing device 18 via an intermittent wireless connection, such as a Bluetooth® connection. Each time sensor system 8 initiates communication with hand held computing device 18, the sensor system may send a message to the computing device to awaken the glucose monitoring application 255. Computing device 18 may launch application 255 upon receiving this message. In some implementations, computing device 18 may notify communication failure alert module 277 of the same, and the module may restart application 255.

In some implementations, the application may determine whether computing device 18 may turn off due to insufficient battery power and alert the user of the same. The application may make these determinations at predetermined times. For example, if night mode operation begins at 10 PM, the application may determine whether computing device 18 has sufficient battery power to last through the end of night mode and alert the user of the same before he or she goes to sleep (i.e., just before the application enters night mode operation). If there is insufficient battery power, the application may display a notification to prompt the user to charge his or her computing device 18.

In some implementations, the application may provide in-application help to users. The application may detect if a user needs assistance if, for example, the user is spending a lot of time on a particular screen, flipping between screens, missing alerts, and the like. When this behavior is detected, the application may display pop-up messages to guide the user through the application and/or educate the user on how the system works.

To illustrate, in some implementations, application 255 may detect user interaction with the application that indicates that the user is having difficulty understanding how to pair devices with the continuous glucose monitoring system. User interaction representative of such difficulties may occur, for example, when a user stays on a particular screen in excess of a predetermined amount of time, the user flips between several predetermined screens, a combination of both, and the like. Application 255 may automatically generate a pop-up help message relate to the detected behavior. Continuing with the above example, the pop-up may provide instructions on device pairing.

In-application help may also include user help functions that educate the user on how alerts work. In one implementation, application 255 can detect if a user has acknowledged an alert using predetermined criteria, such as user acknowledgement of the alert within a predetermined amount of time. If the user does not acknowledge the alert within the predetermined amount of time, then the next time the user is interacting with application 255, the application can display a pop-up message indicating that the user did not acknowledge the previous alert. The pop-up message can also provide textual guidance as to why the user may not have acknowledged the alert and how the user can configure the alert so that the user is more likely to hear the alert the next time it is triggered. For example, if a mute switch is enabled when a low alert triggered, and a user fails to acknowledge the alert within a predetermined amount of time, application 255 may display a pop-up message informing the user that he/she did not acknowledge the low alert and that he/she should disable the mute switch to hear the alert the next time it is triggered.

In addition, application 255 can log the amount of time it takes the user to acknowledge each triggered alert. This log can later be used to modify the user's alert settings to increase the likelihood that the user receives alerts in a timely fashion. This modification can be performed automatically by the application, or the application can suggest modifications to the user, via pop-up message for example, and the user can accept or reject the modifications. Accepting the modification would automatically modify the alert settings in the application as suggested by the application.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, audible feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method comprising:
   executing, by at least one processor, an application to generate one or more alerts on a device relating to a glucose level of a patient, the executing comprising:
   accessing, by at least one processor, a current glucose level of the patient;
   accessing, by at least one processor, a first condition associated with a first alert and a second condition associated with a second alert, each of the first and second conditions defining a relationship between the current glucose level and one or more threshold values, wherein the first condition is determined and adjustable by the patient and the second condition is non-adjustable by the patient;
   determining, by at least one processor, whether the first or second condition is satisfied, and a state of the device and a state of the application; and
   generating, by at least one processor, the first alert when the first condition is satisfied or the second alert when the second condition is satisfied, wherein the first or second alert is generated based on the state of the device or the state of the application.

2. The method of claim 1, wherein the state of the device is one or more of a locked state, an unlocked state, a muted stated, and an unmuted state, and wherein the state of the application is an active state or an inactive state.

3. The method of claim 2, wherein the application is in an active state when the application is displayed on a foreground of a screen of the device, and wherein the application is in an inactive state when the application is running in a background of the screen of the device.

4. The method of claim 2, wherein the first or second alert comprise one or more non-audible alerts when the device is in a muted state, and wherein the one or more non-audible alerts comprise one or more of a vibration or a visualization displayed on a screen of the device, the visualization comprising a flashing screen or a shaded screen.

5. The method of claim 2, wherein the first or second alert comprise one or more local notifications displayed on a locked screen of the device when the device is in a locked state, and wherein the one or more local notifications display an identifier associated with the one or more alerts.

6. The method of claim 5, wherein the one or more local notifications further display the current glucose level and a trend arrow representative of a rate of change of the current glucose level.

7. The method of claim 2, wherein the first or second alert comprise one or more banners when the device is in an unlocked state and the application is in an inactive state, and wherein the one or more banners display an identifier associated with the one or more alerts for a predetermined period of time on a screen of the device.

8. The method of claim 7, wherein the first or second alert further comprise one or more audible alerts.

9. The method of claim 1, further comprising:
re-generating, by at least one processor, the first or second alert at a predetermined frequency until an acknowledgment of the first or second alert is received or when the first or second condition is no longer satisfied.

10. The method of claim 1, wherein the first or second alert comprise an urgent low alert, a low alert, a high alert, a rise rate alert, a fall rate alert, or a no data alert.

11. The method of claim 10, wherein the first alert is a low alert and the second alert is an urgent low alert.

12. The method of claim 1, further comprising:
adjusting, by at least one processor, the one or more threshold values associated with the first or second condition during a predetermined period of time, the adjusting causing the first or second condition to be satisfied more frequently than without the adjusting.

13. The method of claim 12, wherein the adjusting is performed during a night mode.

14. A system comprising:
a processor; and
a memory, wherein the processor and the memory are configured to perform operations comprising:
executing an application to generate one or more alerts on a device relating to a glucose level of a patient, the executing comprising:
accessing a current glucose level of the patient;
accessing a first condition associated with a first alert and a second condition associated with a second alert, each of the first and second conditions defining a relationship between the current glucose level and one or more threshold values, wherein the first condition is determined and adjustable by the patient and the second condition is non-adjustable by the patient;
determining whether the first or second condition is satisfied, and a state of the device and a state of the application; and
generating the first alert when the first condition is satisfied or the second alert when the second condition is satisfied, wherein the first or second alert are generated based on the state of the device or the state of the application.

15. The system of claim 14, wherein the state of the device is one or more of a locked state, an unlocked state, a muted stated, and an unmuted state, and wherein the state of the application is an active state or an inactive state.

16. The system of claim 15, wherein the application is in an active state when the application is displayed on a foreground of a screen of the device, and wherein the application is in an inactive state when the application is running in a background of the screen of the device.

17. The system of claim 15, wherein the first or second alert comprise one or more non-audible alerts when the device is in a muted state, and wherein the one or more non-audible alerts comprise one or more of a vibration or a visualization displayed on a screen of the device, the visualization comprising a flashing screen or a shaded screen.

18. The system of claim 15, wherein the first or second alert comprise one or more local notifications displayed on a locked screen of the device when the device is in a locked state, and wherein the one or more local notifications display an identifier associated with the one or more alerts.

19. The system of claim 18, wherein the one or more local notifications further display the current glucose level and a trend arrow representative of a rate of change of the current glucose level.

20. The system of claim 15, wherein the first or second alert comprise one or more banners when the device is in an unlocked state and the application is in an inactive state, and wherein the one or more banners display an identifier associated with the one or more alerts for a predetermined period of time on a screen of the device.

21. The system of claim 20, wherein the first or second alert further comprise one or more audible alerts.

22. The system of claim 14, the operations further comprising:
re-generating the first or second alert at a predetermined frequency until an acknowledgment of the first or second alert is received or when the first or second condition is no longer satisfied.

23. The system of claim 14, wherein the first or second alert comprise an urgent low alert, a low alert, a high alert, a rise rate alert, a fall rate alert, or a no data alert.

24. The system of claim 23, wherein the first alert is a low alert and the second alert is an urgent low alert.

25. The system of claim 14, further comprising adjusting the one or more threshold values associated with the first or second condition during a predetermined period of time, the adjusting causing the first or second condition to be satisfied more frequently than without the adjusting.

* * * * *

UNITED STATES PATENT AND TRADEMARK OFFICE
CERTIFICATE OF CORRECTION

| | | |
|---|---|---|
| PATENT NO. | : 10,285,591 B2 | Page 1 of 1 |
| APPLICATION NO. | : 14/919611 | |
| DATED | : May 14, 2019 | |
| INVENTOR(S) | : Katherine Yerre Koehler | |

It is certified that error appears in the above-identified patent and that said Letters Patent is hereby corrected as shown below:

In the Specification

In Column 34 at Lines 22-23, Change "running" to --running.--.

Signed and Sealed this
Twenty-seventh Day of August, 2019

Andrei Iancu
*Director of the United States Patent and Trademark Office*